US010260103B2

(12) United States Patent
Gonzalez Diaz et al.

(10) Patent No.: US 10,260,103 B2
(45) Date of Patent: Apr. 16, 2019

(54) COMPOSITIONS AND METHODS FOR DIAGNOSING THYROID TUMORS

(71) Applicant: Pontifica Universidad Catolica de Chile, Santiago (CL)

(72) Inventors: Hernan Eugenio Gonzalez Diaz, Santiago (CL); Sergio Vargas Salas, Santiago (CL); Jose Rodrigo Waldemar Martinez Solis, Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 220 days.

(21) Appl. No.: 14/647,284

(22) PCT Filed: Nov. 26, 2013

(86) PCT No.: PCT/US2013/071970
§ 371 (c)(1),
(2) Date: May 26, 2015

(87) PCT Pub. No.: WO2014/085434
PCT Pub. Date: Jun. 5, 2014

(65) Prior Publication Data
US 2015/0299808 A1    Oct. 22, 2015

Related U.S. Application Data

(60) Provisional application No. 61/775,419, filed on Mar. 8, 2013, provisional application No. 61/730,391, filed on Nov. 27, 2012.

(51) Int. Cl.
*C12Q 1/68* (2018.01)
*C12Q 1/6886* (2018.01)
*A61N 5/10* (2006.01)

(52) U.S. Cl.
CPC ............ *C12Q 1/6886* (2013.01); *A61N 5/10* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 7,598,052 | B2 | 10/2009 | Giordano et al. | |
|---|---|---|---|---|
| 8,202,692 | B2 | 6/2012 | Giordano et al. | |
| 2008/0090242 | A1* | 4/2008 | Levitan | C12Q 1/6886 435/6.13 |
| 2010/0035262 | A1 | 2/2010 | Inazawa et al. | |
| 2011/0275065 | A1* | 11/2011 | Walfish | C12Q 1/6886 435/6.1 |

FOREIGN PATENT DOCUMENTS

| CN | 101501214 A | 8/2009 |
|---|---|---|
| CN | 101608227 A | 12/2009 |
| CN | 102177252 A | 9/2011 |
| CN | 102459636 A | 5/2012 |
| CN | 103468789 A | 12/2013 |
| EP | 2366800 A1 | 9/2011 |
| MD | 4038 B1 | 5/2010 |
| WO | WO 2006/127537 A2 | 11/2006 |
| WO | WO 2007/045996 A1 | 4/2007 |
| WO | WO 2009/111881 A1 | 9/2009 |
| WO | WO 2010/056374 A2 | 5/2010 |
| WO | WO 2010/124372 A1 | 11/2010 |
| WO | WO 2011/032296 A1 | 3/2011 |
| WO | WO 2011/137519 A1 | 11/2011 |
| WO | WO 2011/143361 A2 | 11/2011 |
| WO | WO 2014/085434 A1 | 6/2014 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Ohshima et al, Leukemia and Lymphoma 44 (2), 329 (2003).*
Gonzalez et al, Thyroid 19 (9), 957 (2009).*
Melillo et al, J. Clin. Invest. 115 (4), 1068 (2005).*
Chai et al, Histopathology 59 (3), 496 (Sep. 2011).*
Kebebew et al, Cancer 106 (12), 2592 (2006).*
Giaginis et al, APMIS 118 (3), (Mar. 2010).*
Lodyga et al, Oncogene 28 (7), 937 (Feb. 2009).*
Chen et al, J. Cell. Biochem. 92 (6), 1246 (2004).*
International Search Report and Written Opinion in International Application No. PCT/US2013/071970, dated Feb. 17, 2014, 12 pages.
International Preliminary Report on Patentability in International Application No. PCT/US2013/071970, dated Jun. 2, 2015, 8 pages.
Cheng, S., et al. "A High-Throughput Proteomic Approach Provides Distinct Signatures for Thyroid Cancer Behavior." Clinical Cancer Research (2011); 17(8): 2385-2394.
Gubala, E., et al. "Gene expression analysis by DNA microarray in papillary thyroid cancer." Endokrynologia Polska (2005); 56(5): 752-757.
Sancho, M., et al., "Expression and function of the chemokine receptor CCR7 in thyroid carcinomas." Journal of Endocrinology (2006); 191(1): 229-238.

\* cited by examiner

*Primary Examiner* — James Martinell
(74) *Attorney, Agent, or Firm* — Cooley LLP

(57) ABSTRACT

The present invention provides dignostic assays for identifying thyroid cancer in a biological sample, including a fine needle aspirate, as well as related compositions and kits useful in practicing the methods of the invention.

19 Claims, 9 Drawing Sheets

Specification includes a Sequence Listing.

| Classifier | Name | AUC | FP | TP |
|---|---|---|---|---|
| GENE1 | CXCR3 | 0,559 | 0,796 | 0,969 |
| GENE2 | CXC3A | 0,614 | 0,648 | 0,898 |
| GENE3 | CXCRB | 0,611 | 0,759 | 0,918 |
| GENE4 | CXCR4 | 0,646 | 0,888 | 0,979 |
| GENE5 | CCR3 | 0,705 | 0,629 | 0,887 |
| GENE6 | CXCL9 | 0,605 | 0,759 | 0,949 |
| GENE7 | CXCL10 | 0,568 | 0,740 | 0,979 |
| GENE8 | CXCL11 | 0,574 | 0,759 | 0,949 |
| GENE9 | SPAG9 | 0,516 | 0,814 | 0,959 |
| GENE10 | CK19 | 0,841 | 0,204 | 0,846 |
| GENE11 | TIMP1 | 0,865 | 0,092 | 0,785 |
| GENE12 | CLDN1 | 0,851 | 0,203 | 0,785 |
| GENE13 | CAR | 0,672 | 0,796 | 0,959 |
| GENE14 | NEC-1 | 0,549 | 0,963 | 1,000 |
| GENE15 | XB130 | 0,505 | 0,814 | 0,928 |
| GENE16 | HO-1 | 0,646 | 0,777 | 0,989 |
| GENE17 | CCR7 | 0,747 | 0,500 | 0,877 |
| GENE18 | CXCL4 | 0,543 | 0,870 | 0,938 |

*FIG. 2*

|  | SV | GENE11 | GENES (10,11, 12) | GENE10 | GENE12 |
|---|---|---|---|---|---|
| SV | - | 0,07565 | 0,08511 | 0,09062 | 0,10166 |
| GENE11 | 0,02056* | - | 0,00946 | 0,01497 | 0,026 |
| GENES (10,11, 12) | 0,01623* | 0,15067 | - | 0,00552 | 0,01655 |
| GENE10 | 0,00871* | 0,63883 | 0,87176 | - | 0,01103 |
| GENE12 | 0,00534* | 0,38495 | 0,605575 | 0,70021 | - |

Significance Level (alpha): 0.05
Upper Triangle: AUC differences
Bottom Triangle: p-values
*p-value < 0.05
Global p-value: N.D. (Matrix LSL T is singular)

| Parameters | SV | FM72 | FM208 | Gene 10 | Gene 11 | Gene 12 | Genes (10,11,12) | Afirma |
|---|---|---|---|---|---|---|---|---|
| AUC | 0,987 | 0,987 | 0,980 | 0,840 | 0,866 | 0,851 | 0,890 | 0,900 |
| 95% CI | 0,967 - 1,000 | 0,911 - 0,999 | 0,948 - 1,000 | 0,809 - 0,929 | 0,824 - 0,946 | 0,809 - 0,921 | 0,85 - 0,95 | |
| Sensitivity (%) | 97,87 | 95,05 | 94,32 | 84,69 | 78,57 | 78,57 | 87,23 | 92,00 |
| 95% CI | 89,0 - 100 | 88,71 - 99,95 | 85,46 - 99,48 | 77,51 - 92,43 | 78,76 - 93,23 | 71,44 - 88,24 | 78,76 - 93,23 | |
| Specificity (%) | 92,60 | 99,00 | 96,15 | 75,93 | 91,74 | 79,63 | 72,22 | 58,00 |
| 95% CI | 75,7 - 99,0 | 61,92 - 93,70 | 66,27 - 95,81 | 64,40 - 87,96 | 58,36 - 83,54 | 66,47 - 89,37 | 58,35 - 83,54 | |
| Positive Predictive Value | 95,84 | 99,40 | 97,71 | 83,79 | 93,32 | 85,00 | 84,53 | 68,66 |
| Negative Predictive Value | 96,15 | 91,99 | 90,68 | 77,15 | 74,46 | 71,67 | 76,47 | 87,88 |
| Pre-Test (Cancer Prevalence) | 63,51 | 63,51 | 63,51 | 59,49 | 59,49 | 59,49 | 63,51 | 50,00 |
| Likehood Ratio + | 13,23 | 95,05 | 24,50 | 3,52 | 9,51 | 3,86 | 3,14 | 2,19 |
| Post-Test + | 95,84 | 99,40 | 97,71 | 83,79 | 93,32 | 85,00 | 84,53 | 68,66 |
| Pre-Test (Cancer Prevalence) | 63,51 | 63,51 | 63,51 | 59,49 | 59,49 | 59,49 | 59,49 | 50,00 |
| Likehood Ratio - | 0,02 | 0,05 | 0,06 | 0,20 | 0,23 | 0,27 | 0,18 | 0,14 |
| Post-Test - | 3,85 | 8,01 | 9,32 | 22,85 | 25,54 | 28,33 | 20,62 | 12,12 |

*FIG. 7*

SV AlGORITHM

| SAMPLE | Surgical Training Set | Surgical Testing Set 1 | FNA Testing Set 2 |
|---|---|---|---|
| SENSITIVITY | 98% | 95% | 96% |
| SPECIFICITY | 93% | 90% | 89% |
| PPV | 95 % | 83 % | 75% |
| NPV | 96 % | 98 % | 98% |
| Cancer prevalence | 63 % | 33% | 26% |

FIG. 9

COMPOSITIONS AND METHODS FOR DIAGNOSING THYROID TUMORS

CROSS-REFERENCE TO RELATED APPLICATIONS

This application is a National Stage entry of PCT/US2013/071970, filed Nov. 26, 2013, which claims priority to U.S. Provisional Patent Application Ser. No. 61/730,391 filed Nov. 27, 2012 and U.S. Provisional Patent Application Ser. No. 61/775,419 filed Mar. 8, 2013. These applications are hereby incorporated herein by reference in their entireties.

SEQUENCE LISTING

The Sequence Listing associated with this application is provided in text format in lieu of a paper copy, and is hereby incorporated by reference into the specification. The name of the text file containing the Sequence Listing is BMRC_001_02WO_ST25.txt. The text file is about 57 KB, was created on Nov. 26, 2013, and is being submitted electronically via EFS-Web.

BACKGROUND

Field

The present invention is directed to compositions and methods for diagnosing thyroid cancer and evaluating thyroid nodules to determine if they are benign or cancerous.

Description of the Related Art

Approximately 350,000 fine needle aspirate (FNA) biopsies of thyroid nodules are performed every year in the US, of which 20% are reported as indeterminate with respect to whether the nodules are cancerous or not. These patients, in most cases, undergo surgery given the risk of cancer, which ranges between only 15 to 30%. This means that most patients do not require surgical removal of the thyroid. Considering the acute and long term risks associated to thyroid surgery, as well as the costs for patients and the health system, there is an urgent need for a tool that will improve the diagnostic accuracy of thyroid FNA biopsies.

Recently, new tests have been placed in the US market that, to a variable degree, improve the diagnosis of indeterminate thyroid nodules. These include the Afirma® thyroid FNA analysis test (Veracyte, South San Francisco, Calif.), which is a gene expression classifier assay based on 167 genes. However, the Afirma® test would change the surgical conduct correctly in only about 50% of the cases. Two other test include those developed by Quest Diagnostics and Asuragen, which are based on mutational analysis of known biomarkers accepted by the American Thyroid Association. However, adequate clinical trial validation is lacking Unfortunately, the Afirma® test demands the analysis of a large number of biomarkers, all tests must be performed in central laboratories, and require the sample be shipped for analysis. In addition, a second FNA must be performed to obtain an adequate sample to perform these assays.

Clearly, there is a need in the art for improved methods and compositions for evaluating thyroid nodules and diagnosing thyroid cancer. The present invention meets this need by providing a new and simplified diagnostic approach for evaluating thyroid nodules that have been reported to be indeterminate by a fine needle aspiration (FNA) biopsy, and provides additional advantages.

BRIEF SUMMARY

The present invention provides compositions, methods and kits for determining the presence or absence of malignant or benign tissue in a sample, e.g., a thyroid tissue or thyroid nodule sample.

In certain embodiments, the present invention provides a method of diagnosing thyroid cancer in a subject comprising: determining expression levels of three or more gene products of a thyroid tissue sample obtained from the subject, wherein the three or more gene products are expressed by one or more genes listed in Table 1 and wherein at least one of the gene products is expressed by a CXCR3, CCR3, CXCL10, CAR, XB130, HO-1 or CCR7 gene; and identifying the thyroid tissue sample as cancerous or benign by correlating the expression levels determined with the presence or absence of thyroid cancer in the thyroid tissue sample. In various embodiments, the method is used to determine whether the tissue sample is cancerous or benign, e.g., to determine whether the subject has a cancer, such as, e.g., a thyroid cancer.

In certain embodiments of methods of the present invention, the correlating step is performed by comparing the expression levels of the three or more gene products to normal control expression levels for each of the gene products, wherein the thyroid tissue sample is identified as cancerous if there is a difference in the expression levels of the three or more gene products between the thyroid tissue sample and the normal control expression levels. In related embodiments, the thyroid tissue sample is identified as cancerous if there is a difference in the expression levels of four or more gene products between the thyroid tissue sample and the normal control expression levels. In certain embodiments, the normal control expression level is an expression level in a normal thyroid tissue sample, while in certain embodiments, the normal control expression level is a predetermined value based on expression levels in a plurality of normal thyroid tissue samples. In certain embodiments of methods of the present invention, the thyroid tissue sample is identified as malignant or cancerous if the expression level of any one or more of CXCR3, CXCL 11, SPAG-9, CAR, Nectin-1, XB-130 and/or CXCL4 genes is decreased; and/or the expression level of any one or more of CXCR3A, CXCR3B, CXCR4, CCR3, CXCL9, CXCL10, CK-19, TIMP-1, CLDN-1, and/or CCR7 genes is increased in the thyroid tissue sample as compared to the normal control expression level, wherein the total number of genes with increased or decreased expression is at least three.

In certain embodiments of methods of the present invention, the correlating step is performed by comparing the expression level of the three or more gene products to a cancer control expression level for each gene product, wherein the thyroid tissue sample is identified as cancerous if there is substantially no difference in the expression level of the three or more gene products between the thyroid tissue sample and the cancer control expression levels. In particular embodiments, the thyroid tissue sample is identified as cancerous if there is substantially no difference in the expression level of four or more gene products between the thyroid tissue sample and the cancer control expression levels. In certain embodiments, the cancer control expression level is an expression level in a cancerous thyroid tissue sample. In particular embodiments, the cancer control expression level is a predetermined value based on expression levels in a plurality of cancerous thyroid tissue samples.

In certain embodiments of methods of the present invention, the correlating step comprises comparing the expression level to gene expression data determined for the three or more gene products in the following two sets of biological samples: (i) a plurality of normal thyroid tissue samples; and (ii) a plurality of cancerous thyroid tissue samples, wherein the thyroid tissue sample is identified as cancerous if there is a difference in the expression level of the three or more gene products between the thyroid tissue sample and the gene expression data of (i), or if there is substantially no difference in the gene expression level of the one or more gene products between the thyroid tissue sample and the gene expression date of (ii).

In particular embodiments of methods of the present invention, the correlating step is performed using a classifier that identifies atypical CT values and/or non-atypical CT values. In certain embodiments, the classifier was generated using gene expression data determined for the three or more gene products from a plurality of normal thyroid tissue samples and/or cancerous thyroid tissue samples.

In particular embodiments of methods of the present invention, the thyroid tissue sample was obtained by needle aspiration, fine needle aspiration, core needle biopsy, vacuum assisted biopsy, large core biopsy, incisional biopsy, excisional biopsy, or punch biopsy.

In various embodiments of methods of the present invention, the gene product is RNA, e.g., mRNA, rRNA, tRNA, or miRNA. In certain embodiments, the RNA expression level is determined using microarray, SAGE, blotting, RT-PCR, quantitative PCR or qNPA. In various embodiments of the present invention, the gene product is protein. In certain embodiments, the protein gene expression is determined using ELISA, mass spectrophotometry, blotting, protemics techniques, or immunohistochemistry.

In various embodiments of methods, compositions and kits of the present invention, the three or more gene products comprise or consist of: three or more gene products of the CXCR3, CCR3, CXCL10, CK19, TIMP-1, CLDN-1, CAR, XB130, HO-1 and CCR7 genes; the gene products of the CXCR3, CCR3, CXCL10, CK19, TIMP-1, CLDN-1, CAR, HO-1 and CCR7 genes; the gene products of the CCR3, TIMP-1, CAR and XB130 genes; the gene products of the CXCL10, TIMP-1, CAR and CCR7 genes; the gene products of the TIMP-1, CAR and CCR7 genes; or the gene products of the CXCL10, TIMP-1, CLDN-1 and CCR7 genes. In particular embodiments of methods, compositions and kits related to any of these gene sets, the expression level of CXCR3, CXC L11, SPAG-9, CAR, Nectin-1, XB-130 and/or CXCL4 genes is decreased; and/or the expression level of CXCR3A, CXCR3B, CXCR4, CCR3, CXCL9, CXCL10, CK-19, TIMP-1, CLDN-1, HO-1 and/or CCR7 genes is increased. Accordingly, in particular embodiments, the three or more gene products comprise or consist of gene products of the CXCR3, CCR3, CXCL10, CK19, TIMP-1, CLDN-1, CAR, XB130, HO-1 and CCR7 genes, wherein the expression levels of one or more, two or more, or all of the CXCR3, CAR, and XB130 genes are decreased and/or the expression levels of one or more, two or more, three or more, four or more, five or more, six or more, or all of the CCR3, CXCL10, CK19, TIMP-1, CLDN-1, HO-1, and CCR7 genes are increased. In other particular embodiments, the three or more gene products comprise or consist of gene products of the CXCR3, CCR3, CXCL10, CK19, TIMP-1, CLDN-1, CAR, HO-1 and CCR7 genes, wherein the expression levels of one or both of the CXCR3 and CAR genes are decreased and/or the expression levels of one or more, two or more, three or more, four or more, five or more, six or more, or all of the CCR3, CXCL10, CK19, TIMP-1, CLDN-1, HO-1, and CCR7 genes are increased. In other particular embodiments, the three or more gene products comprise or consist of gene products of the CCR3, TIMP-1, CAR and XB130 genes, wherein the expression levels of one or more or both of the CAR and XB130 genes are decreased and/or the expression levels of one or more or both of the CCR3 and TIMP-1 genes are increased. In other particular embodiments, the three or more gene products comprise or consist of gene products of the CXCL10, TIMP-1, CAR and CCR7 genes, wherein the expression levels of the CAR gene is decreased and/or the expression levels of one or more, two or more, or all of the CXCL10, TIMP-1, and CCR7 genes are increased. In other particular embodiments, the three or more gene products comprise or consist of gene products of the TIMP-1, CAR and CCR7 genes, wherein the expression levels of the CAR gene is decreased and/or the expression levels of one or more or both of the TIMP-1 and CCR7 genes are increased. In other particular embodiments, the three or more gene products comprise or consist of gene products of the CXCL10, TIMP-1, CLDN-1 and CCR7 genes, wherein the expression levels of one or more, two or more, three or more, or all of the CXCL10, TIMP-1, CLDN-1 and CCR7 genes are increased.

In certain embodiments, methods of the present invention further comprise the step of performing a cytological analysis on a thyroid tissue sample obtained from the subject to obtain a preliminary diagnosis. In particular embodiments, samples with a preliminary diagnosis of intermediate or indeterminate are further analyzed by determining gene product expression levels and correlating them with benign or malignant tissue according to methods of the present invention. In particualr embodiments, the tissue sample cytologically analyzed and the tissue sample used in determining gene product expression levels are the same tissue sample. In certain embodiments of methods of the present invention, the tissue sample was obtained by fine needle aspiration.

In particular embodiments of methods, composition, or kits of the present invention, the thyroid tissue sample is diagnosed as cancerous or benign with a sensitivity of greater than or equal to 92% or greater than or equal to 97%, the thyroid tissue sample is diagnosed as cancerous or benign with a specificity of greater than or equal to 60% or greater than or equal to 90%, the thyroid tissue sample is diagnosed as cancerous or benign with a positive predictive value of greater than or equal to 50% or greater than or equal to 90%, the thyroid tissue sample is diagnosed as cancerous or benign with a negative predictive value of greater than or equal to 92% or greater than or equal to 94%, the thyroid tissue sample is diagnosed as cancerous or benign with a positive likelihood ratio of greater than or equal to 2 or greater than or equal to 10, the thyroid tissue sample is diagnosed as cancerous or benign with a positive post-test probability of greater than or equal to 50% or greater than or equal to 80%, the thyroid tissue sample is diagnosed as cancerous or benign with a negative likelihood ratio of less than or equal to 0.14 or less than or equal to 0.08, and/or the thyroid tissue sample is diagnosed as cancerous or benign with a negative post-test probability of less than or equal to 7.0% or less than or equal to 3.0%.

Particular embodiments of methods of the present invention further comprise obtaining the thyroid tissue sample from the subject.

Particular embodiments of methods of the present invention further comprise surgically removing the subject's thyroid, or a portion thereof, if the thyroid tissue sample is diagnosed as cancerous.

In a related embodiments, the present invention includes a kit for diagnosing thyroid cancer, said kit comprising three or more reagents for detecting gene products, wherein the three or more reagents each detect a different gene product, wherein the gene products are expressed by one or more genes listed in Table 1, and wherein at least one of the gene products is expressed by a CXCR3, CCR3, CXCL10, CAR, XB130, HO-1 or CCR7 gene. In certain embodiments, the reagents are antibodies, and each antibody specifically binds to a polypeptide gene product. In certain embodiments, the reagents are oligonucleotides or sets of oligonuclotides, and each oligonucleotide specifically binds to a nucleic acid gene product. In certain embodiments, the reagents are each attached to a substrate. In particular embodiments, the reagents are covalently attached to the substrate. In particular embodiments, the reagents are each attached to a discrete region of a solid substrate. In particular embodiments, the reagents are oligonucleotides or sets of oligonucleotides covalently bound to a solid substrate, the solid substrate is optionally an array, and the array is optionally a microarray. In particular embodiments, the reagents are sets of oligonucleotides, and the sets of oligonucleotides comprise DNA. In particular embodiments, the reagents are sets of oligonucleotides, and each set of oligonucleotides specifically hybridizes to one of the gene products. In one embodiment, each set of oligonucleotides comprise amplification primers capable of PCR amplifying one of the gene products. In certain embodiments of various kits of the present invention, the gene products comprise or consist of: three or more gene products of the CXCR3, CCR3, CXCL10, CK19, TIMP-1, CLDN-1, CAR, XB130, HO-1 and CCR7 genes; the gene products of the CXCR3, CCR3, CXCL10, CK19, TIMP-1, CLDN-1, CAR, HO-1 and CCR7 genes; the gene products of the CCR3, TIMP-1, CAR and XB130 genes; the gene products of the CXCL10, TIMP-1, CAR and CCR7 genes; the gene products of the TIMP-1, CAR and CCR7 genes; or the gene products of the CXCL10, TIMP-1, CLDN-1, and CCR7 genes.

In certain embodiments of methods, compositions and kits of the present invention, the reagents are labeled. In particular embodiments, a kit of the present invention further comprises one or more solutions suitable for binding said reagents to said gene products. In certain embodiments of kits of the present invention, the reagents are sets of oligonucleotides, and the kit further comprises one or more additional reagents for performing a PCR assay. In particular embodiments, the one or more additional reagents are selected from a thermostable polymerase, a mixture of deoxynucleotides, and a detectably labeled probe. In certain embodiments, the detectably labeled probe comprises a fluorophore and a quenching moiety. In particular embodiments, the detectably labeled probe emits a detectable signal when the probe is cleaved but not when the probe is intact.

In various embodiments of kits of the present invention, the kit further comprises one or more reagents for processing a thyroid tissue sample. In particular embodiments, the processing of the thyroid tissue sample comprises extracting the gene products from the thyroid tissue sample, and in certain embodiments the gene products are proteins or nucleic acids.

In various embodiments, a kit of the present invention further comprises one or more control gene products.

In particular embodiments of kits of the present invention, one or more of the following (when present in the kit) are present in separate containers: reagents for detecting gene products, the solution, any additional reagent, and control gene products.

In other related embodiments, the present invention provides a method of treating thyroid cancer, comprising: identifying a thyroid tissue sample obtained from the subject as cancerous according to a method of the present invention or using a kit of the present invention; and surgically removing the subject's thyroid or a portion thereof, or performing radiation therapy, chemotherapy, or hormone therapy on the subject

BRIEF DESCRIPTION OF THE SEVERAL VIEWS OF THE DRAWINGS

FIG. 2 provides receiving operating characteristic (ROC) curve data of each of the 18 individual genes indentified in Example 1. AUC: area under the curve, FP: False positive, TP: True positive.

FIG. 7 provides a comparison table of the classifying performance of three new classifiers developed with the training set (SV, FM72, FM208), best individual genes (Gene 10, Gene 11, Gene 12), combination of the best genes (Genes (10, 11, 12)) and the Afirma® classifier by Veracyte (Affirma).

FIG. 9 provides a comparison table showing the sensitivity, specificity, PPV and NPV values obtained using the SV algorithm on surgical and FNA samples.

DETAILED DESCRIPTION

Figure 1:
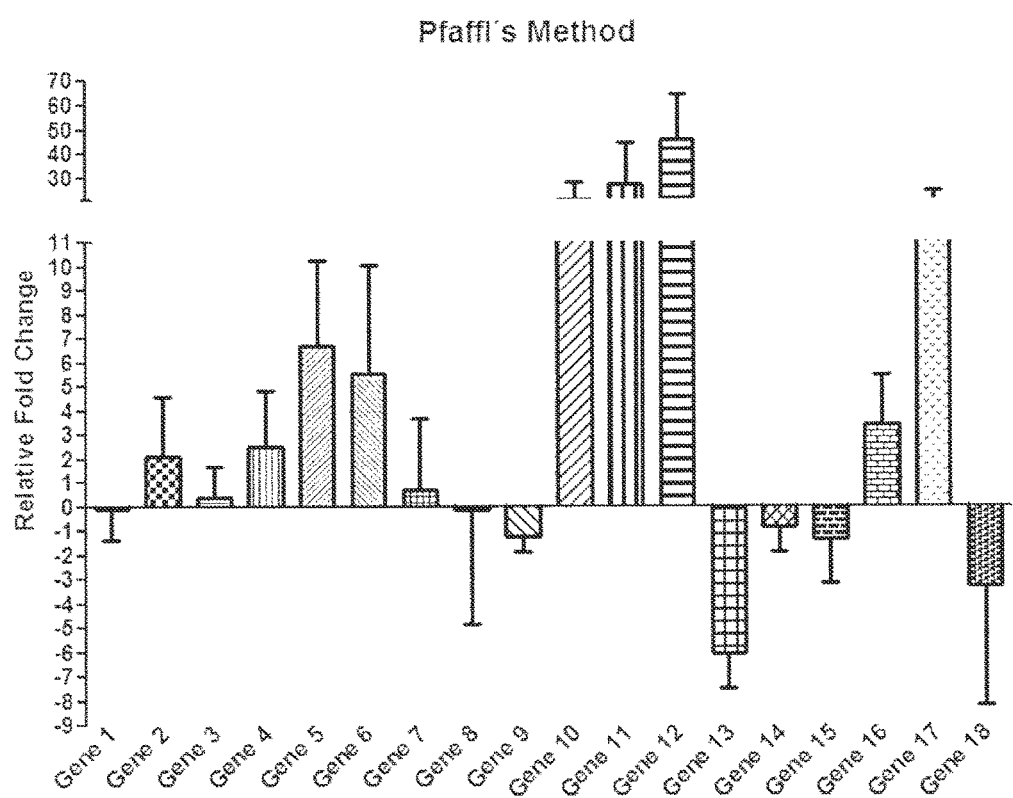
FIG. 1 provides a graph showing the differential expression between cancer samples (100) and benign nodules (56) of 18 genes as determined by quatitative real time PCR and analyzed by the relative quantification model proposed by Pfaffl. The value zero corresponds to the gene expression of benign nodules and bars correspond to the variation of gene expression in cancer samples (relative fold change). The 18 genes are identified in Example 1.

The present invention is based, in part, on the identification of a small panel of genes and various subcombinations thereof, which allow the accurate classifying of thyroid samples as malignant or benign. The combinations of genes used according to the present invention results in a surprising improvement in the ability to classify thyroid nodules, as compared to the use of individual genes or previously described gene combinations. In addition, the gene panel provides superior diagnostic and classifying results as compared to previously available gene sets and related methods. For example, the gene sets and methods of the present invention show better predictability and reliability than the Afirma® gene classifier. Use of the gene sets of the present invention with a biphasic stepwise algorithm avoids overfitting and is able to adequately classify patients with outlier gene profiles, taking into account the gene profile expression variations of the population. Furthermore, the small gene panel of the present invention allows for a kit that can be distributed to pathology laboratories, thus lowering costs, as well as simplifying and expediting the diagnostic process. Another advantage of the small gene panel is that it requires a reduced amount of tissue sample, potentially allowing sufficient mRNA to be extracted from the original FNA sample, thus avoiding the need to subject a patient to a second FNA.

In the following description, certain specific details are set forth in order to provide a thorough understanding of various embodiments of the invention. However, one skilled in the art will understand that the invention may be practiced without these details.

Definitions

Unless defined otherwise, all technical and scientific terms used herein have the same meaning as commonly understood by those of ordinary skill in the art to which the invention belongs. For the purposes of the present invention, the following terms are defined below.

The words "a" and "an" denote one or more, unless specifically noted.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about," it is specifically contemplated that the term about can be omitted.

By "coding sequence" is meant any polynucleotide sequence that contributes to the code for the polypeptide product of a gene. By contrast, the term "non-coding sequence" refers to any polynucleotide sequence that does not contribute to the code for the polypeptide product of a gene.

Unless the context requires otherwise, throughout the present specification and claims, the word "comprise" and variations thereof, such as, "comprises" and "comprising" are to be construed in an open, inclusive sense, that is as "including, but not limited to".

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

A "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7, 1.8, etc.) an amount or level described herein.

Reference throughout this specification to "an embodiment" or "one embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

An "increased" or "enhanced" amount is typically a "statistically significant" amount, and may include an increase that is 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 2.1, 2.2, 2.3, 2.4, etc.) an amount or level described herein.

By "isolated" is meant material that is substantially or essentially free from components that normally accompany it in its native state. For example, an "isolated polynucleotide," as used herein, includes a polynucleotide that has been purified from the sequences that flank it in its naturally-occurring state, e.g., a DNA fragment which has been removed from the sequences that are normally adjacent to the fragment. Alternatively, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. A cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

By "obtained from" is meant that a sample such as, for example, a tissue, a polynucleotide or a polypeptide, is isolated from, or derived from, a particular source, such as a desired organism (e.g., subject) or a specific tissue within a desired organism. For example, a tissue sample may be obtained from a subject, or a polynucleotide or polypeptide may be obtained from a tissue or a biological fluid isolated directly from a subject. "Derived from" or "obtained from" can also refer to the source of a tissue or a polypeptide or polynucleotide sequence.

The recitation "polynucleotide" or "nucleic acid" as used herein designates mRNA, RNA, cRNA, rRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA and RNA. As will be understood by those skilled in the art, in various embodiments, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man. The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

The term "polynucleotide variant" refers to polynucleotides displaying substantial sequence identity with a reference polynucleotide sequence or polynucleotides that hybridize with a reference sequence under stringent conditions that are defined hereinafter. This term also encompass polynucleotides that are distinguished from a reference polynucleotide by the addition, deletion or substitution of at least one nucleotide. Accordingly, the term "polynucleotide variant" includes polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide, or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs that encode these enzymes.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

The terms "polypeptide" and "protein" are used interchangeably herein to refer to a polymer of amino acid residues and to variants and synthetic and naturally occurring analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers and naturally occurring chemical derivatives thereof.

A "subject," as used herein, includes any animal that exhibits a symptom, or is at risk for exhibiting a symptom, which can be treated or diagnosed according to the invention. Also included are subjects for which it is desirable to profile levels of gene products of the invention, for diagnostic or other purposes. Suitable subjects (patients) include laboratory animals (such as mouse, rat, rabbit, or guinea pig), farm animals, and domestic animals or pets (such as a cat or dog). Mammals, including on-human primates and humans, are included.

"Treatment" or "treating," as used herein, includes any desirable effect on the symptoms or pathology of a disease or condition, e.g., thyroid cancer, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type", as used herein, refers to a microorganism (e.g., a bacterial species or strain), gene or gene product that has the characteristics of that microorganism (e.g., bacterial species or strain), gene or gene product when isolated from a naturally-occurring source. A wild-type gene or gene product (e.g., a polypeptide) is that which is most frequently observed in a population and is thus arbitrarily designed the "normal" or "wild-type" form of the gene.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., Molecular Cloning: A Laboratory Manual (3rd Edition, 2000); DNA Cloning: A Practical Approach, vol. I & II (D. Glover, ed.); Oligonucleotide Synthesis (N. Gait, ed., 1984); Oligonucleotide Synthesis: Methods and Applications (P. Herdewijn, ed., 2004); Nucleic Acid Hybridization (B. Hames & S. Higgins, eds., 1985); Nucleic Acid Hybridization: Modern Applications (Buzdin and Lukyanov, eds., 2009); Transcription and Translation (B. Hames & S. Higgins, eds., 1984); Animal Cell Culture (R. Freshney, ed., 1986); Freshney, R. I. (2005) Culture of Animal Cells, a Manual of Basic Technique, 5th Ed. Hoboken N.J., John Wiley & Sons; B. Perbal, A Practical Guide to Molecular Cloning (3rd Edition 2010); Farrell, R., RNA Methodologies: A Laboratory Guide for Isolation and Characterization (3rd Edition 2005), Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3, 4-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, (2002, Cold Spring Harbor Laboratory, ISBN 0-87969-630-3).

Certain embodiments may employ conventional biology methods, software and systems for diagnostic purposes of the present invention. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

Certain embodiments may employ various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Diagnostic Assays

The present invention is based, in part, on the identification of novel biomarkers of thyroid cancer, which allow the classification of a thyroid tumor or nodule as benign or cancerous, i.e., malignant. Accordingly, the present invention provides diagnostic assays and related kits for analyzing a biological sample obtained from a subject, in order to determine whether the subject has thyroid cancer or not. In various embodiments, methods and kits of the present invention are used to diagnose or detect the presence or absence of thyroid cancer in a subject, e.g., by determining the presence or absence of thyroid cancer cells is a biological sample obtained from the subject. In particular embodiments, methods and kits of the present invention are used to diagnose the presence or absence of thyroid cancer in a subject previously diagnosed as indeterminate, e.g., by cytological analysis.

Abnormal growth in the thyroid can result in the formation of nodules, which can be either benign or cancerous (i.e., malignant). Thyroid cancer includes at least four different kinds of malignant tumors of the thyroid gland: papillary, follicular, medullary and anaplastic; malignant subtypes include, e.g., follicular carcinoma (FC), papillary thyroid carcinoma (PTC), follicular variant of papillary carcinoma (FVPTC), medullary thyroid carcinoma (MTC), Hurthle cell carcinoma (HC), and anaplastic thyroid carcinoma (ATC). Examples of benign (non-cancerous) thyroid tumors or nodules include, e.g., follicular adenoma (FA), nodular hyperplasia (NHP), lymphocytic thyroiditis (LCT), and Hurthle cell adenoma (HA). In aspects of the invention, the thyroid cancer is an aggressive cancer or has metastatic potential, e.g., an aggressive medullary or follicular thyroid cancer or a medullary or follicular thyroid cancer with metastatic potential. In particular embodiments of the invention, the thyroid cancer is anaplastic thyroid carcinoma (ATC). "Metastatic potential" refers to the ability or possibility of a cancer cell moving from the initial site (i.e. thyroid) to other sites in the body. One of skill in the art will appreciate that methods of the present invention may be readily used to diagnose or detect the presence or absence of any of these cancerous tumors or non-cancerous conditions of the thyroid by utilizing a suitable panel of reference control samples.

The term "diagnose" or "diagnostic" or "diagnosed" includes identifying the presence or nature of a pathologic condition, such as thyroid cancer, characterizing the risk of developing such a condition, and/or measuring the change (or no change) of a pathologic condition in response to therapy. Diagnostic methods may differ in their sensitivity and specificity. In certain embodiments, the "sensitivity" of a diagnostic assay refers to the percentage of diseased cells, tissues or subjects which test positive (percent of "true positives"). Diseased cells, tissues or subjects not detected by the assay are typically referred to as "false negatives." Cells, tissues or subjects that are not diseased and which test negative in the assay may be termed "true negatives." In certain embodiments, the "specificity" of a diagnostic assay may be defined as one (1) minus the false positive rate, where the "false positive" rate is defined as the proportion of those samples or subjects without the disease and which test positive. While a particular diagnostic method may not provide a definitive diagnosis of a condition, it suffices if the method provides a positive indication that aids in diagnosis.

In particular embodiments of methods and kits of the present invention, a thyroid tissue or nodule sample is diagnosed as cancerous or benign with a sensitivity greater than or equal to 90%, greater than or equal to 91%, greater than or equal to 92%, greater than or equal to 93%, greater than or equal to 94%, greater than or equal to 95%, greater than or equal to 96%, greater than or equal to 97%, greater than or equal to 98%, or greater than or equal to 99%.

In particular embodiments of methods and kits of the present invention, a thyroid tissue or nodule sample is diagnosed as cancerous or benign with a specificity of greater than or equal to 50%, greater than or equal to 60%, greater than or equal to 70%, greater than or equal to 80%, greater than or equal to 90%, or greater than or equal to 95%.

In particular embodiments of methods and kits of the present invention, a thyroid tissue or nodule sample is diagnosed as cancerous or benign with a positive predictive value of greater than or equal to 50%, greater than or equal to 60%, greater than or equal to 70%, greater than or equal to 80%, greater than or equal to 90%, or greater than or equal to 95%.

In particular embodiments of methods and kits of the present invention, a thyroid tissue or nodule sample is diagnosed as cancerous or benign with a negative predictive value of greater than or equal to 90%, greater than or equal to 91%, greater than or equal to 92%, greater than or equal to 93%, greater than or equal to 94%, greater than or equal to 95%, greater than or equal to 96%, greater than or equal to 97%, greater than or equal to 98%, or greater than or equal to 99%.

In particular embodiments of methods and kits of the present invention, a thyroid tissue or nodule sample is diagnosed as cancerous or benign with a positive likelihood ratio of greater than or equal to 2, greater than or equal to 3, greater than or equal to 4, greater than or equal to 5, greater than or equal to 6, greater than or equal to 7, greater than or equal to 8, greater than or equal to 10, greater than or equal to 15, greater than or equal to 20, or greater than or equal to 25.

In particular embodiments of methods and kits of the present invention, a thyroid tissue or nodule sample is diagnosed as cancerous or benign with a positive post-test probability of greater than or equal to 50%, greater than or equal to 60%, greater than or equal to 70%, greater than or equal to 80%, greater than or equal to 90%, or greater than or equal to 95%.

In particular embodiments of methods and kits of the present invention, a thyroid tissue or nodule sample is diagnosed as cancerous or benign with a negative likelihood ratio of less than or equal to 0.20, less than or equal to 0.18, less than or equal to 0.16, less than or equal to 0.14, less than or equal to 0.12, less than or equal to 0.10, less than or equal to 0.08, or less than or equal to 0.06.

In particular embodiments of methods and kits of the present invention, a thyroid tissue or nodule sample is diagnosed as cancerous or benign with a negative post-test probability of less than or equal to 10.0%, less than or equal to 9.0% less than or equal to 8.0%, less than or equal to 7.0%, less than or equal to 6.0%, less than or equal to 5.0%, less than or equal to 4.0% or less than or equal to 3.0%.

In particular embodiments of methods and kits of the present invention, a thyroid tissue or nodule sample is diagnosed as cancerous or benign with a sensitivity of greater than or equal to 92% or greater than or equal to 97% and a specificity of greater than or equal to 60% or greater than or equal to 90%. In particular embodiments, the AUC is greater than 0.97, with both sensitivity and specificity values greater than or equal to 92% and 60%, respectively. In particular embodiments, the AUC is greater than 0.97, with both sensitivity and specificity values greater than or equal to 92% and 90%, respectively. In particular embodiments, the AUC is greater than 0.97, with both sensitivity and specificity values greater than or equal to 97% and 90%, respectively.

In some embodiments, the present invention provides a method of diagnosing, identifying, or classifying a cancer, e.g., a thyroid cancer, comprising the steps of: obtaining an expression level for one or more gene products of a biological sample, e.g., a thyroid tissue sample; and identifying the biological sample as benign wherein the gene product expression level(s) indicates a lack of cancer in the biological sample. In other embodiments, the present invention provides a method of diagnosing, identifying, classifying, or diagnosing cancer, e.g., thyroid cancer, comprising the steps of: obtaining an expression level for one or more gene products of a biological sample; and identifying the biological sample as malignant or suspicious wherein the gene product expression level(s) is indicative of a cancer in the biological sample. For example, this can be done by correlating the expression levels of the gene products in the biological sample with the expression levels of the same gene products in a control sample or a reference value, in order to identify (or rule out) the presence of thyroid cancer in the biological sample.

In particular embodiments, the present invention provides a method of diagnosing, identifying, or classifying a cancer, e.g., a thyroid cancer, in a subject, comprising the steps of: performing an assay to determine an expression level for one or more gene products of a biological sample, e.g., a thyroid tissue sample; and identifying the biological sample as benign wherein the gene product expression level(s) indicates a lack of cancer in the biological sample or identifying the biological sample as malignant or suspicious wherein the gene product expression level(s) is indicative of a cancer in the biological sample. In particular embodiments, the method comprises determining an expression level of two or more, or three or more, gene products in the thyroid tissue sample, wherein the two or more, or three or more, gene products are expressed by one or more genes listed in Table 1 and wherein at least one of the gene products is expressed by a CXCR3, CCR3, CXCL10, CAR, XB130, HO-1 or CCR7 gene. In certain embodiments, the method further comprises performing surgery, e.g., a thyroidectomy, on the subject if the biological sample if detemrined to be cancerous or malignant. In particular embodiments, the gene product is an RNA, and the assay comprises PCR, RT-PCR or quantitative PCR, or any other assay to measure RNA amounts or expression levels, including any of those assays described herein. In particular embodiments, the gene product is a polypeptide, and the assay comprises an immunohistochemistry assay or any other assay to measure polypeptide amounts or expression levels, including any of those described herein.

In particular embodiments, the present invention provides a method of diagnosing, identifying, or classifying a cancer, e.g., a thyroid cancer, in a subject, comprising the steps of: obtaining a biological sample, e.g., a thyroid tissue sample, from a subject; performing an assay to determine an expression level for one or more gene products in the biological sample; and identifying the biological sample as benign wherein the gene product expression level(s) indicates a lack of cancer in the biological sample or identifying the biological sample as malignant or suspicious wherein the gene product expression level(s) is indicative of a cancer in the biological sample. In particular embodiments, the method comprises determining an expression level of two or more, or three or more, gene products in the thyroid tissue sample, wherein the two or more, or three or more, gene products are expressed by one or more genes listed in Table 1 and wherein at least one of the gene products is expressed by a CXCR3, CCR3, CXCL10, CAR, XB130, HO-1 or CCR7 gene. In certain embodiments, the method further comprises performing surgery, e.g., a thyroidectomy, on the subject if the biological sample if detemrined to be cancerous or malignant. In particular embodiments, the gene product is an RNA, and the assay comprises PCR, RT-PCR or quantitative PCR, or any other assay to measure RNA amounts or expression levels, including any of those assays described herein. In particular embodiments, the gene product is a polypeptide, and the assay comprises an immunohistochemistry assay or any other assay to measure polypeptide amounts or expression levels, including any of those described herein.

As described further herein, in particular embodiments, the biological sample was obtained from a subject, e.g., a subject suspected of having or at risk of having a cancer. The gene products for which expression is determined include those described herein, and may comprise two or more gene products, which may also be referred to as a "set of gene products." The gene products described herein, which may be used to determine the presence or absence of cancer, e.g., thyroid cancer, may also be referred to as "biomarkers."

In particular embodiments, the present invention provides a method of detecting or diagnosing the presence or absence of thyroid cancer in a subject comprising determining an expression level of two or more, or three or more, gene products in a thyroid tissue sample obtained from the subject, wherein the two or more, or three or more, gene products are expressed by one or more genes listed in Table 1 and wherein at least one of the gene products is expressed by a CXCR3, CCR3, CXCL10, CAR, XB130, HO-1 or CCR7 gene; and identifying the thyroid tissue sample as cancerous or benign by correlating the expression levels determined for the biological sample from the subject with the presence or absence of thyroid cancer.

The present invention includes a method of treating a subject in need thereof, comprising performing a surgery, e.g., surgical removal of the subject's thyroid or a portion thereof (e.g., a thyroidectomy), on the subject, if the subject has been determined to have thyroid cancer, wherein the determination was made by any of the diagnostic methods of the present invention. In particular embodiments, a method of treating a subject in need thereof comprises performing a surgery, e.g., a thyroidectomy, on the subject, if the subject was determined to have a thyroid cancer by a method comprising the steps of: performing an assay to determine an expression level for one or more gene products of a biological sample, e.g., a thyroid tissue sample; and identifying the biological sample as benign wherein the gene product expression level(s) indicates a lack of cancer in the biological sample or identifying the biological sample as malignant or suspicious wherein the gene product expression level(s) is indicative of a cancer in the biological sample. In particular embodiments, the method comprised determining an expression level of two or more, or three or more, gene products in the thyroid tissue sample, wherein the two or more, or three or more, gene products are expressed by one or more genes listed in Table 1 and wherein at least one of the gene products is expressed by a CXCR3, CCR3, CXCL10, CAR, XB130, HO-1 or CCR7 gene. In particular embodiments, the method further comprises identifying the subject as being at risk of having thyroid cancer by perfoming a cytological or histochemical analysis of a biological samples obtained from the subject, e.g., by a needle biopsy or fine needle aspirate.

In related embodiments, the present invention includes a method of treating a subject in need thereof, comprising: determining if the subject has a cancer, e.g., thyroid cancer, by any of the diagnostic methods of the present invention; and performing a surgery, e.g., surgical removal of the subject's tumor or a portion thereof (e.g., a thyroidectomy), if the subject is determined to have a cancer, e.g., thyroid cancer. In particular embodiments, the method of treating a subject in need thereof comprises: (i) determining if the subject has a thyroid cancer by a method comprising the steps of: performing an assay to determine an expression level for one or more gene products of a biological sample, e.g., a thyroid tissue sample; and identifying the biological sample as benign wherein the gene product expression level(s) indicates a lack of cancer in the biological sample or identifying the biological sample as malignant or suspicious wherein the gene product expression level(s) is indicative of a cancer in the biological sample; and (ii) performing a surgery, e.g., a thyroidectomy, on the subject, if the results of step (i) indicate that the subject has or likely has a cancer, e.g., thyroid cancer. In particular embodiments, the method comprises determining an expression level of two or more, or three or more, gene products in the thyroid tissue sample, wherein the two or more, or three or more, gene products are expressed by one or more genes listed in Table 1 and wherein at least one of the gene products is expressed by a CXCR3, CCR3, CXCL10, CAR, XB130, HO-1 or CCR7 gene. In particular embodiments, the method further comprises identifying the subject as being at risk of having thyroid cancer by perfoming a cytological or histochemical analysis of a biological samples obtained from the subject, e.g., by a needle biopsy or fine needle aspirate.

In certain embodiments, the present invention includes a method of treating a subject in need thereof, comprising: (i) requesting, or obtaining the results of, a diagnostic assay described herein that was performed on a biological sample, e.g., a thyroid sample, obtained from the subject; and (ii) performing a surgery, e.g., surgical removal of the subject's tumor or a portion thereof (e.g., a thyroidectomy), if the results of the diagnostic assay indicate that the subject has a cancer, e.g., thyroid cancer. In particular embodiments, the diagnostic assay comprises: performing an assay to determine an expression level for one or more gene products of a biological sample, e.g., a thyroid tissue sample; and identifying the biological sample as benign wherein the gene product expression level(s) indicates a lack of cancer in the biological sample or identifying the biological sample as malignant or suspicious wherein the gene product expression level(s) is indicative of a cancer in the biological sample. In particular embodiments, the method comprises determining an expression level of two or more, or three or more, gene products in the thyroid tissue sample, wherein the two or more, or three or more, gene products are expressed by one or more genes listed in Table 1 and wherein at least one of the gene products is expressed by a CXCR3, CCR3, CXCL10, CAR, XB130, HO-1 or CCR7 gene. In particular embodiments, the method further comprises identifying the subject as being at risk of having thyroid cancer by requesting, or obtaining the results of, a cytological or histochemical analysis of a biological sample obtained from the subject, e.g., by a needle biopsy or fine needle aspirate.

In certain embodiments, the present invention includes a method of determining if a subject has a cancer, e.g., a thyroid cancer, where an initial test performed on a biological sample obtained from the subject, e.g., a FNA of thyroid tissue, was indeterminate, the method comprising performing, requesting, or obtaining the results of, a diagnostic assay described herein t performed on a biological sample, e.g., a thyroid sample, obtained from the subject. In particular embodiments, the diagnostic assay comprises: performing an assay to determine an expression level for one or more gene products of a biological sample, e.g., a thyroid tissue sample; and identifying the biological sample as benign wherein the gene product expression level(s) indicates a lack of cancer in the biological sample or identifying the biological sample as malignant or cancer wherein the gene product expression level(s) is indicative of a cancer in the biological sample. In particular embodiments, the method comprises determining an expression level of two or more, or three or more, gene products in the thyroid tissue sample, wherein the two or more, or three or more, gene products are expressed by one or more genes listed in Table 1 and wherein at least one of the gene products is expressed by a CXCR3, CCR3, CXCL10, CAR, XB130, HO-1 or CCR7 gene.

In particular embodiments of any of the methods of the invention, the correlating is performed by comparing the expression level(s) of the gene products in the sample from the subject to a control or reference expression level for each gene product examined. The thyroid tissue sample is identified as cancerous, if there is a significant difference in the expression level of the gene products between the thyroid tissue sample and normal control or reference expression levels. In certain embodiments, the thyroid tissue sample is identified as cancerous, if there is a significant difference in the expression level of two or more, three or more, or four or more gene products between the thyroid tissue sample and a normal control or reference expression levels. Likewise, the thyroid tissue sample is identified as benign, if there is no significant difference (i.e., there is substantial similarity) in the expression level of the gene products between the thyroid tissue sample and normal control or reference expression levels. In certain embodiments, the thyroid tissue sample is identified as benign, if there is no significant difference in the expression level of two or more, three or more, or four or more gene products between the thyroid tissue sample and a normal control or reference expression levels.

In certain embodiments of any of the methods described herein, the thyroid tissue sample is identified as cancerous, if the expression level of any one or more of Genes 1, 8, 9, 13, 14, 15 and/or 18 is decreased; and/or the expression level of any one or more of Genes 2, 3, 4, 5, 6, 7, 10, 11, 12, 16 and/or 17 is increased in the thyroid tissue sample as compared to the normal control expression level, wherein the total number of genes with increased or decreased expression is at least three. The identity of each gene is as follows: CXCR3 (Gene 1), CXCR3A (Gene 2), CXCR3B (Gene 3), CXCR4 (Gene 4), CCR3 (Gene 5), CXCL9 (Gene 6), CXCL10 (Gene 7), CXCL11 (Gene 8), SPAG-9 (Gene 9), CK-19 (Gene 10), TIMP-1 (Gene 11), CLDN-1 (Gene 12), CAR (Gene 13), Nectin-1 (Gene 14), XB-130 (Gene 15), HO-1 (Gene 16), CCR7 (Gene 17), and CXCL4 (Gene 18). In other embodiments of any of the methods described herein, a thyroid tissue sample is identified as cancerous, if the expression level of one or more, two or more, three or more, or four or more gene products of any of subsets of genes described herein is altered as described above. In particular embodiments, the gene set includes one or more of CXCR3, CCR3, CXCL10, CAR, X13130, 110-1 or CCR7.

In particular embodiments, the correlating is performed by comparing the expression levels of the gene products in the sample obtained from the subject to reference levels using an algorithm. The reference levels may include expression levels for each gene product previoulsy determined from a plurality of cancerous and/or non-cancerous biological samples.

In certain embodiments, the correlating comprises comparing the expression level to gene expression levels determined for the gene products for the following two sets of biological samples:
a plurality of normal thyroid tissue samples; and
a plurality of cancerous thyroid tissue samples,
wherein the thyroid tissue sample is identified as cancerous if there is a significant difference in the expression level of the gene products between the thyroid tissue sample and the gene expression levels for the plurality of normal thyroid tissue samples, or if there is substantially no difference in the gene expression level of the gene products between the thyroid tissue sample and the gene expression levels for the plurality of cancerous thyroid tissue samples.

In particular embodiments of any of the methods and kits of the present invention, the two or more or three or more gene products for which expression levels are determined comprise or consist of:
two or more or three or more gene products of the CXCR3, CCR3, CXCL10, CK19, TIMP-1, CLDN-1, CAR, XB130, HO-1 and CCR7 genes;
the gene products of the CXCR3, CCR3, CXCL10, CK19, TIMP-1, CLDN-1, CAR, HO-1 and CCR7 genes;
the gene products of the CCR3, TIMP-1, CAR and XB130 genes;
the gene products of the CXCL10, TIMP-1, CAR and CCR7 genes;
the gene products of the TIMP-1, CAR and CCR7 genes; or the gene products of the CXCL10, TIMP-1, CLDN-1, and CCR7 genes.

In particular embodiments of any of the above gene product sets, the two or more or three or more gene products include one or more of CXCR3, CCR3, CXCL10, CAR, XB130, 1-10-1 or CCR7. In particular embodiments, the gene products include one or more, two or more, or three or more of the genes listed in Table 1, and at least one of the gene products is expressed by a CXCR3 gene. In particular embodiments, the gene products include one or more, two or more, or three or more of the genes listed in Table 1, and at least one of the gene products is expressed by a CCR3 gene. In particular embodiments, the gene products include one or more, two or more, or three or more of the genes listed in Table 1, and at least one of the gene products is expressed by a CXCL10 gene. In particular embodiments, the gene products include one or more, two or more, or three or more of the genes listed in Table 1, and at least one of the gene products is expressed by a CAR gene. In particular embodiments, the gene products include one or more, two or more, or three or more of the genes listed in Table 1, and at least one of the gene products is expressed by a XB130 gene. In particular embodiments, the gene products include one or more, two or more, or three or more of the genes listed in Table 1, and at least one of the gene products is expressed by a HO-1 gene. In particular embodiments, the gene products include one or more, two or more, or three or more of the genes listed in Table 1, and at least one of the gene products is expressed by a CCR7 gene.

In various embodiments, methods of the present invention also include the step of performing a cytological or histological analysis on a biological sample, e.g., a thyroid tissue sample, obtained from the subject, e.g., to obtain a preliminary diagnosis. Cytological or histological analysis may be performed prior to, concurrent with, or subsequent to performing analysis based on expression of gene products, as described herein. In certain embodiments, samples with a preliminary diagnosis of intermediate or indeterminate are further analyzed by the methods of the present invention.

In particular embodiments of methods of the present invention, the methods further comprises obtaining a biological sample from the subject.

In certain embodiments of methods of the present invention, the methods further comprise treating the subject for thyroid cancer, if the patient is diagnosed as having thyroid cancer. In certain embodiments, the treatment comprises surgical removal of the subject's thyroid or a portion thereof.

The present invention also includes methods and kits useful for characterizing thyroid cancer. As used herein, the term "characterizing thyroid cancer" in a subject refers to the identification of one or more properties of a cancer sample in a subject, e.g., a specific type of thyoroid cancer, and may also include determining the subject's prognosis or survival. Cancers may be characterized by the identification of the expression of one or more markers, including but not limited to, the gene products disclosed herein. The skilled artisan will appreciate that the general methods described herein may be readily adapted to determine the type of thyroid cancer, e.g., by comparing the expression levels of the gene products to those determined for various types of thyroid cancer. Based on the determination of type of throid cancer, prognosis, survival, and/or likelihood of metastasis may be determined or estimated, e.g., based on historical data or outcomes.

Biological Samples

In certain embodiments, methods of the present invention utilize a biological sample obtained from a subject, and certain methods include obtaining a biological sample from a subject. A biological sample may be any material containing tissues, cells, nucleic acids, genes, gene fragments, expression products, gene products (e.g., mRNA or proteins), or gene product fragments of a subject to be tested. Methods for determining sample suitability and/or adequacy are provided. A sample may include but is not limited to, tissue, cells, or biological material from cells or derived from cells of an individual. The sample may be a heterogeneous or homogeneous population of cells or tissues. In certain embodiments, the biological sample is a tissue sample, e.g., a sample obtained from the thyroid or a thyroid nodule of a subject. A thyroid nodule is a growth in the thyroid gland. In particular embodiments, a biological sample comprises gene products, e.g., nucleic acids, such as mRNA, and/or proteins.

In various embodiments, the subject is an animal (e.g. a mammal), including but not limited to humans, non-human primates, rodents, dogs, cats, pigs, fish, and the like. In particular embodiments, the present methods and compositions apply to biological samples from humans. In some embodiments, the human is a child, an adolescent, or an adult. In particular embodiments, the subject has been determined to be at risk for having or is suspected of having a thyroid tumor.

The term "subject suspected of having" thyroid cancer refers to a subject that presents one or more symptoms indicative of a thyroid cancer (e.g., a noticeable lump or mass) or is being screened for a cancer (e.g., during a routine physical). For example, a subject may have been determined to have an enlarged thyroid and/or one or more thyroid nodules. A subject suspected of having thyroid carcinoma may also have one or more risk factors. A subject suspected of having thyroid cancer encompasses subjects who have received an initial diagnosis but for whom the stage of cancer is not known. The term further includes people who once had cancer (e.g., an individual in remission). In addition, certain subjects may have been previously tested for thyroid tumor but the results were inconclusive or indeterminate.

As used herein, the term "subject at risk for thyroid cancer" refers to a subject with one or more risk factors for developing thyroid cancer, in particular aggressive or metastatic thyroid cancer, more particularly ATC. Risk factors include, but are not limited to, gender, age, genetic predisposition, environmental exposure, previous incidents of cancer, preexisting non-cancer diseases, and lifestyle.

A biological sample may be obtained using any method known to the art that can provide a sample suitable for the analytical methods described herein. Methods of obtaining a biological sample from a subject include, but are not limited to, methods of biopsy including fine needle aspiration (FNA), needle aspiration, core needle biopsy, vacuum assisted biopsy, incisional biopsy, excisional biopsy, or punch biopsy. In particular embodiments, methods and kits of the present invention utilize biological samples obtained by FNA. Methods of obtaining suitable samples of thyroid are known in the art and are further described in the ATA Guidelines for thyroid nodule management (Cooper et al. Thyroid Vol. 16 No. 2 2006), herein incorporated by reference in its entirety. Generic methods for obtaining biological samples are also known in the art and further described in for example Ramzy, Ibrahim Clinical Cytopathology and Aspiration Biopsy 2001 which is herein incorporated by reference in its entirety. In one embodiment, the sample is a fine needle aspirate of a thyroid gland, a thyroid nodule or a suspected thyroid tumor. In some cases, the fine needle aspirate sampling procedure may be guided by the use of an ultrasound, X-ray, or other imaging device.

In some cases, multiple biological samples, such as multiple thyroid samples, may be obtained for diagnosis by the methods of the present invention, e.g., at the same or different times. In some cases, a sample, or samples obtained at the same or different times, are stored and/or analyzed by different methods. For example, a sample may be obtained and analyzed by cytological analysis (routine staining) In some cases, a further sample may be obtained from a subject at the same time or later, e.g., based on the results of a cytological analysis. The further sample may be used in a method of the present invention, e.g., when the cytological analysis was indeterminate with respect to the presence or absence of cancer. In other embodiments of methods of the present invention, a single sample may be obtained and a portion of the sample analyzed by cytological analysis, while another portion of the sample is analyzed by methods of the present invention.

In certain embodiments, a biological sample is obtained from a subject by a medical professional, e.g., at a hospital, doctor's office, testing center or laboratory. In certain embodiments, a biological sample may be obtained using a kit, which may contain a means for obtaining a sample as described herein, a means for storing the sample, and instructions for use of the kit. In some cases, the kit is provided by a molecular profiling service, which may also perform a diagnostic assay on the biological sample.

In particular embodiments, a biological sample is stored for a time such as seconds, minutes, hours, days, weeks, months, years or longer after the sample is obtained and before the sample is analyzed by one or more methods of the invention. In some cases, the sample obtained from a subject is subdivided prior to the step of storage or further analysis such that different portions of the sample are subject to different downstream methods or processes including but not limited to storage, cytological analysis, adequacy tests, nucleic acid extraction, protein extraction, molecular profiling or a combination thereof. In some cases, a portion of the sample is stored while another portion of said sample is further manipulated. Such manipulations may include but are not limited to: molecular profiling; cytological staining; nucleic acid (e.g., mRNA) extraction, detection, or quantification; protein extraction, detection, or quantification; fixation (e.g. formalin fixed paraffin embedded samples); and/or examination. The sample may be fixed prior to or during storage by any method known to the art such as using glutaraldehyde, formaldehyde, or methanol. In other cases, the sample is obtained and stored and subdivided after the step of storage for further analysis such that different portions of the sample are subject to different downstream methods or processes including but not limited to storage, cytological analysis, adequacy tests, nucleic acid extraction, polypeptide extraction, molecular profiling, determining expression of one or more gene products, or a combination thereof. In some cases, samples are obtained and analyzed by, for example cytological analysis, and the resulting sample material is further analyzed by one or more methods of the present invention comprising determining expression levels of gene products described herein, e.g., by molecular profiling. In such cases, the samples may be stored between the steps of cytological analysis and the steps of determining gene product expression levels, e.g., by molecular profiling. In certain embodiments, samples may be stored frozen (e.g., at about any of 0° C., −1° C., −2° C., −3° C., −4° C., −5° C., −6° C., −7° C., −8° C., −9° C., −10° C., −12° C., −14° C., −15° C., −16° C., −20° C., −22° C., −25° C., −28° C., −30° C., −35° C., −40° C., −45° C., −50° C., −60° C., −70° C., −80° C., −100° C., −120° C., −140° C., −180° C., −190° C., or about −200° C.) or at reduced temperatures (e.g. between about 20° C. and about 0° C.) in a suitable medium, excipient, or solution, such as, e.g., a commercial preparation suitable for storage of cells for subsequent cytological analysis, such as but not limited to, Cytyc ThinPrep, SurePath, or Monoprep.

During or after sample obtainment, including before or after a step of storing the sample, the biological sample may assessed for its suitability for use in the methods and compositions of the present invention. The sample may be determined to be adequate or inadequate for further analysis due to many factors including but not limited to: insufficient cells, insufficient genetic material, insufficient protein, DNA, or RNA, inappropriate cells for the indicated test, or inappropriate material for the indicated test, age of the sample, manner in which the sample was obtained, or manner in which the sample was stored or transported. Adequacy may be determined using a variety of methods known in the art such as a cell staining procedure, measurement of the number of cells or amount of tissue, measurement of total protein, measurement of nucleic acid, visual examination, microscopic examination, or temperature or pH determination. In one embodiment, sample adequacy is determined from the results of performing a gene product level analysis experiment.

Examples of methods for determining that an adequate number of a specific type of cell is present include PCR, quantitative PCR, RT-PCR, immuno-histochemical analysis, cytological analysis, microscopic, and or visual analysis.

Samples may be analyzed by determining nucleic acid content after extraction from the biological sample using a variety of methods known to the art, such as, e.g., ultraviolet absorbance, including but not limited to aborbance at 260 nanometers using a spectrophotometer. In certain embodiments, the RNA quantity or yield from a given sample is measured using a NanoDrop spectrophotometer in a range of nano- to micrograms. In some embodiments, RNA quality is measured using an Agilent 2100 Bioanalyzer instrument, and is characterized by a calculated RNA Integrity Number (RIN, 1-10). The RNA integrity number (RIN) is an algorithm for assigning integrity values to RNA measurements. The RIN algorithm is applied to electrophoretic RNA measurements and based on a combination of different features that contribute information about the RNA integrity to provide a more robust universal measure. The algorithm assigns a 1 to 10 RIN score, where level 10 RNA is highest quality. In one aspect, the present invention provides a method of analyzing gene expression from a sample with an RNA RIN value equal or less than 6.0, equal or less than 5, or equal or less than 4. In some embodiments, a sample containing RNA with an RIN number of about any of 1.0, 2.0, 3.0, 4.0, 5.0 or 6.0 is analyzed using the subject methods and algorithms of the present invention.

In some embodiments, protein content in the biological sample is measured using any of a variety of methods known to the art, including but not limited to: ultraviolet absorbance at 280 nanometers, cell staining, or protein staining with, for example, coomassie blue, or bichichonic acid. In some cases, protein is extracted from the biological sample prior to measurement of the sample.

In particular embodiments, samples are processed by any method known and available in the art, e.g., to isolate gene products from the biological sample. In certain embodiments, the gene products are selected from nucleic acids (e.g., RNA, including mRNA) and proteins.

Cytological Analysis

Cytological analysis of biological samples may be performed, e.g., by cell staining combined with microscopic examination of the cells in the biological sample. Cell staining, or cytological examination, may be performed by a number of methods and suitable reagents known to the art including but not limited to: EA stains, hematoxylin stains, cytostain, Papanicolaou stain, eosin, nissl stain, toluidine blue, silver stain, azocarmine stain, neutral red, or j anus green. In some cases the cells are fixed and/or permeablized, e.g., using methanol, ethanol, glutaraldehyde or formaldehyde, prior to or during the staining procedure, while in others, they are not. Nucleic acid content may or may not be performed, e.g., using a staining procedure, for example with ethidium bromide, hematoxylin, nissl stain or any nucleic acid stain known to the art.

In some embodiments, cells may be smeared onto a slide by standard methods well known in the art for cytological examination. In other cases, liquid based cytology (LBC) methods may be utilized. In LBC methods, biological samples are transferred from the subject to a container or vial containing a liquid cytology preparation solution such as for example Cytyc ThinPrep, SurePath, or Monoprep or any other liquid based cytology preparation solution known in the art. Additionally, the sample may be rinsed from the collection device with liquid cytology preparation solution into the container or vial to ensure substantially quantitative transfer of the sample. The solution containing the biological sample in liquid based cytology preparation solution may then be stored and/or processed by a machine or by one skilled in the art to produce a layer of cells on a glass slide. The sample may further be stained and examined under the microscope in the same way as a conventional cytological preparation.

In some embodiments, samples may be analyzed by immuno-histochemical staining Immuno-histochemical staining provides for the analysis of the presence, location, and distribution of specific molecules or antigens by use of antibodies in a biological sample (e.g. cells or tissues). Antigens may be small molecules, proteins, peptides, nucleic acids or any other molecule capable of being specifically recognized by an antibody. Samples may be analyzed by immuno-histochemical methods with or without a prior fixing and/or permeabilization step. In some cases, the antigen of interest may be detected by contacting the sample with an antibody specific for the antigen and then non-specific binding may be removed by one or more washes. The specifically bound antibodies may then be detected by an antibody detection reagent such as for example a labeled secondary antibody, or a labeled avidin/streptavidin. In some cases, the antigen specific antibody may be labeled directly instead. Suitable labels for immunohistochemistry include but are not limited to fluorophores such as fluoroscein and rhodamine, enzymes such as alkaline phosphatase and horse radish peroxidase, and radionuclides such as $^{32}P$ and $^{125}I$. Examples of Gene product markers that may be detected by immuno-histochemical staining include but are not limited to Her2/Neu, Ras, Rho, EGFR, VEGFR, UbcHIO, RET/PTC1, cytokeratin 20, calcitonin, GAL-3, thyroid peroxidase, and thyroglobulin.

The results of routine cytological examination may indicate a biological sample as negative (cancer free), ambiguous or suspicious (suggestive of the presence of a cancer), diagnostic (positive diagnosis for a cancer), or non-diagnostic or indeterminate (providing inadequate information concerning the presence or absence of cancer). The diagnostic results may be classified as malignant or benign. In some cases, the diagnostic results may be indicative of a particular type of a cancer or condition, such as any of the diseases or conditions described herein.

Genes and Gene Products

In various embodiments, methods of the present invention include molecular profiling of a biological sample, eg., by determining expression levels of gene products expressed by any of the genes or gene sets identified herein. Gene products include, but are not limited to, mRNA and protein expressed from the gene. Gene products (also referred to as "gene expression products") for which expression levels are determined, measured or analyzed according to methods of the present invention comprise or consist of gene products expressed by one or more, two or more, three or more, or four or more gene set forth in Table 1, as well as variants or homologs thereof (i.e., the corresponding genes from other species). The gene products for which expression is determined may be exclusively gene products expressed by genes in Table 1 (or variants or homologs thereof), or they may include one or more additional gene products, including any previously linked to thyroid cancer and those described, e.g., in PCT patent applications WO2011/032296, WO2011/143361, or WO2010/056374. Table 1 provides names and accession numbers for illustrative sequences for the human genes. Corresponding genes from other species are readily available.

TABLE 1

Genes

| Genes | Full Name | OTHER NAMES | Accesion Number RefSeq | |
|---|---|---|---|---|
| | | | Polynucleotide | Polypeptide |
| CXCR3 (Gene 1) | chemokine (C-X-C motif) receptor 3 | G protein-coupled receptor 9 (GPR9) and CD183 | NM_001504.1 (SEQ ID NO: 1) | NP_001495.1 (SEQ ID: NO: 2) |
| CCR3 (Gene 5) | chemokine (C-C motif) receptor 3 | CD193 (cluster of differentiation 193) | NM_001837.3 (SEQ ID NO: 3) | NP_001828.1 (SEQ ID NO: 4) |
| CXCL10 (Gene 7) | chemokine (C-X-C motif) ligand 10 | Interferon gamma-induced protein 10 (IP-10) or small-inducible cytokine B10 | NM_001565 (SEQ ID NO: 5) | NP_001556.2 (SEQ ID NO: 6) |
| CK19 (Gene 10) | citokeratin 19 | Keratin, type I cytoskeletal 19 or keratin-19 (K19) | NM_002276.4 (SEQ ID NO: 7) | NP_002267.2 (SEQ ID NO: 8) |
| TIMP-1 (Gene 11) | Tissue Inhibitor of Metalloproteinase-1 | TIMP metallopeptidase inhibitor 1 | NM_003254 (SEQ ID NO: 9) | NP_003245.1 (SEQ ID NO: 10) |
| CLDN-1 (Gene 12) | claudin 1 | | NM_021101.4 (SEQ ID NO: 11) | NP_066924.1 SEQ ID NO: 12) |
| CAR (Gene 13) | coxsackie virus and adenovirus receptor | CXADR | NM_001207066.1 (SEQ ID NO: 13) | NP_001193995.1 SEQ ID NO: 14) |
| XB-130 (Gene 15) | actin filament associated protein 1-like 2 | AFAP1L2 | NM_001001936.1 (SEQ ID NO: 15) | NP_001001936.1 (SEQ ID NO: 16) |
| HO-1 (Gene 16) | heme oxygenase (decycling) 1 | HMOX1 (heme oxygenase (decycling) 1) | NM_002133.2 (SEQ ID NO: 17) | NP_002124.1 SEQ ID NO: 18) |
| CCR7 (Gene 17) | chemokine (C-C motif) receptor 7 | C-C chemokine receptor type 7 or CD197 | NM_001838.3 (SEQ ID NO: 19) | NP_001829.1 (SEQ ID NO: 20) |

In particular embodiments, methods of the present invention comprise determining an expression level of gene products of two or more, three or more, four or more, or five or more of the genes shown in Table 1 in a biological sample, e.g., a thyroid tissue sample. In certain embodiments, the method comprises determining an expression level of gene products of at least one, at least two, or at least three genes selected from the CXCR3, CCR3, CXCL10, CAR, XB130, HO-1 and CCR7 genes. In one embodiment, expression levels are determined for gene products comprising or consisting of gene products of the CXCR3, CCR3, CXCL10, CK19, TIMP-1, CLDN-1, CAR, HO-1 and CCR7 genes. In other embodiments, expression levels are determined for gene products comprising or consisting of: gene products of the CCR3, TIMP-1, CAR and XB130 genes; gene products of the CXCL10, TIMP-1, CAR and CCR7 genes; gene products of the TIMP-1, CAR and CCR7 genes; or gene products of the CXCL10, TIMP-1, CLDN-1, and CCR7 genes. The particular sets of gene products for which expression is determined may be referred to as a "set" of gene products, and the particular genes for which expression is determined may be referred to as a "gene set." In certain embodiments, the expression level of the same type of gene product, e.g., mRNA or protein, is determined for each gene set utilized according to a method of the present invention. Thus, in particular embodiments, the expression level of only one type of gene product, e.g., mRNA or protein, is determined in practicing a method of the present invention on a particular tissue sample. Nonetheless, it is contemplated that methods of the present invention may be practiced wherein the expression levels of two or more different types of gene products, e.g., both mRNA and protein, are determined for each gene of a gene set being utilized.

Measuring Levels of Gene Products

The expression level of gene products may be determined by any suitable means available in the art, and will depend primarily upon the type of gene product being measured. For example, reagents for detecting gene products may measure RNA expression, protein expression, protein activity or downstream biological functions of the protein encoded by genes described herein. Thus, the present invention includes reagents for detecting such genes or the gene products thereof, including nucleic acids, DNA probes, or antibodies that bind to the encoded proteins, and the like.

Protein expression levels may be determined, e.g., by immunohistochemistry using antibodies that specifically bind to protein gene products. In certain embodiments, protein expression levels are determined using a polypeptide array or an antibody array. Certain embodiments may employ standard methodologies and detectors such as western blotting and immunoprecipitation, enzyme-linked immunosorbent assays (ELISA), flow cytometry, and immunofluorescence assays (IFA), which utilize an imaging device. These well-known methods typically utilize one or more monoclonal or polyclonal antibodies, or fragments thereof, that specifically bind to a selected target polypeptide gene product of the invention, or a unique region of that polypeptide, and generally do not bind significantly to other polypeptides. An antibody, or antigen-binding fragment thereof, is said to "specifically bind," "immunologically bind," and/or is "immunologically reactive" to a polypeptide of the invention if it reacts at a detectable level (within, for example, an ELISA assay) with the polypeptide, and does not react detectably in a statistically significant manner with unrelated polypeptides under similar conditions.

Certain embodiments may employ "arrays," such as "microarrays." In certain embodiments, a "microarray" may also refer to a "peptide microarray" or "protein microarray" having a substrate-bound collection or plurality of polypeptides, the binding to each of the plurality of bound polypeptides being separately detectable. Alternatively, the peptide microarray may have a plurality of binders, including but not limited to monoclonal antibodies, polyclonal antibodies, phage display binders, yeast 2 hybrid binders, and aptamers, which can specifically detect the binding of the polypeptide gene products described herein. The array may be based on autoantibody detection of polypeptides, as described, for example, in Robinson et al., Nature Medicine 8(3):295-301 (2002). Examples of peptide arrays may be found in WO 02/31463, WO 02/25288, WO 01/94946, WO 01/88162, WO 01/68671, WO 01/57259, WO 00/61806, WO 00/54046, WO 00/47774, WO 99/40434, WO 99/39210, and WO 97/42507 and U.S. Pat. Nos. 6,268,210, 5,766,960, and 5,143,854, each of which are incorporated by reference.

Certain embodiments may employ mass spectrometry (MS) or other molecular weight-based methods for diagnostically detecting polypeptide gene products. MS refers generally to an analytical technique for determining the elemental composition of a sample or molecule. MS may also be used for determining the chemical structures of molecules, such as peptides and other chemical compounds. An illustrative MS instruments has three modules: an ion source, which converts gas phase sample molecules into ions (or, in the case of electrospray ionization, move ions that exist in solution into the gas phase); a mass analyzer, which sorts the ions by their masses by applying electromagnetic fields; and a detector, which measures the value of an indicator quantity and thus provides data for calculating the abundances of each ion present. The MS technique has both qualitative and quantitative uses, including quantifying the amount of a polypeptide gene product in a sample. Included are gas chromatography-mass spectrometry (GC/MS or GC-MS), liquid chromatography mass spectrometry (LC/MS or LC-MS), and ion mobility spectrometry/mass spectrometry (IMS/MS or IMMS). Accordingly, MS techniques may be used according to any of the methods provided herein to measure the levels of polypeptide gene product in a sample, and, optionally, to compare those levels to a control sample or a pre-determined value.

Certain embodiments may employ cell-sorting or cell visualization or imaging devices/techniques to detect or quantitate the presence or levels of gene products in a sample. Examples include flow cytometry or FACS, immunofluorescence analysis (IFA), and in situ hybridization techniques, such as fluorescent in situ hybridization (FISH).

In certain embodiments, methods of the invention include a step of detecting a polypeptide gene product or determining or measuring an amount of a polypeptide gene product that comprises contacting the biological sample with one or more probes (e.g., polypeptides or antibodies) that bind to the polypeptide gene product under conditions and for a time sufficient for such binding to occur, and then detecting an amount of polypeptide gene product that is bound to the probe(s), e.g., an amount of the complex of probe and polypeptide gene product. The detection may be performed by any of a variety of methods known in the art and may employ the use of detectable labels, e.g., immunofluorescent moieties. In certain embodiments, the probe is detectably labeled. In certain embodiments, the bound polypeptide gene product is detected in solution or on a solid support.

Methods of the invention may include a step of isolating one or more gene products from a biological sample, e.g., before or during determining the amount of particular gene products in the sample. In certain embodiments, the gene products being detected are polypeptides, and polypeptides are purified or partially purified from the biological sample. In certain embodiments, the gene products being detected are mRNAs, and polynucleotides or mRNAs are purified or partially purified from the biological sample. Methods of purifying or partially purifying polypeptides or polynucleotides from a biological sample are known in the art.

Nucleic acid expresion levels may be determined using a variety of different assays, including but not limited to amplification assays and hybridization assays. Amplification assays useful in the present invention include, but are not limited to, polymerase chain reaction (PCR) assays, including reverse transcriptase-PCR (RT-PCR) and real-time PCR, and isothermal amplification methods. Hybridization assays include, but are not limited to, Northern blot, quantitative or qualitative polymerase chain reaction (PCR), quantitative or qualitative reverse transcriptase PCR (RT-PCR), microarray, dot or slot blots, and in situ hybridization such as fluorescent in situ hybridization (FISH).

Certain embodiments may employ hybridization methods for measuring expression of a polynucleotide gene product, such as mRNA. Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, PNAS. 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

Certain embodiments may employ molecular bar-coding techniques, such as commercially available from NanoString Technologies Inc (Seattle, Wash., USA) under the brand name nCounter Gene Expression Assay. This technology allows target expression levels to be directly assayed from samples as complex as tissue lysates without the need for transcript amplification. In this method, a biotinylated capture probe and a bar-coded reporter probe (color coded) are specifically hybridized directly to a target gene of interest. Following removal of excess unbound probe, probe/target complexes are immobilized and aligned on nCounter cartridges, and then digital images are acquired and quantified, each bar-code count representing a transcript copy of the corresponding target gene. Importantly, the use of this bar-coding method allows for multiplex detection of more than 500 genes in a single sample reaction with very high reproducibility.

Certain embodiments may measure RNA expression using the transcript analysis and affinity capture (TRAC) method, wherein multiplexed detection of expressed RNA species can be performed directly on cell lysates or on purified total RNA samples, without the need for any reverse transcription or amplification. In this novel procedure, biotinylated oligo-dT and dual-fluorophore-labled gene-specific probes, each probe of distinctly different size, are hybridized to mRNAs in a given sample. The hybridized material is bound to magnetic streptavidin beads, washed, released, and then resolved via capillary electrophoresis. Thus target identification and quantification is achieved simultaneously by analyzing the probe/target size and fluorescence profiles.

Certain embodiments may employ quantitative nuclease protection assays (qNPA) or qNPA microarrays, such as those available commercially from High Throughput Genomics Molecular Diagnostics Inc (Tucson, Ariz., USA), wherein the hybridization of gene specific probes to expressed RNAs protects transcript/probe complexes from digestion by the single-strand-specific 51 ribonuclease. Following 51 treatment and base-mediated probe/target complex dissociation, the remaining probes exist in a 1:1 stoichiometry to their corresponding target sequences, and thus quantification of probes via capture on microarray surfaces allows inference of the corresponding target sequence expression levels.

Certain embodiments may employ nucleic acid amplification methods for detecting gene products. The term "amplification" or "nucleic acid amplification" refers to the production of multiple copies of at least a portion of a target nucleic acid sequence. The multiple copies may be referred to as amplicons or amplification products. "Selective amplification" or "specific amplification," as used herein, refers to the amplification of a target nucleic acid sequence according to the present invention wherein detectable amplification of the target sequence is substantially limited to amplification of target sequence contributed by a nucleic acid sample of interest that is being tested and is not contributed by target nucleic acid sequence contributed by some other sample source, e.g., contamination present in reagents used during amplification reactions or in the environment in which amplification reactions are performed.

The term "amplification conditions" refers to conditions permitting nucleic acid amplification according to the present invention. Oligonucleotides used in the amplification reactions of the present invention hybridize to their intended targets under amplification conditions. Acceptable conditions to carry out nucleic acid amplifications according to the present invention can be easily ascertained by someone having ordinary skill in the art depending on the particular method of amplification employed.

Many well-known methods of nucleic acid amplification require thermocycling to alternately denature double-stranded nucleic acids and hybridize primers; however, other well-known methods of nucleic acid amplification are isothermal. The polymerase chain reaction (U.S. Pat. Nos. 4,683,195; 4,683,202; 4,800,159; 4,965,188), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA.

As noted above, the term "PCR" refers to multiple amplification cycles that selectively amplify a target nucleic acid species. Included are quantitative PCR (qPCR), real-time PCR), reverse transcription PCR (RT-PCR) and quantitative reverse transcription PCR (qRT-PCR) is well described in the art. The term "qPCR" refers to quantitative polymerase chain reaction, and the term "qRT-PCR" refers to quantitative reverse transcription polymerase chain reaction. qPCR and qRT-PCR may be used to amplify and simultaneously quantify a targeted cDNA molecule. It enables both detection and quantification of a specific sequence in a cDNA pool. Amplification products can then be visualized by a variety of means, e.g., directly in a gel by staining, the product can be detected by hybridization with a detectable probe, and/or by using next generation sequencing.

"Real-time PCR" may use DNA-binding dye to bind to double-stranded (ds) DNA in PCR reaction mix, causing fluorescence of the dye. An increase in DNA product during PCR thus leads to an increase in fluorescence intensity and is measured at each cycle, thus allowing DNA concentrations to be quantified. dsDNA dyes such as SYBR Green will bind to all dsDNA PCR products. Certain embodiments may use Taqman probes, which are labeled at the 5' end with a fluorophore and at the 3' end with a quencher and are designed to anneal between the forward and reverse primer binding sites of a desired amplicon. As long as the quencher is kept in close proximity to the fluorophore, no fluorescence is emitted. During a cycle of PCR, however, as the polymerase extends the primers the fluorphore and quencher of a bound probe are cleaved off by means of the polymerase's 5'-3' exonuclease activity, and fluorescence is emitted. Thus the amount of transcript present in the sample is directly proportional to the amount of fluorescence detected, and increases in transcript number following PCR cycles lead to a corresponding increase in emitted fluorescence. Fluorescence is detected and measured in the real-time PCR thermocycler, and its geometric increase corresponding to exponential increase of the product is used to determine the threshold cycle ("Ct") in each reaction.

The term "Ct Score" refers to the threshold cycle number, which is the cycle at which PCR amplification has surpassed a threshold level. If there is a higher quantity of mRNA for a particular gene in a sample, it will cross the threshold earlier than a lowly expressed gene since there is more starting RNA to amplify. Therefore, a low Ct score indicates high gene expression in a sample and a high Ct score is indicative of low gene expression. An atypical CT value is a value that is greater than two standard deviations of the average CT value for a given gene.

In certain embodiments, said amplification methods may employ PCR-based multiplexing, defined herein as the process of detecting two or more target sequences in a single reaction. Other embodiments of said amplification methods may employ microfluidics to control the thermocycling process, or to precisely control the amount and timing of reagents added, or in other embodiments to allow the adaptation of said amplification methods to portable kits suitable for clinical application of said methods in lieu of personalized diagnostics.

Certain embodiments may employ amplification-based detection methods in an array format, for example such as those offered commercially by Qiagen (Hilden, Germany) under the brand name RT² Profiler PCR Array, or by Lonza (Basel, Switzerland) under the brand name StellARray, or by Life Technologies (Carlsbad, Calif., USA) under the brand name OpenArray. In these approaches, independent qPCR reactions can be run simultaneously in high density 96-well plates, 384-well plates, 100-well discs, or 48 well chips, allowing quantification of standard or custom gene sets with all of the benefits of qPCR and the added advantage of high throughput.

Certain embodiments may employ the ligase chain reaction (Weiss, Science. 254: 1292, 1991), commonly referred to as LCR, which uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Another method is strand displacement amplification (Walker, G. et al., 1992, *Proc. Natl. Acad. Sci. USA* 89:392-396; U.S. Pat. Nos. 5,270,184 and 5,455,166), commonly referred to as SDA, which uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315).

Other amplification methods include, for example: nucleic acid sequence based amplification (U.S. Pat. No. 5,130,238), commonly referred to as NASBA; one that uses an RNA replicase to amplify the probe molecule itself (Lizardi, P. et al., 1988, *BioTechnol*. 6: 1197-1202), commonly referred to as Qβ replicase; a transcription based amplification method (Kwoh, D. et al., 1989, *Proc. Natl. Acad. Sci. USA* 86:1173-1177); self-sustained sequence replication (Guatelli, J. et al., 1990, *Proc. Natl. Acad. Sci. USA* 87: 1874-1878); and, transcription mediated amplification (U.S. Pat. Nos. 5,480,784 and 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, DC).

Illustrative transcription-based amplification systems that may be used according to the present invention include transcription mediated amplification (TMA), which employs an RNA polymerase to produce multiple RNA transcripts of a target region (U.S. Pat. Nos. 5,480,784 and 5,399,491). TMA uses a "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNase H activity to digest the RNA strand of an RNA:DNA hybrid, thereby making the DNA strand available for hybridization with a primer or promoter-primer. Generally, the RNase H activity associated with the reverse transcriptase provided for amplification is used.

In certain embodiments, other techniques may be used to determine expression of a polynucleotide gene product, including microarray analysis (Han, M., et al., *Nat Biotechnol*, 19: 631-635, 2001; Bao, P., et al., *Anal Chem*, 74: 1792-1797, 2002; Schena et al., *Proc. Natl. Acad. Sci*. USA 93:10614-19, 1996; and Heller et al., *Proc. Natl. Acad. Sci*. USA 94:2150-55, 1997) and SAGE (serial analysis of gene expression). Like MPSS, SAGE is digital and can generate a large number of signature sequences. (see e.g., Velculescu, V. E., et al., *Trends Genet*, 16: 423-425., 2000; Tuteja R. and Tuteja N. *Bioessays*. 2004 Aug.; 26(8):916-22), although orders of magnitude fewer than that are available from techniques such as MPSS.

In certain embodiments, the term "microarray" includes a "nucleic acid microarray" having a substrate-bound plurality of nucleic acids, hybridization to each of the plurality of bound nucleic acids being separately detectable. The substrate can be solid or porous, planar or non-planar, unitary or distributed. Nucleic acid microarrays include all the devices so called in Schena (ed.), DNA Microarrays: A Practical Approach (Practical Approach Series), Oxford University Press (1999); Nature Genet. 21(1) (suppl.): 1-60 (1999); Schena (ed.), Microarray Biochip: Tools and Technology, Eaton Publishing Company/BioTechniques Books Division (2000). Nucleic acid microarrays may include a substrate-bound plurality of nucleic acids in which the plurality of nucleic acids are disposed on a plurality of beads, rather than on a unitary planar substrate, as described, for example, in Brenner et al., Proc. Natl. Acad. Sci. USA 97(4): 1665-1670 (2000). Examples of nucleic acid microarrays may be found in U.S. Pat. Nos. 6,391,623, 6,383,754, 6,383,749, 6,380, 377, 6,379,897, 6,376,191, 6,372,431, 6,351,712 6,344,316, 6,316,193, 6,312,906, 6,309,828, 6,309,824, 6,306,643, 6,300,063, 6,287,850, 6,284,497, 6,284,465, 6,280,954, 6,262,216, 6,251,601, 6,245,518, 6,263,287, 6,251,601, 6,238,866, 6,228,575, 6,214,587, 6,203,989, 6,171,797, 6,103,474, 6,083,726, 6,054,274, 6,040,138, 6,083,726, 6,004,755, 6,001,309, 5,958,342, 5,952,180, 5,936,731, 5,843,655, 5,814,454, 5,837,196, 5,436,327, 5,412,087, and 5,405,783, the disclosures of which are incorporated by reference.

Additional examples include nucleic acid arrays that are commercially available from Affymetrix (Santa Clara, Calif.) under the brand name GENECHIP™ or Illumina (San Diego, Calif.). Further exemplary methods of manufacturing and using arrays are provided in, for example, U.S. Pat. Nos. 7,028,629; 7,011,949; 7,011,945; 6,936,419; 6,927,032; 6,924,103; 6,921,642; and 6,818,394.

The present invention as related to arrays and microarrays also contemplates many uses for polymers attached to solid substrates. Exemplary gene expression monitoring and profiling methods and methods useful for gene expression monitoring and profiling are descrived in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Application No. 2003/0036069), and U.S. Pat. Nos. 5,925, 525, 6,268,141, 5,856,092, 6,267,152, 6,300,063, 6,525,185, 6,632,611, 5,858,659, 6,284,460, 6,361,947, 6,368,799, 6,673,579 and 6,333,179. Other methods of nucleic acid amplification, labeling and analysis that may be used in combination with the methods disclosed herein are embodied in U.S. Pat. Nos. 5,871,928, 5,902,723, 6,045,996, 5,541,061, and 6,197,506.

Certain embodiments may employ RNA sequencing, such as Whole Transcriptome Shotgun Sequencing (WTSS), commonly referred to as RNA-Seq, for the analysis of RNA expression, wherein a transcriptome map of expression profiles with single nt-resolution can be assembled via the utilization of deep sequencing technologies. In one embodiment, RNA samples, e.g. mRNA, are converted to fragmented cDNAs and then ligated to sequencing adaptors. High throughput sequencing allows the generation of millions of short sequence reads which can be either assembled de novo, or aligned against a known genome or reference sequence. The ratio of the individual sequence reads to the total number of recorded reads can then be used to generate an expression profile.

In certain embodiments, methods of the invention include a step of detecting a polynucleotide gene product (e.g., mRNA) or determining or measuring an amount of a polynucleotide gene product that comprises contacting the biological sample with one or more probes (e.g., primers or polynuclotides) that bind to the polynuclotide gene product under conditions and for a time sufficient for such binding to occur, and then detecting an amount of polynucleotide gene product that is bound to the probe(s), e.g., an amount of the complex of probe and polynucleotide gene product. The detection may be performed by any of a variety of methods known in the art and may employ the use of detectable labels, e.g., immunofluorescent moieties. In certain embodiments, the probe is detectably labeled. In certain embodiments, the bound polynucleotide gene product is detected in solution or on a solid support.

Reagents for Detecting Gene Products

As will be apparent to persons skilled in the art, certain embodiments may employ reagents for detecting gene products, such as, e.g., antibodies and oligonucleotides, including primers or probes, as described herein. In particular embodiments, a reagent for detecting a gene product specifically binds or specifically hybridizes to the target gene product and not to unrelated gene products, e.g., gene products expressed from a different, unrelated gene. Methods of producing reagents, such as antibodies and oligonucleotides, that specifically bind or specifically hybridize to a target polypeptide or nucleic acid sequence are known in the art. For example, antibodies may be prepared by any of a variety of techniques known to those of ordinary skill in the art. See, e.g., Harlow and Lane, *Antibodies: A Laboratory Manual*, Cold Spring Harbor Laboratory, 1988. Monoclonal antibodies specific for a polypeptide of interest may be prepared, for example, using the technique of Kohler and Milstein, *Eur. J. Immunol.* 6:511-519, 1976, and improvements thereto.

With respect to single stranded nucleic acids, particularly oligonucleotides, the term "specifically hybridize" refers to the association between two single-stranded nucleotide molecules of sufficient complementary sequence to permit such hybridization under pre-determined conditions generally used in the art (sometimes termed "substantially complementary"). In particular, in one embodiment the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence. For example, specific hybridization can refer to a sequence which hybridizes to a gene product under appropriate conditions enabling specific hybridization of single stranded nucleic acid molecules of varying complementarity are well known in the art.

In one embodiment, the expression level of a gene product in a biological sample is determined by measuring the relative rates of transcription of RNA, such as by production of corresponding cDNAs and then analyzing the resulting DNA using probes, such as, e.g., those developed from the gene sequences as identified in Table 1. Accordingly, the levels of cDNA produced by use of reverse transcriptase with the RNA of a biological sample produces a corresponding amount of cDNA, which can then be amplified using polymerase chain reaction, or some other means, to determine the relative levels of resulting cDNA and, thereby, the relative levels of gene expression.

Illustrative reagents for detecting nucleic acid gene products include nucleic acids, and in particular include oligonucleotides. A nucleic acid can be DNA or RNA, and may be single or double stranded. In one embodiment, the oligonucleotides are DNA probes, or primers for amplifying nucleic acids produced from target genes. In one embodiment, the oligonucleotides of the present invention are capable of specifically hybridizing (e.g., under moderate or stringent hybridization conditions), to a gene product described herein. Oligonucleotides can be naturally occurring or synthetic, but are typically prepared by synthetic means. Oligonucleotides, as described herein, may include segments of DNA, or their complements. The exact size of the oligonucleotide will depend on various factors and on the particular application and use of the oligonucleotide. Oligonucleotides, which include probes and primers, can be any length from 3 nucleotides to the full length of a target gene product (such as those expressed from the gene provided in Table 1), and explicitly include every possible number of contiguous nucleic acids from 3 through the full length of a target gene product. Thus, oligonucleotides can be between 5 and 100 contiguous bases, and often range from 5, 10, 12, 13, 14, 15, 16, 17, 18, 19, 20, 21, 22, 23, 24, or 25 nucleotides to 30, 35, 40, 45, 50, 55, 60, 65, 70, 75, 80, 85, 90, 95, or 100 nucleotides. Oligonucleotides between 5-10, 5-20, 10-20, 12-30, 15-30, 10-50, 20-50 or 20-100 bases in length are common.

Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention (e.g., the expressed gene products or resulting cDNAs or copies thereof resulting from amplification). The present invention includes oligonucleotides that can be used as, for example, probes to identify nucleic acid molecules (e.g., DNA probes) or primers to amplify nucleic acid molecules.

In one embodiment, an oligonucleotide may be a probe which refers to, e.g., an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. In certain embodiments, a probe can be between 5 and 100 contiguous bases, and is generally about 5, 10, 12, 13, 14, 15, 16, 17, 18, 19, 20, 21, 22, 23, 24, or 25 nucleotides in length, or may be about 30, 35, 40, 45, 50, 55, 60, 65, 70, 75, 80, 85, 90, 95, or 100 nucleotides in length. The probes herein are selected to be complementary to different strands of a particular target nucleic acid sequence. This means that the probes must be sufficiently complementary so as to be able to specifically hybridize or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

In one embodiment, an oligonucleotide may be a primer, which refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in certain applications, an oligonucleotide primer is about 15-25 or more nucleotides in length, but may in certain embodiments be between 5 and 100 contiguous bases, and often be about 5, 10, 12, 13, 14, 15, 16, 17, 18, 19, 20, 21, 22, 23, 24, or 25 nucleotides long or, in certain embodiments, may be about 30, 35, 40, 45, 50, 55, 60, 65, 70, 75, 80, 85, 90, 95, or 100 nucleotides in length for. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

In certain embodiments, a reagent for determining expression of a gene product comprises a set of two, three or more oligonucleotides, wherein each oligonucleotide of the set hybridizes to a gene product described herein or a complementary strand of the gene product. Thus, e.g., each oligonucleotide may hybridize to an mRNA gene product and/or to one or more strands of a cDNA produced from the mRNA. In one embodiment, a set of oligonucleotides comprises DNA probes. In certain embodiments, a set of oligonucleotides comprises at least two amplification primers or PCR primers, which together are capable of amplifying at least a portion of a target nucleic acid sequence, e.g., an mRNA gene product or resulitng cDNA. In another embodiment, the sets of oligonucleotides or DNA probes may be provided on an array, such as solid phase arrays, chromosomal/DNA microarrays, or micro-bead arrays. Array technology is well known in the art and described herein.

Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. In certain embodiments, an oligonucleotide does not consist solely of wild-type chromosomal DNA or the in vivo transcription products thereof In certain embodiments, the present invention provides isolated polynucleotide, e.g., primers or probes, comprising various lengths of contiguous stretches of sequence identical to or complementary to a gene or polynucleotide gene product, e.g., mRNA, described herein.

Oligonucleotides, probes or primers may be modified in any way, as long as a given modification is compatible with the desired function of a given oligonucleotide. One of ordinary skill in the art can easily determine whether a given modification is suitable or desired for any given oligonucleotide of the present invention.

While the design and sequence of oligonucleotides depends on their function as described herein, several variables are generally taken into account. Among the most relevant are: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well known aspect of oligonucleotide design, and various computer programs are readily available to screen large numbers of potential oligonucleotides for optimal ones.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

The present invention includes the use of oligonucleotides that specifically bind to a target gene product under conditions suitable for performing any of the assays described herein, including but not limited to PCR, RT-PCR and real-time PCT. Suitable conditions are known in th art and include those used in standard reactions performed according to directions provided by retailers of PCR machines and reagents. In certain embodiments, the present invention contemplates polynucleotides, including oligonucleotides, that hybridize to reference nucleotide sequences (e.g., target gene products), or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C.

High stringency conditions also may include 1% BSA, 1 mM EDTA, 0.5 M NaHPO4 (pH 7.2), 7% SDS for hybridization at 65° C., and (i) 0.2×SSC, 0.1% SDS; or (ii) 0.5% BSA, 1 mM EDTA, 40 mM NaHPO4 (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the Tm for formation of a DNA-DNA hybrid. It is well known in the art that the Tm is the melting temperature, or temperature at which two complementary polynucleotide sequences dissociate. Methods for estimating Tm are well known in the art (see Ausubel et al., supra at page 2.10.8).

In general, the Tm of a perfectly matched duplex of DNA may be predicted as an approximation by the formula: Tm=81.5+16.6 (log 10 M)+0.41 (% G+C)−0.63 (% formamide)−(600/length) wherein: M is the concentration of Na+, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The Tm of a duplex DNA decreases by approximately 1° C. with every increase of 1% in the number of randomly mismatched base pairs. Washing is generally carried out at Tm−15° C. for high stringency, or Tm−30° C. for moderate stringency.

Oligonucleotides, primers and probes of the present invention may comprise or consist of regions that are polynucleotide variants of a portion of a target gene or mRNA sequence, or a complement thereof. In particular embodiments, an oligonucleotide may comprise or consist of a sequence having at least 70%, at least 80%, at least 90%, at least 95%, at least 98%, at least 99%, or 100% identity to a region of a target gene or mRNA sequence, or a complement thereof.

Oligonucleotides for use as primers or probes may be selected using software known in the art. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. Methods of oligonucleotide selection are not limited to those described herein.

In certain embodiments, oligonucleotides can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the oligonucleotide, e.g., to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake.

A variety of detectable molecules may be used to render an oligonucleotide, or protein detectable (i.e., detectably labeled), such as a radioisotopes, fluorochromes, dyes, enzymes, nanoparticles, chemiluminescent markers, biotin, or other monomer known in the art that can be detected directly (e.g., by light emission) or indirectly (e.g., by binding of a fluorescently-labeled antibody).

Radioisotopes provide examples of detectable molecules that can be utilized in certain aspects of the present invention. Several radioisotopes can be used as detectable molecules for labeling nucleotides or proteins, including, for example, 32P, 33P, 35S, 3H, and 125I. These radioisotopes have different half-lives, types of decay, and levels of energy which can be tailored to match the needs of a particular protocol. For example, 3H is a low energy emitter which results in low background levels, however this low energy also results in long time periods for autoradiography. Radioactively labeled ribonucleotides, deoxyribonucleotides and amino acids are commercially available. Nucleotides are available that are radioactively labeled at the first, or α, phosphate group, or the third, or γ, phosphate group. For example, both [α-32P] dATP and [γ-32P] dATP are commercially available. In addition, different specific activities for radioactively labeled nucleotides are also available commercially and can be tailored for different protocols.

Other examples of detectable molecules that can be utilized to detect an oligonucleotide include fluorophores. Several fluorophores can be used for labeling nucleotides including, for example, fluorescein, tetramethylrhodamine, Texas Red, and a number of others (e.g., Haugland, Handbook of Fluorescent Probes—9th Ed., 2002, Molec. Probes, Inc., Eugene Oreg.; Haugland, The Handbook: A Guide to Fluorescent Probes and Labeling Technologies-10th Ed., 2005, Invitrogen, Carlsbad, Calif.).

As one example, oligonucleotides may be fluorescently labeled during chemical synthesis, since incorporation of amines or thiols during nucleotide synthesis permit addition of fluorophores. Fluorescently labeled nucleotides are commercially available. For example, uridine and deoxyuridine triphosphates are available that are conjugated to ten different fluorophores that cover the spectrum. Fluorescent dyes that can be bound directly to nucleotides can also be utilized as detectable molecules. For example, FAM, JOE, TAMRA, and ROX are amine reactive fluorescent dyes that have been attached to nucleotides and are used in automated DNA sequencing. These fluorescently labeled nucleotides, for example, ROX-ddATP, ROX-ddCTP, ROX-ddGTP and ROX-ddUTP, are commercially available.

Non-radioactive and non-fluorescent detectable molecules are also available. As noted above, biotin can be attached directly to nucleotides and detected by specific and high affinity binding to avidin or streptavidin which has been chemically coupled to an enzyme catalyzing a colorimetric reaction (such as phosphatase, luciferase, or peroxidase). Digoxigenin labeled nucleotides can also similarly be used for non-isotopic detection of nucleic acids. Biotinylated and digoxigenin-labeled nucleotides are commercially available.

Very small particles, termed nanoparticles, also can be used to label oligonucleotide probes. These particles range from 1-1000 nm in size and include diverse chemical structures such as gold and silver particles and quantum dots. When irradiated with angled incident white light, silver or gold nanoparticles ranging from 40-120 nm will scatter monochromatic light with high intensity. The wavelength of the scattered light is dependent on the size of the particle. Four to five different particles in close proximity will each scatter monochromatic light, which when superimposed will give a specific, unique color. The particles are being manufactured by companies such as Genicon Sciences (Carlsbad, Calif.). Derivatized silver or gold particles can be attached to a broad array of molecules including, proteins, antibodies, small molecules, receptor ligands, and nucleic acids. For example, the surface of the particle can be chemically derivatized to allow attachment to a nucleotide.

Other types of nanoparticles that can be used for detection of a detectable molecule include quantum dots. Quantum dots are fluorescing crystals 1-5 nm in diameter that are excitable by light over a large range of wavelengths. Upon excitation by light having an appropriate wavelength, these crystals emit light, such as monochromatic light, with a wavelength dependent on their chemical composition and size. Quantum dots such as CdSe, ZnSe, InP, or InAs possess unique optical properties; these and similar quantum dots are available from a number of commercial sources (e.g., NN-Labs, Fayetteville, Ark.; Ocean Nanotech, Fayetteville, Ark.; Nanoco Technologies, Manchester, UK; Sigma-Aldrich, St. Louis, Mo.).

In certain embodiments, oligonucleotide primers or probes may be labeled with one or more light-emitting or otherwise detectable dyes. The light emitted by the dyes can be visible light or invisible light, such as ultraviolet or infrared light. In exemplary embodiments, the dye may be a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-(ε-carboxypentyl)-3'-ethyl-5,5'- dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4',5'-dichloro-2',7'-dimethoxyfluorescein (JOE); ALEXA FLUOR™; Cy2; Texas Red and Rhodamine Red; 6-carboxy-2',4,7,7'-tetrachlorofluorescein (TET); 6-carboxy-2',4,4',5',7,7'-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; IR800CW, ICG, Alexa Fluor 350; Alexa Fluor 488; Alexa Fluor 532; Alexa Fluor 546; Alexa Fluor 568; Alexa Fluor 594; Alexa Fluor 647; Alexa Fluor 680, or Alexa Fluor 750.

Certain embodiments, therefore, include methods for detecting a target polynucleotide gene product in a sample, comprising a) hybridizing the sample with a probe comprising a sequence complementary to the target polynucleotide gene product in the sample, and which probe specifically hybridizes to said target polynucleotide gene product, under conditions whereby a hybridization complex is formed between said probe and said target polynucleotide gene product or fragments thereof, and b) detecting the presence or absence of said hybridization complex, and, if present, the amount thereof. Also included are methods for detecting a target polynucleotide gene product in a sample, comprising a) amplifying the target polynucleotide gene product or fragment thereof, and b) detecting the presence or absence of said amplified target polynucleotide gene product or fragment thereof, and, if present, the amount thereof. In particular embodiments, the probe is detectably labeled.

Analysis of Gene Product Expression Levels

According to certain embodiments, methods and kits of the present invention may be used to determine whether a subject has thyroid cancer or whether a thyroid tumor or nodule is benign, based on the expression levels of gene products expressed by two or more genes shown in Table 1, including but not limited to any of the specific combination of gene products described herein. Generally, a determination of thyroid cancer is made when the expression pattern is determined to more closely correlate to the expression pattern observed in biological samples obtained from cancerous thyroid tissue than the expression pattern observed in biological samples obtained from normal or non-cancerous thyroid tissue. Similarly, a determination that the thyroid tissue sample if benign is generally made when the expression pattern is determined to more closely correlate to the expression pattern observed in biological samples obtained from normal or non-cancerous thyroid tissue than the expression pattern observed in biological samples obtained from cancerous thyroid tissue.

In certain instances, the presence of thyroid cancer is diagnosed by comparing the expression levels of one or more gene products described herein to a suitable control. A "suitable control" or "appropriate control" includes a reference value, e.g., expression level, feature, characteristic, or property, determined for a cell or other biological sample of a tissue or organism, e.g., a control or normal cell, tissue or organism, exhibiting, for example, normal traits, such as the absence of the condition, e.g., thyroid cancer. In certain embodiments, a "suitable control" or "appropriate control" is a predefined value, level, feature, characteristic, or property.

In certain embodiments, the expression of one or more gene products in a biological sample is compared to a reference expression level of the gene product, which may, in certain embodiments, be a predetermined or predefined value. Reference expression levels may be determined based upon the level of expression of a gene product in one or more suitable control samples, which may be either normal tissue samples or tumor tissue samples, e.g., a thyroid tumor. For instance, in certain embodiments, a reference expression level associated with normal tissue is determined based upon the level of expression of a gene product in 1, 2, 3, 5, 10, 20, 50, or more biological samples obtained from normal, non-cancerous tissue, such as, e.g., normal thyroid tissue. In other embodiments, a reference expression level associated with cancer tissue, e.g., thyroid cancer, is determined based upon the level of expression of a gene product in 1, 2, 3, 5, 10, 20, 50, or more biological samples obtained from cancer tissue, such as, e.g., thyroid cancer tissue. In certain embodiments, reference expression levels in either or both normal and cancer tissue are determined for one or more, two or more, or three or more gene products expressed by a gene in Table 1 or at least one, at least two, or at least three genes selected from the CXCR3, CCR3, CXCL10, CAR, XB130, HO-1 and CCR7 genes. In related embodiments, reference expression levels in either or both normal and cancer tissue are determined for any of the sets of gene products described herein, e.g., gene sets comprising or consisting of: gene products of the CCR3, TIMP-1, CAR and XB130 genes; gene products of the CXCL10, TIMP-1, CAR and CCR7 genes; gene products of the TIMP-1, CAR and CCR7 genes; or gene products of the CXCL10, TIMP-1, CLDN-1, and CCR7 genes.

In particular embodiments, differential expression of one or more, two or more, or three or more of the gene products in a biological sample as compared to expression in a normal (non-cancerous) control sample or control reference is indicative of cancer. In contrast, substantially similar expression of one or more, two or more, or three or more of the gene products in a biological sample as compared to expression in a normal (non-cancerous) control sample or control reference is indicative of benign tissue, whereas substantially similar expression of one, two or more of the gene products in a biological sample as compared to expression in a cancer control sample or cancer control reference is indicative of cancer.

Differential expression includes a statistically significant difference in one or more expression levels of a gene product as compared to the expression levels of the same gene product in an appropriate control. The statistically significant difference may relate to either an increase or a decrease in expression levels, as measured by RNA levels, protein levels, protein function, or any other relevant measure of gene expression such as those described herein. A result is typically referred to as statistically significant if it is unlikely to have occurred by chance. The significance level of a test or result relates traditionally to a frequentist statistical hypothesis testing concept. In simple cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see, e.g., Goodman S, Ann Intern Med 130:1005-13, 1999). In certain cases, the significance level of a test or result may reflect an analysis in which the probability of making a decision to reject the null hypothesis when the null hypothesis is actually true is no more than the stated probability. This type of analysis allows for those applications in which the probability of deciding to reject may be much smaller than the significance level for some sets of assumptions encompassed within the null hypothesis.

In certain exemplary embodiments, statistically significant differential expression may include situations wherein the expression level of a given gene product is at least an about 1.2×, 1.3×, 1.4×, 1.5×, 1.6×, 1.7×, 1.8×, 1.9×, 2.0×, 2.2×, 2.4×, 2.6×, 2.8×, 3.0×, 4.0×, 5.0×, 6.0×, 7.0×, 8.0×, 9.0×, 10.0×, 15.0×, 20.0×, 50.0×, 100.0×, or greater difference in expression (i.e., differential expression that may be higher or lower expression) in a biological sample as compared to an appropriate control, including all integers and decimal points in between (e.g., 1.24×, 1.25×, 2.1×, 2.5×, 60.0×, 75.0×, etc.). In certain embodiments, statistically significant differential expression may include situations wherein the expression level of a given gene product is at least an about 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000 percent (%) or greater difference in expression (i.e., differential expression that may be higher or lower) in a biological sample as compared to an appropriate control, including all integers and decimal points in between.

As an additional example, differential expression may also be determined by performing Z-testing, i.e., calculating an absolute Z score, as known in the art. Z-testing is typically utilized to identify significant differences between a sample mean and a population mean. For example, as compared to a standard normal table (e.g., a control tissue), at a 95% confidence interval (i.e., at the 5% significance level), a Z-score with an absolute value greater than 1.96 indicates non-randomness. For a 99% confidence interval, if the absolute Z is greater than 2.58, it means that p<0.01, and the difference is even more significant—the null hypothesis can be rejected with greater confidence. In these and related embodiments, an absolute Z-score of 1.96, 2, 2.58, 3, 4, 5, 6, 7, 8, 9, 10, 11, 12, 13, 14, 15, 16, 17, 18, 19, 20 or more, including all decimal points in between (e.g., 10.1, 10.6, 11.2, etc.), may provide a strong measure of statistical significance. In certain embodiments, an absolute Z-score of greater than 6 may provide exceptionally high statistical significance.

Substantial similarly relates generally to the lack of a statistically significant difference in the expression levels between the biological sample and the reference control. Examples of substantially similar expression levels may include situations wherein the expression level of a given gene product provides less than about a 0.05×, 0.1×, 0.2×, 0.3×, 0.4×, 0.5×, 0.6×, 0.7×, 0.8×, 0.9×, 1.0×, 1.1×, 1.2×, 1.3×, or 1.4× difference in expression (i.e., differential expression that may be higher or lower expression) in a biological sample as compared to a reference sample, including all decimal points in between (e.g., 0.15×, 0.25×, 0.35×, etc.). In certain embodiments, differential expression may include situations wherein the expression level of a given gene product provides less than about 0.25, 0.5, 1, 2, 3, 4, 5, 6, 7, 8, 9, 10, 11, 12, 13, 14, 15, 16, 17, 18, 19, 20, 30, 40, 50 percent (%) difference in expression (i.e., differential expression that may be higher or lower) in a biological sample as compared to a reference sample, including all decimal points in between.

Differential expression may refer to an increase or a decrease in expression of a given gene product as compared to a control sample or value. In particular embodiments of methods described herein, an increase in expression of one or more, two or more, three or more, or four or more gene products of the CCR3, CXCL10, CK19, TIMP1, CLDN1, CCR7 and HO-1 genes and/or a decrease in expression of one or more, two or more, three or more gene products of the CXCR3, CAR and XB130 genes, or the corresponding changes in any of the various subsets of gene products describes herein, in a biological sample as compared to the expression level in a normal control sample or value is indicative of the presence of a tumor or cancer. The increase or decrease may correspond to any of the differences in expression noted above, such as, e.g., an increase of about 10, 20, 50, 100, 200, 500, or 1000% or a decrease of about 10, 20, 50, or 90%.

As noted above, in particular embodiments, the determination of whether a biological sample comprises cancer tissue or not involves correlating the expression of levels of one or more gene products with the presence or absence of cancer. This may be accomplished by comparing the expression levels of the gene products in the biological sample to the expression levels in one or more control samples, such as samples obtained from subjects known to have cancer or known to not have cancer. In certain embodiments, the correlation or comparison may be performed using gene expression data obtained from control samples at an earlier time, such as predefined or predetermined reference values.

As described herein, methods of the present invention may be used to qualitatively or quantitatively determine the expression levels of one or more gene products, using any of a number of methods known in the art. In some cases, the degree of hybridization of a detectably probe is directly related to the amount of gene product in a biological sample. Software can be used to extract, normalize, summarize, and analyze signals from probes. In some embodiments, the signal intensity of a given probe determined for a biological sample can be compared against a reference set to determine whether differential expression is occuring in the sample. For example, in the context of a microarray, an increase or decrease in relative intensity at a position on an array corresponding to an expressed gene product is indicative of an increase or decrease respectively of expression of the corresponding gene in the biological sample.

Gene expression analysis and correlation with cancer or benign phenotypes may be performed using classifiers or algorithms, e.g., algorithms designed to normalize and or improve the reliability of the data. Algorithms that may be used include any of those described herein, e.g., the classifiers or algorithms described in Examples 2 and 3. In certain embodiments, the gene product is mRNA, which may be measured using realtime PCR, e.g., as described in Example 1. In certain embodiments, the classifying potential of various gene may be determined using the CT values of each gene to produce ROC curves based upon expression of the various genes in thyroid tissue samples obtained from malignant and benign thyroid nodules, as illustrated in Example 1. The sensitivity and specificity of each gene may also be determined.

In particular embodiments, the algorithm is a multi-gene classifying test. Such a classifier may be developed using a two-step approach, in which the first step identifies and classifies a group of biological samples with atypical CT values, and the second step generates an algorithm for classifying the biological samples remaining unclassified after the first step, e.g., as described in Example 2. The consolidated data from both steps may be integrated and plotted in a ROC curve.

In certain embodiments, the first step includes two phases. The first phase identifies biological samples with atypical CT values for a given set of genes. The criteria to define an atypical CT may be defined as the mean CT value+/−two standard deviations, therefore representing only 5% of CT values for any given gene. For each gene, the error probability (EP) of an atypical CT belonging to the cancer group while truly belonging to the benign group may be calculated. Given that the lower the EP reflects a greater classifying ability, a score may be calculated for each gene based on the EP. In the second phase, a composite score obtained from the genes with best scores may be used to classify the sample as cancer or benign.

In certain embodiments of the second step, samples not classified in the first step may be used as the remaining training set to generate a downstream algorithm to complete the classification of all the data, as diagrammed in FIG. 3. For example, this may performed using two methods, Linear discriminant analysis (LDA) and Non-linear discriminant analysis (NLDA). For LDA analysis a stepwise LDA approach may be used, since it may be unknown if the variables and samples meet the conditions required for an LDA. The stepwise approach may be chosen, because it may simultaneously identify the combination of variables that give the greatest classification certainty and satisfy conditions for an LDA. For NLDA, a genetic algorithm-based method to evolve a set of mathematical functions, resulting in either linear or nonlinear combinations of two or more features may be used (Melo et al, *Protein Science*, 2007). This method generates non-linear transforms of combinations of up to four genes to produce single composite scores.

To integrate both steps, a numerical value may be assigned to the data obtained in the first step in order to give them a similar output identity to the values obtained in the second step or phase, as diagrammed in FIG. 3.

In certain embodiments, a classifier or algorithm (or the genes it is based upon) is selected to maximize the sensitivity/specificity relationship, reaching both positive predictive values (PPV) and negative predictive values (NPV) greater than 90%, and/or achieve AUC>90.

In particular embodiments, correlation and/or the determination of whether a biological sample obtained from a subject is cancerous or benign is determined using a classifier or algorithm, e.g., a two-step classifier, based on the expression of one or more, two or more, or three or more gene products described herein, including gene products expressed by any of the following sets of gene products:

two or more or three or more gene products of the CXCR3, CCR3, CXCL10, CK19, TIMP-1, CLDN-1, CAR, XB130, HO-1 and CCR7 genes;

the gene products of the CXCR3, CCR3, CXCL10, CK19, TIMP-1, CLDN-1, CAR, HO-1 and CCR7 genes;

the gene products of the CCR3, TIMP-1, CAR and XB130 genes;

the gene products of the CXCL10, TIMP-1, CAR and CCR7 genes;

the gene products of the TIMP-1, CAR and CCR7 genes; or the gene products of the CXCL10, TIMP-1, CLDN-1, and CCR7 genes.

In certain embodiments, methods of the present invention may be performed using a "machine learning algorithm," which refers to a computational-based prediction methodology, also known to persons skilled in the art as a "classifier", which may be employed for characterizing a gene expression profile. The signals corresponding to certain expression levels, which are obtained by, e.g., microarray-based hybridization assays, are typically subjected to the algorithm in order to classify the expression profile. Supervised learning generally involves "training" a classifier to recognize the distinctions among classes, e.g., cancer vents benign thyroid tissue, and then "testing" the accuracy of the classifier on an independent test set. For new, unknown samples, the classifier can be used to determine the class in which the samples belong. In particular embodiments, the correlating is performed using an algorithm, including based on expresion levels of any of the sets of gene products described herein.

Examples of types of algorithms suitable for categorization of samples include but are not limited to k-nearest neighbor algorithms, support vector algorithms, naive Bayesian algorithms, neural network algorithms, hidden Markov model algorithms, genetic algorithms, or any combination thereof. In some embodiments of the present invention, a diagonal linear discriminant analysis, k-nearest neighbor algorithm, support vector machine (SVM) algorithm, linear support vector machine, random forest algorithm, or a probabilistic model-based method or a combination thereof is provided for classification of microarray data. In some embodiments, identified markers that distinguish samples (e.g. benign vs. malignant, normal vs. malignant) or distinguish subtypes (e.g. PTC vs. FVPTC) are selected based on statistical significance of the difference in expression levels between classes of interest. In some cases, the statistical significance is adjusted by applying a Benjamini Hochberg or another correction for false discovery rate (FDR).

In certain embodiments, algorithms of the present invention may include one or more additional analytical features of computations. For example, methods of analyzing gene product expression levels may include the use of a feature selection algorithm, which may be provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420). Methods of analyzing gene product expression levels may include the use of a pre-classifier algorithm. For example, an algorithm may use a cell-specific molecular fingerprint to pre-classify the samples according to their composition and then apply a correction/normalization factor. This data/information may then be fed in to a final classification algorithm which would incorporate that information to aid in the final diagnosis.

Selected features may be classified using a classifier algorithm. Illustrative algorithms include but are not limited to methods that reduce the number of variables such as principal component analysis algorithms, partial least squares methods, and independent component analysis algorithms. Illustrative algorithms further include but are not limited to methods that handle large numbers of variables directly such as statistical methods and methods based on machine learning techniques. Statistical methods may include penalized logistic regression, prediction analysis of microarrays (PAM), methods based on shrunken centroids, support vector machine analysis, and regularized linear discriminant analysis. Machine learning techniques include bagging procedures, boosting procedures, random forest algorithms, and combinations thereof. Cancer Inform. 2008; 6: 77-97 provides an overview of the classification techniques provided above for the analysis of microarray intensity data.

In some cases, an algorithm according to the present invention may be supplemented with a meta-analysis approach, such as that described by Fishel and Kaufman et al. 2007 Bioinformatics 23(13): 1599-606. In some cases, the classifier algorithm may be supplemented with a meta-analysis approach such as a repeatability analysis. In some cases, the repeatability analysis selects markers that appear in at least one predictive expression product marker set.

In certain embodiments, the levels of gene product expression, e.g., the resulting intensity values for each gene product, measured in a sample can be analyzed using feature selection techniques, such as but not limited to filter techniques that assess the relevance of features by looking at the intrinsic properties of the data, wrapper methods that embed the model hypothesis within a feature subset search, and embedded techniques in which the search for an optimal set of features is built into a classifier algorithm.

Examples of filter techniques useful in the methods of the present invention include: (1) parametric methods such as the use of two sample t-tests, ANOVA analyses, Bayesian frameworks, and Gamma distribution models; (2) model free methods such as the use of Wilcox on rank sum tests, between-within class sum of squares tests, rank products methods, random permutation methods, or TnoM, which involves setting a threshold point for fold-change differences in expression between two datasets and then detecting the threshold point in each gene that minimizes the number of missclassifications; and (3) multivariate methods such as bivariate methods, correlation based feature selection methods (CFS), minimum redundancy maximum relevance methods (MRMR), Markov blanket filter methods, and uncorrelated shrunken centroid methods. Wrapper methods useful in the methods of the present invention include sequential search methods, genetic algorithms, and estimation of distribution algorithms. Embedded methods useful in the methods of the present invention include random forest algorithms, weight vector of support vector machine algorithms, and weights of logistic regression algorithms. Bioinformatics. 2007 Oct. 1; 23(19):2507-17 provides an overview of the relative merits of the filter techniques provided above for the analysis of intensity data.

In certain embodiment, expression levels of gene products in a sample may be compared to gene expression data for two or more different sets of biomarkers, the gene expression data for each set of biomarkers comprising one or more reference gene expression levels correlated with the presence of one or more tissue types, e.g., thyroid tumor tissue, wherein the expression levels are compared to gene expression data for the two or more biomarkers in sequential fashion. Comparison of expression levels to gene expression data for sets of biomarkers may comprise the application of a classifier or sequential application of different classifiers, including those described herein, to the gene expression data. Sequential analysis may involve applying a classifier obtained from gene expression analysis of samples of cancer tissue, followed by applying a classifier obtained from analysis of a mixture of different biological samples, some of such samples containing cancer tissues and others containing benign tissue.

In certain embodiments, classifiers used early in the sequential analysis may be used to either rule-in or rule-out a sample as benign or suspicious. In some embodiments, such sequential analysis ends with the application of a "main" classifier to data from samples that have not been ruled out by the preceding classifiers, wherein the main classifier is obtained from data analysis of gene expression levels in multiple types of tissue and wherein the main classifier is capable of designating the sample as benign or suspicious (or malignant).

For example, in certain embodiments, profiling using sets of genes or biomarkers can be used to characterize thyroid tissue as benign, suspicious, and/or malignant. Sets may be derived from analysis of gene expression levels of cohorts containing benign (non-cancerous) thyroid subtypes including follicular adenoma (FA), nodular hyperplasia (NHP), lymphocytic thyroiditis (LCT), and Hurthle cell adenoma (HA); malignant subtypes including follicular carcinoma (FC), papillary thyroid carcinoma (PTC), follicular variant of papillary carcinoma (FVPTC), medullary thyroid carcinoma (MTC), Hurthle cell carcinoma (HC), and anaplastic thyroid carcinoma (ATC). Such panels may also be derived from non-thyroid subtypes including renal carcinoma (RCC), breast carcinoma (BCA), melanoma (MMN), B cell lymphoma (BCL), and parathyroid (PTA). Biomarker sets associated with normal thyroid tissue (NML) may also be used in the methods and compositions provided herein. Exemplary biomarkers are provided in Table 1, and specific sets of biomarkers are described herein.

As discussed above, the methods and kits of the present invention may relate to the use of particular sets of genes or gene products, e.g., "biomarker sets", for purposes of identification, classification, diagnosis, or to otherwise characterize a biological sample. The invention may also use groups of biomarker sets, herein described as "classification sets." Often the pattern of levels of gene expression of biomarkers in a set (also known as a signature) is determined and then used to evaluate the signature of the same set of biomarkers in a biological sample, such as by a measure of similarity between the sample signature and the reference signature. In some embodiments, the method involves measuring (or obtaining) the levels of two or more gene products that are within a biomarker set and/or within a classification set. For example, in some embodiments, a biomarker set or a classification set may contain at least 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, or 300 biomarkers. In some embodiments, a biomarker set or a classification set contains no more than 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, or 300 biomarkers. In some embodiments, a classification set contains at least 1, 2, 3, 4, 5, 6, 7, 8, 9, 10, 15, 20, or 25 different biomarker sets. In other embodiments, a classification panel contains no more than 1, 2, 3, 4, 5, 6, 7, 8, 9, 10, 15, 20, 25 different biomarker sets.

Biomarker sets may be chosen to accommodate adequate separation of benign from non-benign or suspicious expression profiles. Training of the classifier, i.e., algorithm, can be performed on numerous biological samples, such as at least 50, 100, 200, 300, 400, 500, 600, 700, 800, 900, 1000, 1500, 2000, 2500, 3000, 3500, or 4000 biological samples (e.g., thyroid samples). The total sample population can consist of samples obtained from FNAs, or the sample population may be a mixture of samples obtained by FNAs and by other methods, e.g., post-surgical tissue. In some embodiments, many training/test sets are used to develop the preliminary algorithm. The overall algorithm error rate may be shown as a function of gene number for benign vs. non-benign samples. In some embodiments, other performance metric may be used, such as a performance metric that is a function of gene number for either subtypes or benign vs. malignant (B vs. M). Such performance metric may be obtained using CV, or other method known in the art. All results may be obtained using a support vector machine model which is trained and tested in a cross-validated mode on the samples.

A statistical evaluation of the results of the molecular profiling may provide a quantitative value or values indicative of one or more of the following: the likelihood of diagnostic accuracy; the likelihood of cancer; or the likelihood of a particular cancer subtype. The data may be presented directly to the physician in its most useful form to guide patient care.

The results of the molecular profiling can be statistically evaluated using a number of methods known to the art including, but not limited to: the students T test, the two sided T test, pearson rank sum analysis, hidden markov model analysis, analysis of q-q plots, principal component analysis, one way ANOVA, two way ANOVA, LIMMA and the like.

In some embodiments of the present invention, the methods of the present invention, alone or in combination with cytological analysis, may provide a classification, identification, or diagnosis, e.g., of cancer or benign, that is between about 85% accurate and about 99% or about 100% accurate.

Algorithms based on each of the biomarker or classification sets described herein may use information on gene product expression levels determined during algorithm training to rule in, or rule out a given sample as "benign," "suspicious," or as comprising or not comprising one or more tissue types (e.g. NML, FA, NHP, LCT, HA, FC, PTC, FVPTC, MTC, HC, ATC, RCC, BCA, MMN, BCL, and PTA). Each biomarker or classification set algorithm may use simple decision rules to filter incoming samples, effectively removing any flagged samples from subsequent evaluation if the decision rules are met (e.g. a sample is characterized regarding the identity or status of one or more tissue types contained therein). The biomarker sets and classification sets provided herein are useful for classifying, characterizing, identifying, and/or diagnosing thyroid cancer or other thyroid condition (including diagnosing the thyroid as normal or benign).

Analysis of the gene expression levels may involve sequential application of different classifiers or algorithms described herein to the gene expression data. In certain embodiments, such sequential analysis may involve applying a classifier obtained from gene expression analysis of a plurality of samples of cancerous thyroid tissue, followed by applying a classifier obtained from analysis of a mixture of different samples of thyroid tissue, with some of the samples containing cancerous thyroid tissues and others containing benign thyroid tissue. In some embodiments, the classifier is obtained from analysis of gene expression patterns in benign tissue, normal tissue, and/or non-thyroid tissue (e.g., parathyroid tissue). In some embodiments, the diseased tissue is HA and/or HC tissue.

In some embodiments, the classification process begins when each classification panel receives as input biomarker expression levels (e.g., summarized microarray intensity values, qPCR, or sequencing data) from a biological sample. The biomarkers and expression levels specified in a classification panel are then evaluated. If the data from a given sample matches the rules specified within the classification panel (or otherwise correlate with the signature of the classification panel), then its data output flags the sample and prevents it from further evaluation and scoring by the main (downstream) classifier. When a classification panel flags a sample, the system automatically returns a "suspicious" call for that sample. When a classification panel does not flag a sample, the evaluation continues downstream to the next classification panel and it may be flagged or not flagged. In some situations, the classification panels are applied in a specific order; in other cases, the order of the applications can be any order.

In certain embodiments, the classification process begins with determining, such as by gene expression analysis, expression level(s) for one or more gene products from a sample (e.g. a thyroid tissue sample) from a subject. Separately, one or more sets of reference or training samples may be analyzed to determine gene expression data for at least two different sets of biomarkers, the gene expression data for each biomarker set comprising one or more gene expression levels correlated with the presence of one or more tissue types. The gene expression data for a first set of biomarkers may be used to train a first classifier; gene expression data for a second set may be used to train a second classifier; and so on for 2, 3, 4, 5, 6, 7, 8, 9, 10, 11, 12, 13, 14, 15, 16, or more sets of biomarkers and optionally corresponding classifiers. The sets of reference or training samples used in the analysis of each of the sets of biomarkers may be overlapping or non-overlapping. In some embodiments, the reference or training samples comprise HA and/or HC tissue. In the next step of the example classification process, a first comparison is made between the gene expression level(s) of the sample and the first set of biomarkers or first classifier. If the result of this first comparison is a match, the classification process ends with a result, such as designating the sample as suspicious, cancerous, or containing a particular tissue type (e.g. HA or HC). If the result of the comparison is not a match, the gene expression level(s) of the sample are compared in a second round of comparison to a second set of biomarkers or second classifier. If the result of this second comparison is a match, the classification process ends with a result, such as designating the sample as suspicious, cancerous, or containing a particular tissue type (e.g. HA or HC). If the result of the comparison is not a match, the process continues in a similar stepwise process of comparisons until a match is found, or until all sets of biomarkers or classifiers included in the classification process are used as a basis of comparison. If no match is found between the gene expression level(s) of the sample and any set of biomarkers or classifiers utilized in the classification process, the sample may be designated as "benign." In some embodiments, the final comparison in the classification process is between the gene expression level(s) of the sample and a main classifier, as described herein.

In some embodiments of the present invention, data analysis or correlating requires a computer or other device, machine or apparatus for application of the various algorithms described herein due to the large number of individual data points that are processed.

Kits

In particular embodiments, the present invention provides kits or diagnostic tests for diagnosing or predicting cancers, e.g., thyroid cancer, in subjects. The diagnostic tests described herein may be in vitro diagnostic tests. Diagnostic tests include but are not limited to FDA approved, or cleared, In Vitro Diagnostic (IVD), Laboratory Developed Test (LDT), or Direct-to-Consumer (DTC) tests, that may be used to assay a biological sample and detect or indicate the presence or absence of a cancer, such as a thyroid cancer. In one embodiment, a diagnostic test or kit may be used in a laboratory or other health professional setting. In another embodiment, a diagnostic test or kit may be used by a consumer at home.

Diagnostic tests and kits comprise one or more reagents for detecting a gene product described herein and may comprise other reagents, instruments, and systems intended for use in the in vitro diagnosis of a caner, e.g., thyroid cancer, in order to cure, mitigate, treat, or prevent disease or its sequelae. In one embodiment, the kits or diagnostic tests described herein may be intended for use in the collection, preparation, and examination of specimens taken from the human body. In certain embodiments, kits, diagnostic tests and products may comprise one or more laboratory tests. As used herein, the term "laboratory test" means one or more medical or laboratory procedures that involve testing a biological sample obtained from a subject.

The kits and diagnostic tests of the present invention comprise one or more reagents for detecting a gene product described herein, such as those expressed by a gene listed in Table 1. In this regard, the reagents for detecting may comprise any reagent known to the skilled person for detecting gene products, including but not limited to antibodies and oligonucleotides. In certain embodiments, the kit or diagnostic assay may further comprise written instructions on how to perform as assay described herein to determine the expression levels of the gene product using the kit.

In certain embodiments, a kit or diagnostic assay of the present invention comprises two or more, three or more, or four or more reagents, e.g., probes, for detecting a gene product described herein. In particular embodiments, the gene products are proteins or nucleic acids, e.g., mRNA. In certain embodiments, the reagents are antibodies or oligonucleotides, including any of those described herein. In certain embodiments, each reagent is a set of oligonucleotides, e.g., wherein each set comprises or consists of two oligonucleotides that together are capable of amplifying a target polynucleotide gene product, by PCR. In certain embodiments, the reagents are detectably labeled. In one embodiment, a kit or diagnostic assay comprises two or more, three or more, or four or more reagents for detecting a gene product, wherein the kit or diagnostic asay comprises two or more, three or more, or four or more sets of primers, each set capable of amplifying at least a portion of a target gene product. In certain embodiments, said kit or diagnostic assay further comprises two or more, three or more, or four or more detably labeled probes, each probe specifically binding to one of the target gene products or a complement thereof. Accordingly, in certain embodiments, each set of primers is used to amplify a target gene product, and then each probe is used to detect the amplification products and thus measure the expression level of each gene product. In particular embodiments, each reagent, e.g., each set of primers, detects a different gene product. However, it is understood that certain embodiments may include two or more reagents that amplify the same gene product. For example, a kit or diagnostic assay may comprise two reagents, one being a set of amplification primers and the other being a probe, that each specificall bind and/or detect the same gene product. In addition, a kit or diagnostic assay may comprise multiple combinations of two or more reagents that each specifically bin or detect the same gene product, e.g., wherein each combination specifically binds or detects a different gene product, thus allowing for the amplification and detection of multiple gene products, e.g., at the same time.

In particular embodiments, the gene products detected by the reagents of the kit or diagnostic assay are expressed by one or more genes listed in Table 1, wherein at least one of the gene products is expressed by a CXCR3, CCR3, CXCL10, CAR, XB130, HO-1 or CCR7 gene. In certain embodiments, the gene products comprise or consist of: three or more gene products of the CXCR3, CCR3, CXCL10, CK19, TIMP-1, CLDN-1, CAR, XB130, HO-1 and CCR7 genes; the gene products of the CXCR3, CCR3, CXCL10, CK19, TIMP-1, CLDN-1, CAR, HO-1 and CCR7 genes; the gene products of the CCR3, TIMP-1, CAR and XB130 genes; the gene products of the CXCL10, TIMP-1, CAR and CCR7 genes; the gene products of the TIMP-1, CAR and CCR7 genes; or the gene products of the CXCL10, TIMP-1, CLDN-1, and CCR7 genes.

In certain embodiments, the kit or diagnostic assay comprises each reagent in a separate container. In other embodiments, each reagent is provided in the same container. In particular embodiments, the reagents are each attached to a substrate, such as, e.g., an array. In particular embodiments, the reagents are each attached to discrete regions of a solid substrate. Accordingly, in one embodiment, the reagents are oligonucleotides or sets of oligonucleotides covalently bound to a solid substrate, wherein the solid substrate is optionally an array, and wherein the array is optionally a microarray. In certain embodiments, the reagents are sets of oligonucleotides, e.g., primers, and the sets of oligonucleotides comprise DNA.

The kits or diagnostic assays of the present invention may further comprise one or more solutions suitable for binding said reagents to said gene products, and/or one or more solutions or reagents utilized in performing a method of the present invention to determine an expression level of the gene products. For example, in particular embodiments, a kit or diagnostic assay that comprises sets of PCR primer, may further comprise one or more additional reagents for performing a PCR assay, such as, e.g., a thermostable polymerase, a mixture of deoxynucleotides, and/or a detectably labeled probe. In particular embodiment, the detectably labeled probe comprises a fluorophore and a quenching moiety, and the probe may emit a detectable signal when the probe is cleaved but not when the probe is intact.

The kits or diagnostic assays of the present invention may further comprise one or more reagents for processing and/or storing a biological sample, e.g., wherein the processing of the thyroid tissue sample comprises extracting the gene products from the biological sample.

The kits or diagnostic assays of the present invention may further comprise one or more control gene products, such as, e.g., positive controls that contain a sample of the gene product and/or a negative control that does not, in order to confirm that the methods performed was successful in specifically identifying and/or measuring expression and/or presence of gene products.

In certain embodiments, a kit or diagnostic assay comprises data or information, e.g., corresponding to gene expression levels of the gene products in positive and/or negative control samples or predetermined cut-off levels of gene expression indicative of the presence or absence of a cancer, such as a thyroid cancer. In related embodiments, the kit or diagnostic assay comprises an alorithm for use in correlating the expression levels of the gene in a biological sample with the presence or absence of a cancer, e.g., a thyroid cancer. In particular embodiments, the kit or diagnostic assay comprises a computer readable medium containing the data and/or algorithm, or containing code for the data or algorithm.

In particular embodiments, one or more of the reagents for detecting gene products, the solution, the additional reagents, and the control gene products are in separate containers.

EXAMPLES

Example 1

Selection of Genes for Diagnostic Assay

Eighteen genes pre-selected based on their relation to thyroid cancer were used to develop an improved diagnostic assay that would accurately classify indeterminate thyroid nodules as benign or cancer. These genes included CXCR3 (Gene 1), CXCR3A (Gene 2), CXCR3B (Gene 3), CXCR4 (Gene 4), CCR3 (Gene 5), CXCL9 (Gene 6), CXGL10 (Gene 7), CXCL11 (Gene 8), SPAG-9 (Gene 9), CK-19 (Gene 10), TIMP-1 (Gene 11), CLDN-1 (Gene 12), CAR (Gene 13), Nectin-1 (Gene 14), XB-130 (Gene 15). HO-1 (Gene 16), CCR7 (Gene 17), and CXCL4 (Gene 18).

As a training set, fresh snap frozen thyroid tissue samples from both malignant and benign thyroid nodules were collected prospectively in the operating room (n=156), including 100 thyroid carcinomas and 56 benign thyroid nodules. Subtypes of thyroid cancer included papillary thyroid carcinoma (PTC) usual type (56), follicular variant (22), diffuse sclerosing (8) and follicular carcinoma (FC) (14). Benign nodules included follicular hyperplasia (26), thyroiditis (14) and follicular adenoma (16). Final biopsy reports for all surgical specimens were reviewed and confirmed by two independent specialized pathologists. The samples were placed immediately in RNA preserving solution (RNAlater, Ambion) at 4° C. followed by homogenization using a RNAeasy Plus Mini kit (Qiagen) and stored at −80° C. The concentration of RNA was determined using a Picodrop TOO spectophotometer. RNA integrity was confirmed using agarose-formaldehyde electrophoresis.

Gene differential expression was analyzed by realtime PCR to determine the classifying potential of each gene, both individually and in different combinations. The synthesis of the complementary DNA (cDNA) was performed using the ImProm-II Reverse Transcription System (Promega). Realtime PCR was performed in duplicate samples with the Rotor Gene Q cycler from Qiagen, using the Brilliant II SYBR Green master mix (Agilent) kit following the manufacturer instructions. The standard curves were analyzed by means of the RotorGene software application to determine the optimum amplification conditions for each gene. The efficiency values obtained ranged from 95% to 109%. The linear regression coefficient values (Rsq) obtained were within a range from 0.990 to 0.999. For initial comparisons, gene expression was normalized with 18s and β-actin and analyzed by the relative quantification model proposed by Pfaffl. Results are presented in FIG. 1 as the relative-fold change in cancer relative to benign thyroid nodules.

Using CT values of each gene, Receiving Operating Characteristic (ROC) curves were generated to compare the ability of each individual gene to classify thyroid samples. The area under the curve (AUC), and optimal sensitivity and specificity were determined and are provided in FIG. 2. Individually, the genes with best AUC and sensitivity/specificity values were gene 11 (AUC:0.87 and sensitivity/specificity: 96%/78%), gene 12 (AUC:0.85 and sensitivity/specificity: 85%/73%) and gene 10 (AUC:0.84 and sensitivity/specificity: 81%/79%). Genes 17 and 5 showed AUC's of 0.74 and 0.70, respectively. All other genes showed poor classifying performance, as shown in FIG. 2.

Example 2

Development of Diagnostic Assays

Figure 3A:
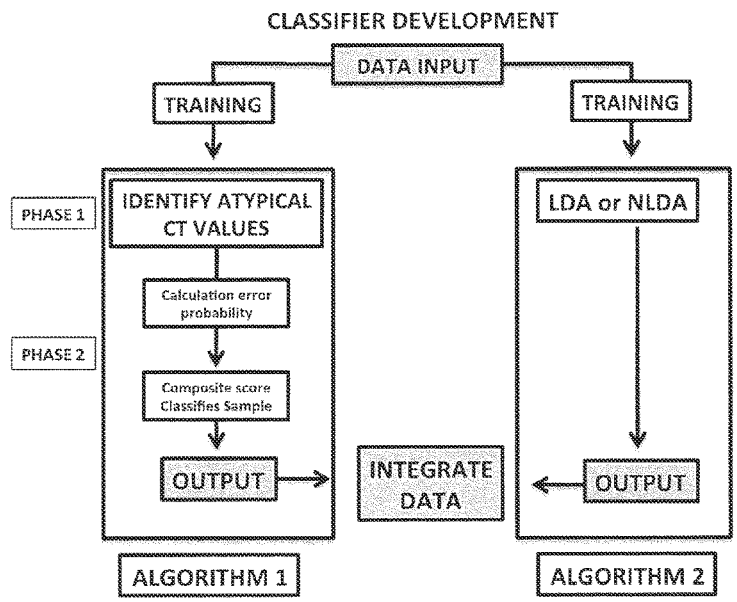
FIG. 3 provides a schematic diagram of the methods used to generate (3A) and use different (3B) algorithms to develop new classifiers. Two different algorithms were trained; one to identify and classify atypical (outlier) CT values and one to classify non-atypical CT values (linear and non-linear discriminant analysis) (3A). New classifiers are developed by using the algorithms sequentially in two steps followed by integration of output data to develop the new classifier (3B).

A multi-gene classifying test (gene signature), which maximizes the sensitivity/specificity relationship, reaching both positive predictive values (PPV) and negative predictive values (NPV) greater than 90% was used. Criteria for selecting optimal sets of genes to use in classifiers were: AUC greater than 0.97, with both sensitivity and specificity values greater than 92% and 90%, respectively; the gene classifier should be robust and withstand atypical gene profile variations without overfitting. In addition, the signature should use a small set of genes, thus allowing a simple kit to be used in a point of care diagnostic setting such as pathology laboratories. To meet these criteria, separate algorithms were trained; the first one identified and classified samples with atypical (outlier) CT values, and second one classified samples with non-atypical CT values (FIG. 3A). To integrate output data from both algorithms, the data obtained from the first algorithm was mathematically transformed to give a similar output identity to the data obtained from the second algorithm (FIG. 3A).

To develop the classifier, the algorithms were used sequentially in a two-step process. The first step of the classifier included two phases; the first phase identified samples with atypical CT values (outliers) defined as values greater than two standard deviations from the mean CT value for each gene (FIGS. 3A and B). If a sample satisfied the criteria of an atypical CT for a gene, it followed to the second phase, which calculated the error probability (EP) of an atypical CT value belonging to the cancer group while truly belonging to the benign group. The EP calculated for the selected genes was expressed as an individual score, which was used to generate a composite score that classified the sample as cancer or benign (FIGS. 3A and B). The first step identified 21 of 56 of benign samples and 36 of 100 cancer samples as atypical and classified them with 100% accuracy.

Figure 3B:
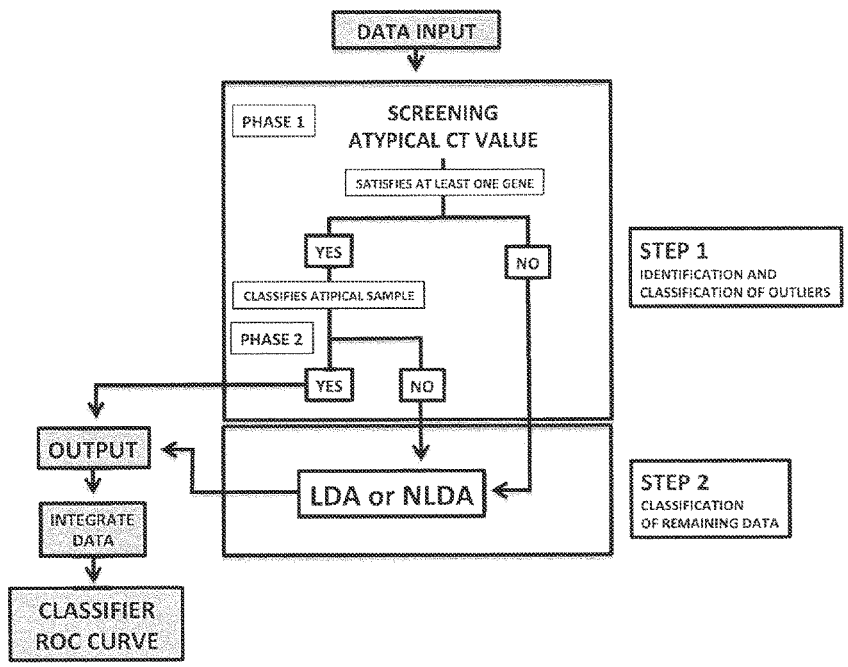

Samples that did not satisfy atypical CT value criteria of the first phase or were not classified in the second phase followed the classification process through the second step (FIG. 3B). The second step used algorithms trained by two methods, namely Linear discriminant analysis (LDA) and Non-linear discriminant analysis (NLDA) (FIG. 3B). LDA analysis was performed using the SPSS 15.0 software in a stepwise approach, since it was unknown if the variables and samples met the conditions required for an LDA. The stepwise approach was chosen, because it simultaneously identified the combination of variables that gave the greatest classification certainty and satisfied the required conditions for an LDA. For NLDA, a genetic algorithm-based method to evolve a set of mathematical functions, resulting in either linear or nonlinear combinations of two or more features was used (Melo et al, *Protein Science*, 2007). This method generated non-linear transforms of combinations of up to four genes that produced single composite scores.

Example 3

Selection of Diagnostic Gene Sets

Figure 4:
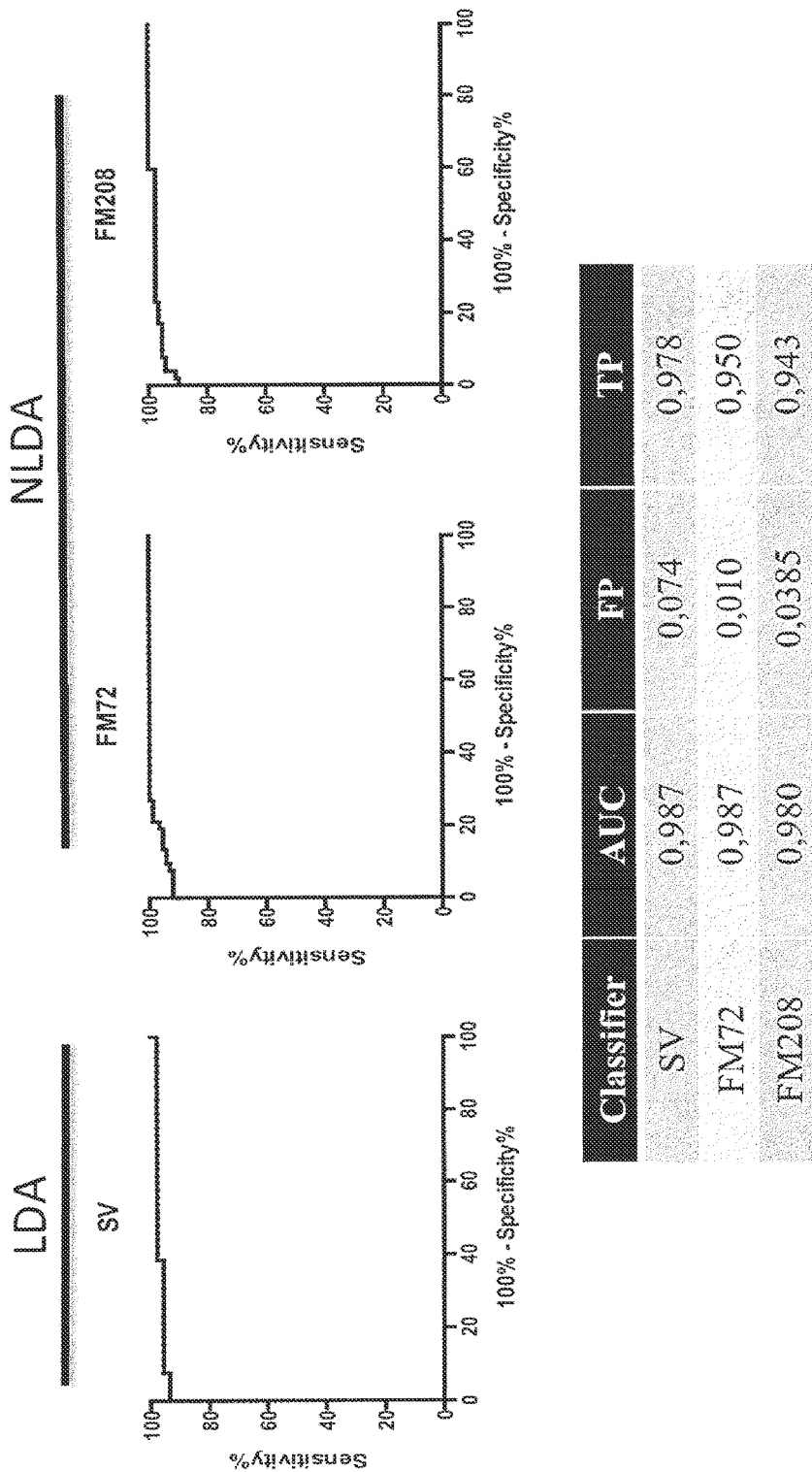
FIG. 4 provides ROC curve graphs of new classifiers developed by the indentification and classification of atypical CT values followed by linear discriminant analysis (LDA) or non-linear discriminant analysis (NLDA). AUC: area under the curve, FP: False positive, TP: True positive.

New gene classifiers generated from both LDA and NLDA strategies, as described in Example 2, were chosen based on ROC curve parameters including area under the curve (AUC), sensitivity, and specificity. Results of representative algorithms obtained by LDA (SV) and NLDA (FM72 and FM208) are shown in FIG. 4. All classifiers showed excellent performance with AUC's greater than 0.98, sensitivities ranging between 94-97.8%, and specificities between 92-99%. Most importantly, the algorithm with best performance (SV; FIG. 4) showed a positive predictive value and negative predictive value of 95.8% and 96.1%, respectively (FIG. 7).

Figure 5:
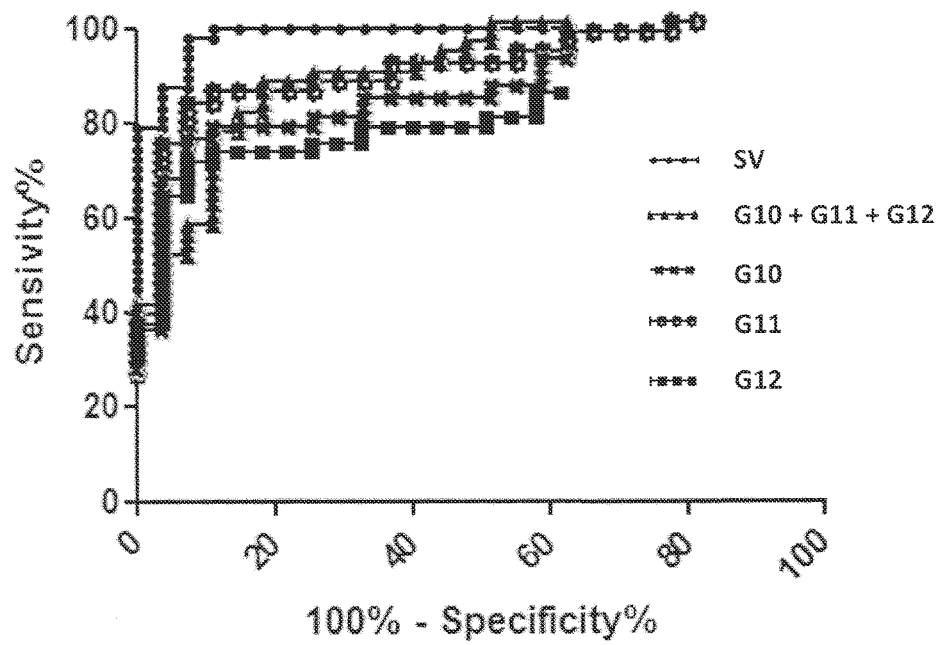
FIG. 5 provides a comparison of AUC of the new classifier (SV) with the best individual genes classifiers and a combination of them (Genes 10, 11, 12) following the method described in FIG. 3. *corresponds to p values<0.05 showing that the SV classifier is significantly superior to the individual genes or a combination of them.
Figure 6:
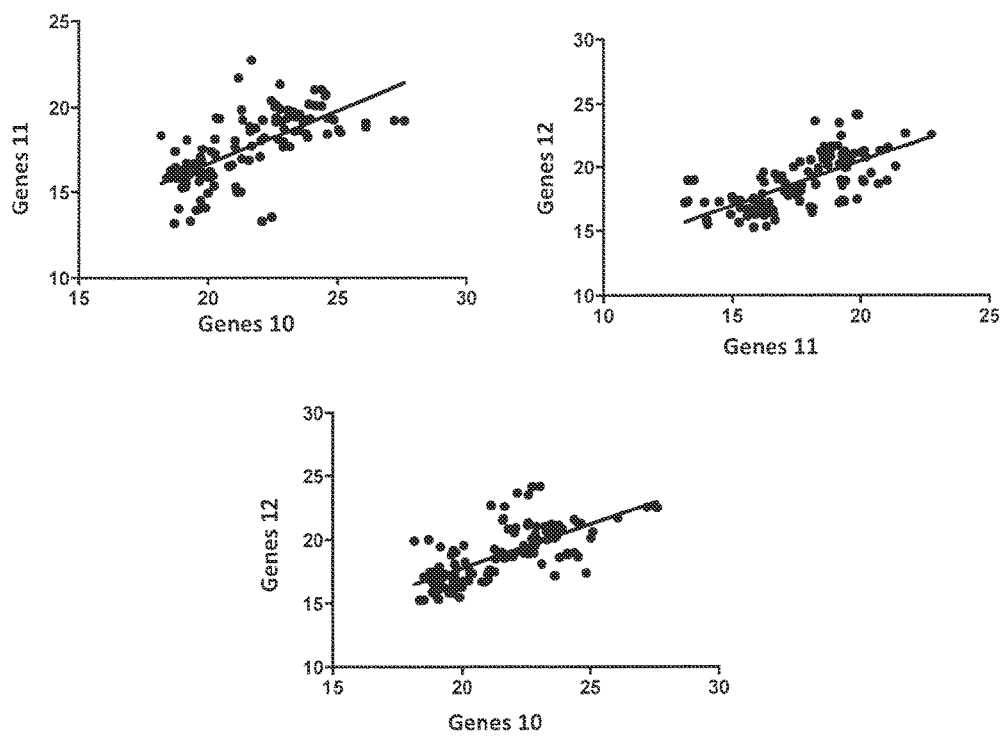
FIG. 6 provides Spearman correlation analysis of the best individual classifying genes, showing that they are closely related, explaining why the combination of them does not improve their performance as gene classifiers.

Although the three genes with best individual performance (CK19, TIMP-1, CLDN1) have been previously shown to be strong biomarkers for thyroid cancer, their combination alone did not account for the performance of these new algorithms. To demonstrate this, these genes, both individually and combined together using the same two-step algorithm strategy described in Example 2 to integrate them, were compared to the new gene combinations identified herein, including the SV gene combination. Remarkably, the combination of the three genes did not modify their performance compared to the genes individually, as shown in FIG. 5. Furthermore, Spearman correlation analysis showed that they are closely related (p<0.001) (FIG. 6), which explained why the combination of these gene did not improve their individual performance. Moreover, the performance of the specific gene combinations identified herein, including the SV gene combination, was statistically superior to CK19, TIMP-1 and CLDN1, both individually and combined (FIG. 5). Without being bound by theory, it is believed that the superiority of the gene combinations described herein is based on the combination of "good" biomarkerswith "poor" biomarkers to achieve maximal classifying ability. This is probably attributable to the fact that in the specific combinations described herein, most of the genes are not related to each other and, therefore, improved performance of the classifier is achieved by the fact that each gene identifies and correctly classifies a different set of samples. Specifically, CK19, TIMP-1 and CLDN1 correctly classified 80% of the cancer samples, whereas other genes used in diagnostic gene combinations of the present invention classified most of the benign samples.

A summary comparing the performance of three gene sets used in classifiers developed as described herein (SV, FM72, and FM208) as compared to Gene 10, Gene 11 and Gene 12, alone or in combination, is shown in FIG. 7. SV includes the following genes: CXCR3, CCR3, CXCL10, CK19, TIMP-1, CLDN-1, CAR, HO-1 and CCR7. FM72 includes the following genes: CCR3, TIMP-1, CAR and XB130. FM208 includes the following genes: CXCL10, TIMP-1, CLDN-1 and CCR7. A comparison of the performance of the various gene sets and classifiers described herein to the Afirma® thyroid FNA analysis test (Veracyte, South San Francisco, Calif.) is shown in FIG. 7.

Example 4

Testing of Gene Classifier with an Independent Testing Set

The accuracy of the selected diagnostic gene markers in detecting cancer or benign tissue was determined against an independent set of data. A new set of samples including 20 cancers (PTC usual type (15), PTC follicular variant (4), and follicular carcinoma (1)) and 39 benign (follicular hyperplasia (28), thyroiditis (7) and, follicular adenoma (4)) tissue samples were used. In this case, a smaller number of cancer samples were included to represent a similar prevalence of cancer seen in fine needle aspiration biopsies in indeterminate thyroid nodules.

Figure 8:
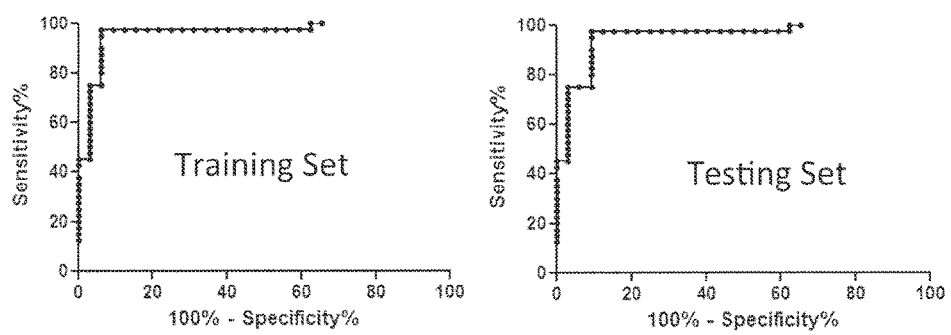
FIG. 8 provides ROC curve graphs and data comparing performance of an independent testing set with the training set using the SV classifier.

Analysis of this independent set using the SV classifier showed excellent performance with an AUC of 0.95, sensitivity 95%, specificity 90%, PPV 83% and NPV 98% (FIG. 8). A reduction in the positive predictive value to 83% was expected given that PPV is dependent of the prevalence of cancer. Similarily, increased negative predictive value depends on the prevalence of benign condition and therefore increased up to 98% in this testing set as compared to the training set (FIG. 8). These results confirm that the markers used in the classifiers described herein produce accurate results that are not overfitted, and provide reliable new diagnostic assays.

Example 5

Testing of Gene Classifier with Second Independent Testing Set Obtained from Fine Needle Aspiration Samples The accuracy of the selected diagnostic gene markers in detecting cancer or benign thyroid nodules was determined against an independent set of samples obtained from fine needle aspiration (FNA). These correspond to the actual clinical setting in which the assay is performed. Since FNA's correspond to a very small sample, it is possible that the reduced cellularity may decrease the performance of the assay. Therefore, the ability of marker sets of the invention to predict the nature of thyroid nodules in FNA samples was tested. The new set of samples included 26 papillary thyroid cancers and 74 benign thyroid nodules. A smaller number of cancer samples were included to represent a similar prevalence of cancer seen in fine needle aspiration biopsies in indeterminate thyroid nodules. Cytopathological diagnosis of FNA samples was used as the gold standard to compare the molecular classification result of the assay.

Analysis of this independent set using the SV classifier showed excellent performance, with a sensitivity of 96%, a specificity of 89%, a PPV of 75% and a NPV of 98% (FIG. 9). These results confirm that the markers used in the classifiers described herein produce accurate results that are not overfitted, and provide reliable confirmation that the assays of the invention have excellent performance in FNA samples routinely used in the clinical setting.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method of treating thyroid cancer in a subject comprising:
   (a) determining an expression level of gene products in a thyroid tissue sample obtained from the subject, the gene products consisting of gene products expressed by the CXCR3, CCR3, CXCL10, CK19, TIMP-1, CLDN-1, CAR, XB-130, HO-1 and CCR7 genes; and
   (b) identifying the thyroid tissue sample as cancerous or benign by correlating the expression levels determined in (a) with the presence or absence of thyroid cancer in the thyroid tissue sample; wherein the correlating is performed using a classifier generated using gene expression data determined for the gene products from a plurality of normal thyroid tissue samples and cancerous thyroid tissue samples;

wherein the thyroid tissue sample is identified as cancerous or benign with:
   a sensitivity of greater than or equal to 92% or greater than or equal to 97%;
   a specificity of greater than or equal to 60% or greater than or equal to 90%;
   a positive predictive value of greater than or equal to 50% or greater than or equal to 90%;
   a negative predictive value of greater than or equal to 92% or greater than or equal to 94%;
   a positive likelihood ratio of greater than or equal to 2 or greater than or equal to 10;
   a positive post-test probability of greater than or equal to 50% or greater than or equal to 80%;
   a negative likelihood ratio of less than or equal to 0.14 or less than or equal to 0.08; or a negative post-test probability of less than or equal to 7.0% or less than or equal to 3.0%; and (c) surgically removing the subject's thyroid, or a portion thereof, if the thyroid tissue sample is identified as cancerous.

2. The method of claim 1, wherein the correlating of (b) comprises comparing the expression levels determined in (a) to gene expression data determined for the gene products in the following two sets of biological samples:
   (i) a plurality of normal thyroid tissue samples; and
   (ii) a plurality of cancerous thyroid tissue samples,
wherein the thyroid tissue sample is identified as cancerous if there is a difference in the expression level of the gene products between the thyroid tissue sample and the gene expression data of (i), or if there is no significant difference in the expression level of the gene products between the thyroid tissue sample and the gene expression date of (ii).

3. The method of claim 1, wherein the classifier identifies atypical CT values followed by linear discriminant analysis.

4. The method of claim 1, wherein the gene products are RNA.

5. The method of claim 1, wherein the gene products are protein.

6. The method of claim 1, further comprising the step of performing a cytological analysis on a thyroid tissue sample obtained from the subject prior to (a) to obtain a preliminary diagnosis.

7. The method of claim 6, wherein samples with a preliminary diagnosis of intermediate or indeterminate are further analyzed by the methods of step (a) and step (b).

8. The method of claim 1, further comprising obtaining the thyroid tissue sample from the subject.

9. A method of treating thyroid cancer, comprising:
   (a) determining an expression level of gene products in a thyroid tissue sample obtained from the subject, the gene products consisting of gene products expressed by the CXCR3, CCR3, CXCL10, CK19, TIMP-1, CLDN-1, CAR, XB-130, HO-1 and CCR7 genes; and
   (b) identifying the thyroid tissue sample as cancerous or benign by correlating the expression levels determined in (a) with the presence or absence of thyroid cancer in the thyroid tissue sample; wherein the correlating is performed using a classifier generated using gene expression data determined for the gene products from a plurality of normal thyroid tissue samples and cancerous thyroid tissue samples; and
   (c) surgically removing the subject's thyroid or a portion thereof, or performing radiation therapy, chemotherapy, or hormone therapy on the subject if the tissue sample is identified as cancerous; or not surgically removing the subject's thyroid or a portion thereof, or performing radiation therapy, chemotherapy, or hormone therapy on the subject if the tissue sample is identified as benign;
   wherein the thyroid tissue sample is diagnosed as cancerous or benign with:
   a sensitivity of greater than or equal to 92% or greater than or equal to 97%;
   a specificity of greater than or equal to 60% or greater than or equal to 90%;
   a positive predictive value of greater than or equal to 50% or greater than or equal to 90%;
   a negative predictive value of greater than or equal to 92% or greater than or equal to 94%;
   a positive likelihood ratio of greater than or equal to 2 or greater than or equal to 10;
   a positive post-test probability of greater than or equal to 50% or greater than or equal to 80%;
   a negative likelihood ratio of less than or equal to 0.14 or less than or equal to 0.08; or
   a negative post-test probability of less than or equal to 7.0% or less than or equal to 3.0%.

10. The method of claim 9, wherein the correlating of (b) comprises comparing the expression levels determined in (a) to gene expression data determined for the gene products in the following two sets of biological samples:
    (i) a plurality of normal thyroid tissue samples; and
    (ii) a plurality of cancerous thyroid tissue samples,
wherein the thyroid tissue sample is identified as cancerous if there is a difference in the expression level of the gene products between the thyroid tissue sample and the gene expression data of (i), or if there is no significant difference in the expression level of the gene products between the thyroid tissue sample and the gene expression date of (ii).

11. The method of claim 9, wherein the classifier identifies atypical CT values followed by linear discriminant analysis.

12. The method of claim 9, wherein the gene products are RNA.

13. The method of claim 9, wherein the gene products are protein.

14. The method of claim 9, further comprising the step of performing a cytological analysis on a thyroid tissue sample obtained from the subject prior to (a) to obtain a preliminary diagnosis.

15. The method of claim 14, wherein samples with a preliminary diagnosis of intermediate or indeterminate are further analyzed by the methods of step (a) and step (b).

16. The method of claim 9, further comprising obtaining the thyroid tissue sample from the subject.

17. A method of treating thyroid cancer in a subject comprising:
    (a) determining an expression level of gene products in a thyroid tissue sample obtained from the subject, the gene products comprising gene products expressed by the CXCR3, CCR3, CXCL10, CK19, CLDN-1, CAR, XB-130, HO-1 and CCR7 genes; and
    (b) diagnosing the thyroid cancer in the subject using a classifier algorithm trained to stratify samples based upon the expression levels of said gene products into two groups identified as:
       (i) an outlier sample having an outlier expression level for at least one of said gene products as compared to a cancer or non-cancer reference expression level for the same gene product, wherein an outlier expression level is defined as a gene expression level that is greater than two standard deviations from the cancer or non-cancer reference expression level for that respective gene product; and
       (ii) a non-outlier sample having no such outlier expression levels for said gene products;
    (c) wherein,
       (i) if the sample is identified as an outlier sample in step (b)(i), a first classifier algorithm is applied to classify the outlier sample as cancerous or non-cancerous, wherein the first algorithm was trained on the expression level of said gene products in a plurality of known cancer or non-cancer outlier samples; and
       (ii) wherein if the tissue sample was identified as a non-outlier sample in step (b), a second classifier algorithm is applied to classify the sample as cancerous or non-cancerous; wherein the second algorithm was trained on the expression level of said gene products in a plurality of known cancer or non-cancer non-outlier samples;

wherein the method further comprises surgically removing the subject's thyroid or a portion thereof, or performing radiation therapy, chemotherapy, or hormone therapy on the subject if the subject is diagnosed with thyroid cancer.

18. The method of claim 17, wherein classification output data from tissue samples classified in steps (c)(i) and (c)(ii) is integrated by an algorithm to report the probability of a cancer or benign result.

19. The method of claim 17, wherein the second classifier algorithm comprises a linear discriminant analysis.

* * * * *

UNITED STATES PATENT AND TRADEMARK OFFICE
CERTIFICATE OF CORRECTION

PATENT NO.         : 10,260,103 B2
APPLICATION NO.    : 14/647284
DATED              : April 16, 2019
INVENTOR(S)        : Hernan Eugenio Gonzalez Diaz et al.

Page 1 of 1

It is certified that error appears in the above-identified patent and that said Letters Patent is hereby corrected as shown below:

In the Claims

At Column 94, Claim number 17, Line number 40:
"the CXCR3, CCR3, CXCL10, CK19, CLDN-1, CAR,"
Should read:
-- the CXCR3, CCR3, CXCL10, CK19, TIMP-1, CLDN-1, CAR, --

Signed and Sealed this
Tenth Day of September, 2019

Andrei Iancu
*Director of the United States Patent and Trademark Office*

SEQUENCE LISTING

```
<160> NUMBER OF SEQ ID NOS: 20

<210> SEQ ID NO 1
<211> LENGTH: 1670
<212> TYPE: DNA
<213> ORGANISM: Homo sapiens

<400> SEQUENCE: 1
ccaaccacaa gcaccaaagc agagggcag gcagcacacc acccagcagc cagagcacca      60
gcccagccat ggtccttgag gtgagtgacc accaagtgct aaatgacgcc gaggttgccg     120
ccctcctgga gaacttcagc tcttcctatg actatggaga aaacgagagt gactcgtgct    180
```

| | |
|---|---|
| gtacctcccc gccctgccca caggacttca gcctgaactt cgaccgggcc ttcctgccag | 240 |
| ccctctacag cctcctcttt ctgctggggc tgctgggcaa cggcgcggtg gcagccgtgc | 300 |
| tgctgagccg gcggacagcc ctgagcagca ccgacacctt cctgctccac ctagctgtag | 360 |
| cagacacgct gctggtgctg acactgccgc tctgggcagt ggacgctgcc gtccagtggg | 420 |
| tctttggctc tggcctctgc aaagtggcag gtgccctctt caacatcaac ttctacgcag | 480 |
| gagccctcct gctggcctgc atcagctttg accgctacct gaacatagtt catgccaccc | 540 |
| agctctaccg ccgggggccc ccggcccgcg tgaccctcac ctgcctggct gtctgggggc | 600 |
| tctgcctgct tttcgccctc ccagacttca tcttcctgtc ggcccaccac gacgagcgcc | 660 |
| tcaacgccac ccactgccaa tacaacttcc cacaggtggg ccgcacggct ctgcgggtgc | 720 |
| tgcagctggt ggctggcttt ctgctgcccc tgctggtcat ggcctactgc tatgcccaca | 780 |
| tcctggccgt gctgctggtt ccaggggcca gcggcgcct gcgggccatg cggctggtgg | 840 |
| tggtggtcgt ggtggccttt gccctctgct gaccccta tcacctggtg gtgctggtgg | 900 |
| acatcctcat ggacctgggc gctttggccc gcaactgtgg ccgagaaagc agggtagacg | 960 |
| tggccaagtc ggtcacctca ggcctgggct acatgcactg ctgcctcaac ccgctgctct | 1020 |
| atgcctttgt aggggtcaag ttccgggagc ggatgtggat gctgctcttg cgcctgggct | 1080 |
| gccccaacca gagagggctc cagaggcagc atcgtcttc cgccgggat tcatcctggt | 1140 |
| ctgagacctc agaggcctcc tactcgggct tgtgaggccg gaatccgggc tccccttcg | 1200 |
| cccacagtct gacttccccg cattccaggc tcctccctcc ctctgccggc tctggctctc | 1260 |
| cccaatatcc tcgctcccgg gactcactgg cagccccagc accaccaggt ctcccgggaa | 1320 |
| gccaccctcc cagctctgag gactgcacca ttgctgctcc ttagctgcca agccccatcc | 1380 |
| tgccgcccga ggtggctgcc tggagcccca ctgcccttct catttggaaa ctaaaacttc | 1440 |
| atcttcccca agtgcgggga gtacaaggca tggcgtagag ggtgctgccc catgaagcca | 1500 |
| cagcccaggc tccagctca gcagtgactg tggccatggt ccccaagacc tctatatttg | 1560 |
| ctcttttatt tttatgtcta aaatcctgct taaaactttt caataaacaa gatcgtcagg | 1620 |
| accaaaaaaa aaaaaaaaa aaaaaaaaaa aaaaaaaaa aaaaaaaaa | 1670 |

<210> SEQ ID NO 2
<211> LENGTH: 368
<212> TYPE: PRT
<213> ORGANISM: Homo sapiens

<400> SEQUENCE: 2

Met Val Leu Glu Val Ser Asp His Gln Val Leu Asn Asp Ala Glu Val
1               5                   10                  15

Ala Ala Leu Leu Glu Asn Phe Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

```
Ala Ala Val Gln Trp Val Phe Gly Ser Gly Leu Cys Lys Val Ala Gly
            115                 120                 125
Ala Leu Phe Asn Ile Asn Phe Tyr Ala Gly Ala Leu Leu Leu Ala Cys
        130                 135                 140
Ile Ser Phe Asp Arg Tyr Leu Asn Ile Val His Ala Thr Gln Leu Tyr
145                 150                 155                 160
Arg Arg Gly Pro Pro Ala Arg Val Thr Leu Thr Cys Leu Ala Val Trp
                165                 170                 175
Gly Leu Cys Leu Leu Phe Ala Leu Pro Asp Phe Ile Phe Leu Ser Ala
            180                 185                 190
His His Asp Glu Arg Leu Asn Ala Thr His Cys Gln Tyr Asn Phe Pro
        195                 200                 205
Gln Val Gly Arg Thr Ala Leu Arg Val Leu Gln Leu Val Ala Gly Phe
    210                 215                 220
Leu Leu Pro Leu Leu Val Met Ala Tyr Cys Tyr Ala His Ile Leu Ala
225                 230                 235                 240
Val Leu Leu Val Ser Arg Gly Gln Arg Arg Leu Arg Ala Met Arg Leu
                245                 250                 255
Val Val Val Val Val Ala Phe Ala Leu Cys Trp Thr Pro Tyr His
            260                 265                 270
Leu Val Val Leu Val Asp Ile Leu Met Asp Leu Gly Ala Leu Ala Arg
        275                 280                 285
Asn Cys Gly Arg Glu Ser Arg Val Asp Val Ala Lys Ser Val Thr Ser
    290                 295                 300
Gly Leu Gly Tyr Met His Cys Cys Leu Asn Pro Leu Leu Tyr Ala Phe
305                 310                 315                 320
Val Gly Val Lys Phe Arg Glu Arg Met Trp Met Leu Leu Leu Arg Leu
                325                 330                 335
Gly Cys Pro Asn Gln Arg Gly Leu Gln Arg Gln Pro Ser Ser Ser Arg
            340                 345                 350
Arg Asp Ser Ser Trp Ser Glu Thr Ser Glu Ala Ser Tyr Ser Gly Leu
        355                 360                 365

<210> SEQ ID NO 3
<211> LENGTH: 1796
<212> TYPE: DNA
<213> ORGANISM: Homo sapiens

<400> SEQUENCE: 3
ctgatggtat ctctgtttca ggagtggtga cgcctaagct atcactggac atatcaagga     60
cttcactaaa ttagcaggta ccactggtct tcttgtgctt atccgggcaa gaacttatcg    120
aaatacaata gaagttttta cttagaagag attttcagca gatgagaagc tggtaacaga    180
gaccaaaata gtttggagac taaagaatca ttgcacattt cactgctgag ttgtattgga    240
gaagtgaaat gacaacctca ctagatacag ttgagacctt tggtaccaca tcctactatg    300
atgacgtggg cctgctctgt gaaaaagctg ataccagagc actgatggcc cagtttgtgc    360
ccccgctgta ctccctggtg ttcactgtgg gcctcttggg caatgtggtg gtggtgatga    420
tcctcataaa ataaggagg ctccgaatta tgaccaacat ctacctgctc aacctggcca    480
tttcggacct gctcttcctc gtcacccttc cattctggat ccactatgtc aggggcata    540
actgggtttt tggccatggc atgtgtaagc tcctctcagg gttttatcac acaggcttgt    600
acagcgagat cttttcata atcctgctga caatcgacag gtacctggcc attgtccatg    660
ctgtgtttgc cttcgagcc cggactgtca cttttggtgt catcaccagc atcgtcacct    720
```

-continued

```
gggcctggc  agtgctagca  gctcttcctg  aatttatctt  ctatgagact  gaagagttgt   780
ttgaagagac  tctttgcagt  gctctttacc  cagaggatac  agtatatagc  tggaggcatt   840
tccacactct  gagaatgacc  atcttctgtc  tcgttctccc  tctgctcgtt  atggccatct   900
gctacacagg  aatcatcaaa  acgctgctga  ggtgccccag  taaaaaaaag  tacaaggcca   960
tccggctcat  ttttgtcatc  atggcggtgt  ttttcatttt  ctggacaccc  tacaatgtgg  1020
ctatccttct  ctcttcctat  caatccatct  tatttggaaa  tgactgtgag  cggagcaagc  1080
atctggacct  ggtcatgctg  gtgacagagg  tgatcgccta  ctcccactgc  tgcatgaacc  1140
cggtgatcta  cgcctttgtt  ggagagaggt  tccggaagta  cctgcgccac  ttcttccaca  1200
ggcacttgct  catgcacctg  gcagataca   tcccattcct  tcctagtgag  aagctggaaa  1260
gaaccagctc  tgtctctcca  tccacagcag  agccggaact  ctctattgtg  ttttaggtca  1320
gatgcagaaa  attgcctaaa  gaggaaggac  caaggagatg  aagcaaacac  attaagcctt  1380
ccacactcac  ctctaaaaca  gtccttcaaa  cttccagtgc  aacactgaag  ctcttgaaga  1440
cactgaaata  tacacacagc  agtagcagta  gatgcatgta  ccctaaggtc  attaccacag  1500
gccaggggct  gggcagcgta  ctcatcatca  accctaaaaa  gcagagcttt  gcttctctct  1560
ctaaaatgag  ttacctacat  tttaatgcac  ctgaatgtta  gatagttact  atatgccgct  1620
acaaaaaggt  aaaacttttt  atattttata  cattaacttc  agccagctat  tgatataaat  1680
aaaacatttt  cacacaatac  aataagttaa  ctattttatt  ttctaatgtg  cctagttctt  1740
tccctgctta  atgaaaagct  tgttttttca  gtgtgaataa  ataatcgtaa  gcaaca       1796
```

<210> SEQ ID NO 4
<211> LENGTH: 355
<212> TYPE: PRT
<213> ORGANISM: Homo sapiens

<400> SEQUENCE: 4

```
Met Thr Thr Ser Leu Asp Thr Val Glu Thr Phe Gly Thr Thr Ser Tyr
  1               5                  10                  15

Tyr Asp Asp Val Gly Leu Leu Cys Glu Lys Ala Asp Thr Arg Ala Leu
             20                  25                  30

Met Ala Gln Phe Val Pro Pro Leu Tyr Ser Leu Val Phe Thr Val Gly
         35                  40                  45

Leu Leu Gly Asn Val Val Val Val Met Ile Leu Ile Lys Tyr Arg Arg
     50                  55                  60

Leu Arg Ile Met Thr Asn Ile Tyr Leu Leu Asn Leu Ala Ile Ser Asp
 65                  70                  75                  80

Leu Leu Phe Leu Val Thr Leu Pro Phe Trp Ile His Tyr Val Arg Gly
                 85                  90                  95

His Asn Trp Val Phe Gly His Gly Met Cys Lys Leu Leu Ser Gly Phe
            100                 105                 110

Tyr His Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
            180                 185                 190
```

```
Tyr Ser Trp Arg His Phe His Thr Leu Arg Met Thr Ile Phe Cys Leu
            195                 200                 205

Val Leu Pro Leu Leu Val Met Ala Ile Cys Tyr Thr Gly Ile Ile Lys
        210                 215                 220

Thr Leu Leu Arg Cys Pro Ser Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
            260                 265                 270

Cys Glu Arg Ser Lys His Leu Asp Leu Val Met Leu Val Thr Glu Val
        275                 280                 285

Ile Ala Tyr Ser His Cys Cys Met Asn Pro Val Ile Tyr Ala Phe Val
        290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355

<210> SEQ ID NO 5
<211> LENGTH: 1227
<212> TYPE: DNA
<213> ORGANISM: Homo sapiens

<400> SEQUENCE: 5
ctttgcagat aaatatggca cactagcccc acgttttctg agacattcct caattgctta      60
gacatattct gagcctacag cagaggaacc tccagtctca gcaccatgaa tcaaactgcc     120
attctgattt gctgccttat cttctgact ctaagtggca ttcaaggagt acctctctct      180
agaactgtac gctgtacctg catcagcatt agtaatcaac ctgttaatcc aaggtcttta     240
gaaaaacttg aaattattcc tgcaagccaa ttttgtccac gtgttgagat cattgctaca     300
atgaaaaaga agggtgagaa gagatgtctg aatccagaat cgaaggccat caagaattta     360
ctgaaagcag ttagcaagga aaggtctaaa agatctcctt aaaaccagag gggagcaaaa     420
tcgatgcagt gcttccaagg atggaccaca cagaggctgc ctctcccatc acttccctac     480
atggagtata tgtcaagcca taattgttct tagtttgcag ttacactaaa aggtgaccaa     540
tgatggtcac caaatcagct gctactactc ctgtaggaag gttaatgttc atcatcctaa     600
gctattcagt aataactcta ccctggcact ataatgtaag ctctactgag gtgctatgtt     660
cttagtggat gttctgaccc tgcttcaaat atttccctca cctttcccat cttccaaggg     720
tactaaggaa tctttctgct tgggggttta tcagaattct cagaatctca ataactaaa      780 aggtatgcaa tcaaatctgc ttttaaaga atgctcttta cttcatggac ttccactgcc     840
atcctcccaa ggggcccaaa ttctttcagt ggctacctac atacaattcc aaacacatac     900
aggaaggtag aaatatctga aaatgtatgt gtaagtattc ttatttaatg aaagactgta     960
caaagtagaa gtcttagatg tatatatttc ctatattgtt ttcagtgtac atggaataac    1020
atgtaattaa gtactatgta tcaatgagta acaggaaaat tttaaaaata cagatagata    1080
tatgctctgc atgttacata agataaatgt gctgaatggt tttcaaaata aaaatgaggt    1140
```

```
actctcctgg aaatattaag aaagactatc taaatgttga aagatcaaaa ggttaataaa      1200
gtaattataa ctaagaaaaa aaaaaaa                                          1227

<210> SEQ ID NO 6
<211> LENGTH: 98
<212> TYPE: PRT
<213> ORGANISM: Homo sapiens

<400> SEQUENCE: 6

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 7
<211> LENGTH: 1490
<212> TYPE: DNA
<213> ORGANISM: Homo sapiens

<400> SEQUENCE: 7
agatatccgc ccctgacacc attcctccct tccccctcc accggccgcg ggcataaaag       60
gcgccaggtg agggcctcgc cgctcctccc gcgaatcgca gcttctgaga ccagggttgc     120
tccgtccgtg ctccgcctcg ccatgacttc ctacagctat cgccagtcgt cggccacgtc     180
gtccttcgga ggcctgggcg gcggctccgt gcgttttggg ccggggtcg cctttcgcgc      240 gcccagcatt cacgggggct ccggcggccg cggcgtatcc gtgtcctccg cccgctttgt     300
gtcctcgtcc tcctcggggg cctacggcgg cggctacggc ggcgtcctga ccgcgtccga     360
cgggctgctg gcgggcaacg agaagctaac catgcagaac ctcaacgacc gcctggcctc     420
ctacctggac aaggtgcgcg ccctggaggc ggccaacggc gagctagagg tgaagatccg     480
cgactggtac cagaagcagg ggcctgggcc ctcccgcgac tacagccact actacacgac     540
catccaggac ctgcgggaca gattcttggt gccaccatt gagaactcca ggattgtcct      600
gcagatcgac aatgcccgtc tggctgcaga tgacttccga accaagtttg agacggaaca     660
ggctctgcgc atgagcgtgg aggccgacat caacggcctg cgcagggtgc tggatgagct     720
gaccctggcc aggaccgacc tggagatgca gatcgaaggc ctgaaggaag agctggccta     780
cctgaagaag aaccatgagg aggaaatcag tacgctgagg ggccaagtgg gaggccaggt     840
cagtgtggag gtggattccg ctccgggcac cgatctcgcc aagatcctga gtgacatgcg     900
aagccaatat gaggtcatgg ccgagcagaa ccggaaggat gctgaagcct ggttcaccag     960
ccggactgaa gaattgaacc gggaggtcgc tggccacacg gagcagctcc agatgagcag    1020
gtccgaggtt actgacctgc ggcgcaccct tcagggtctt gagattgagc tgcagtcaca    1080
gctgagcatg aaagctgcct tggaagacac actggcagaa acgaggcgc gctttggagc     1140 ccagctggcg catatccagg cgctgatcag cggtattgaa gcccagctgg cgatgtgcg     1200
```

```
agctgatagt gagcggcaga atcaggagta ccagcggctc atggacatca agtcgcggct    1260
ggagcaggag attgccacct accgcagcct gctcgaggga caggaagatc actacaacaa    1320
tttgtctgcc tccaaggtcc tctgaggcag caggctctgg ggcttctgct gtcctttgga    1380
gggtgtcttc tgggtagagg gatgggaagg aagggaccct tacccccggc tcttctcctg    1440
acctgccaat aaaaatttat ggtccaaggg aaaaaaaaaa aaaaaaaaa                1490
```

<210> SEQ ID NO 8
<211> LENGTH: 400
<212> TYPE: PRT
<213> ORGANISM: Homo sapiens

<400> SEQUENCE: 8

```
Met Thr Ser Tyr Ser Tyr Arg Gln Ser Ser Ala Thr Ser Ser Phe Gly
1               5                   10                  15

Gly Leu Gly Gly Gly Ser Val Arg Phe Gly Pro Gly Val Ala Phe Arg
            20                  25                  30

Ala Pro Ser Ile His Gly Gly Ser Gly Gly Arg Gly Val Ser Val Ser
        35                  40                  45

Ser Ala Arg Phe Val Ser Ser Ser Ser Gly Ala Tyr Gly Gly Gly
    50                  55                  60

Tyr Gly Gly Val Leu Thr Ala Ser Asp Gly Leu Leu Ala Gly Asn Glu
65                  70                  75                  80

Lys Leu Thr Met Gln Asn Leu Asn Asp Arg Leu Ala Ser Tyr Leu Asp
                85                  90                  95

Lys Val Arg Ala Leu Glu Ala Ala Asn Gly Glu Leu Glu Val Lys Ile
            100                 105                 110

Arg Asp Trp Tyr Gln Lys Gln Gly Pro Gly Pro Ser Arg Asp Tyr Ser
        115                 120                 125

His Tyr Tyr Thr Thr Ile Gln Asp Leu Arg Asp Lys Ile Leu Gly Ala
    130                 135                 140

Thr Ile Glu Asn Ser Arg Ile Val Leu Gln Ile Asp Asn Ala Arg Leu
145                 150                 155                 160

Ala Ala Asp Asp Phe Arg Thr Lys Phe Glu Thr Glu Gln Ala Leu Arg
                165                 170                 175

Met Ser Val Glu Ala Asp Ile Asn Gly Leu Arg Arg Val Leu Asp Glu
            180                 185                 190

Leu Thr Leu Ala Arg Thr Asp Leu Glu Met Gln Ile Glu Gly Leu Lys
        195                 200                 205

Glu Glu Leu Ala Tyr Leu Lys Lys Asn His Glu Glu Glu Ile Ser Thr
    210                 215                 220

Leu Arg Gly Gln Val Gly Gly Gln Val Ser Val Glu Val Asp Ser Ala
225                 230                 235                 240

Pro Gly Thr Asp Leu Ala Lys Ile Leu Ser Asp Met Arg Ser Gln Tyr
                245                 250                 255

Glu Val Met Ala Glu Gln Asn Arg Lys Asp Ala Glu Ala Trp Phe Thr
            260                 265                 270

Ser Arg Thr Glu Glu Leu Asn Arg Glu Val Ala Gly His Thr Glu Gln
        275                 280                 285

Leu Gln Met Ser Arg Ser Glu Val Thr Asp Leu Arg Arg Thr Leu Gln
    290                 295                 300

Gly Leu Glu Ile Glu Leu Gln Ser Gln Leu Ser Met Lys Ala Ala Leu
305                 310                 315                 320
```

```
Glu Asp Thr Leu Ala Glu Thr Glu Ala Arg Phe Gly Ala Gln Leu Ala
                325                 330                 335
His Ile Gln Ala Leu Ile Ser Gly Ile Glu Ala Gln Leu Gly Asp Val
                340                 345                 350
Arg Ala Asp Ser Glu Arg Gln Asn Gln Glu Tyr Gln Arg Leu Met Asp
                355                 360                 365
Ile Lys Ser Arg Leu Glu Gln Glu Ile Ala Thr Tyr Arg Ser Leu Leu
        370                 375                 380
Glu Gly Gln Glu Asp His Tyr Asn Asn Leu Ser Ala Ser Lys Val Leu
385                 390                 395                 400

<210> SEQ ID NO 9
<211> LENGTH: 931
<212> TYPE: DNA
<213> ORGANISM: Homo sapiens

<400> SEQUENCE: 9
tttcgtcggc cgcccctttg gcttctgcac tgatggtggg tggatgagta atgcatccag      60
gaagcctgga ggcctgtggt tccgcacccc gctgccaccc ccgcccctag cgtggacatt    120
tatcctctag cgctcaggcc ctgccgccat cgccgcagat ccagcgccca gagagacacc    180
agagaaccca ccatggcccc ctttgagccc ctggcttctg gcatcctgtt gttgctgtgg    240
ctgatagccc ccagcagggc ctgcacctgt gtcccacccc acccacagac ggccttctgc    300
aattccgacc tcgtcatcag ggccaagttc gtggggacac agaagtcaa ccagaccacc    360
ttataccagc gttatgagat caagatgacc aagatgtata agggttccaa gccttaggg     420
gatgccgctg acatccggtt cgtctacacc ccgccatgg agagtgtctg cggatacttc     480
cacaggtccc acaaccgcag cgaggagttt ctcattgctg aaaactgca ggatggactc     540
ttgcacatca ctacctgcag ttttgtggct ccctggaaca gcctgagctt agctcagcgc     600
cggggcttca ccaagaccta cactgttggc tgtgaggaat gcacagtgtt tccctgttta     660
tccatcccct gcaaactgca gagtggcact cattgcttgt ggacggacca gctcctccaa    720
ggctctgaaa agggcttcca gtcccgtcac cttgcctgcc tgcctcggga gccagggctg    780
tgcacctggc agtccctgcg gtcccagata gcctgaatcc tgcccggagt ggaagctgaa    840
gcctgcacag tgtccaccct gttcccactc ccatctttct tccggacaat gaaataaaga    900
gttaccaccc agcagaaaaa aaaaaaaaaa a                                    931

<210> SEQ ID NO 10
<211> LENGTH: 207
<212> TYPE: PRT
<213> ORGANISM: Homo sapiens

<400> SEQUENCE: 10

Met Ala Pro Phe Glu Pro Leu Ala Ser Gly Ile Leu Leu Leu Leu Trp
1                   5                   10                  15
Leu Ile Ala Pro Ser Arg Ala Cys Thr Cys Val Pro Pro His Pro Gln
                20                  25                  30
Thr Ala Phe Cys Asn Ser Asp Leu Val Ile Arg Ala Lys Phe Val Gly
            35                  40                  45
Thr Pro Glu Val Asn Gln Thr Thr Leu Tyr Gln Arg Tyr Glu Ile Lys
        50                  55                  60
Met Thr Lys Met Tyr Lys Gly Phe Gln Ala Leu Gly Asp Ala Ala Asp
65                  70                  75                  80
```

```
Ile Arg Phe Val Tyr Thr Pro Ala Met Glu Ser Val Cys Gly Tyr Phe
                85                  90                  95
His Arg Ser His Asn Arg Ser Glu Glu Phe Leu Ile Ala Gly Lys Leu
            100                 105                 110
Gln Asp Gly Leu Leu His Ile Thr Thr Cys Ser Phe Val Ala Pro Trp
            115                 120                 125
Asn Ser Leu Ser Leu Ala Gln Arg Arg Gly Phe Thr Lys Thr Tyr Thr
        130                 135                 140
Val Gly Cys Glu Glu Cys Thr Val Phe Pro Cys Leu Ser Ile Pro Cys
145                 150                 155                 160
Lys Leu Gln Ser Gly Thr His Cys Leu Trp Thr Asp Gln Leu Leu Gln
                165                 170                 175
Gly Ser Glu Lys Gly Phe Gln Ser Arg His Leu Ala Cys Leu Pro Arg
            180                 185                 190
Glu Pro Gly Leu Cys Thr Trp Gln Ser Leu Arg Ser Gln Ile Ala
            195                 200                 205

<210> SEQ ID NO 11
<211> LENGTH: 3452
<212> TYPE: DNA
<213> ORGANISM: Homo sapiens

<400> SEQUENCE: 11
gtctcagttc ccgagcctgg gagcaaccgc agcttctagt atccagactc cagcgccgcc    60
ccgggcgcgg accccaaccc cgacccagag cttctccagc ggcggcgcag cgagcagggc   120
tccccgcctt aacttcctcc gcggggccca gccaccttcg ggagtccggg ttgcccacct   180
gcaaactctc cgccttctgc acctgccacc cctgagccag cgcgggcgcc cgagcgagtc   240
atggccaacg cggggctgca gctgttgggc ttcattctcg ccttcctggg atggatcggc   300
gccatcgtca gcactgccct gccccagtgg aggatttact cctatgccgg cgacaacatc   360
gtgaccgccc aggccatgta cgaggggctg tggatgtcct gcgtgtcgca gagcaccggg   420
cagatccagt gcaaagtctt tgactccttg ctgaatctga gcagcacatt gcaagcaacc   480
cgtgccttga tggtggttgg catcctcctg ggagtgatag caatctttgt ggccaccgtt   540
ggcatgaagt gtatgaagtg cttggaagac gatgaggtgc agaagatgag gatggctgtc   600
attgggggtg cgatatttct tcttgcaggt ctggctattt tagttgccac agcatgggtat   660
ggcaatagaa tcgttcaaga attctatgac cctatgaccc cagtcaatgc caggtacgaa   720
tttggtcagg ctctcttcac tggctgggct gctgcttctc tctgccttct gggaggtgcc   780
ctactttgct gttcctgtcc ccgaaaaaca acctcttacc caacaccaag gcccgtatcca   840
aaacctgcac cttccagcgg gaaagactac gtgtgacaca gaggcaaaag gagaaaatca   900
tgttgaaaca aaccgaaaat ggacattgag atactatcat taacattagg acctagaat   960
tttgggtatt gtaatctgaa gtatggtatt acaaaacaaa caaacaaaca aaaacccat   1020
gtgttaaaat actcagtgct aaacatggct taatcttatt ttatcttctt tcctcaatat  1080
aggagggaag atttttccat ttgtattact gcttcccatt gagtaatcat actcaactgg  1140
gggaaggggt gctccttaaa tatatataga tatgtatata tacatgtttt tctattaaaa  1200
atagacagta aaatactatt ctcattatgt tgatactagc atacttaaaa tatctctaaa  1260
ataggtaaat gtatttaatt ccatattgat gaagatgttt attggtatat ttctttttc   1320
gtctatatat acatatgtaa cagtcaaata tcatttactc ttcttcatta gctttgggtg  1380
```

```
cctttgccac aagacctagc ctaatttacc aaggatgaat tctttcaatt cttcatgcgt    1440 gccctttca tatacttatt ttattttta ccataatctt atagcacttg catcgttatt     1500
aagcccttat ttgttttgtg tttcattggt ctctatctcc tgaatctaac acatttcata   1560
gcctacattt tagtttctaa agccaagaag aatttattac aaatcagaac tttggaggca   1620
aatctttctg catgaccaaa gtgataaatt cctgttgacc ttcccacaca atccctgtac   1680
tctgacccat agcactcttg tttgctttga aaatatttgt ccaattgagt agctgcatgc   1740 tgttcccca ggtgttgtaa cacaacttta ttgattgaat ttttaagcta cttattcata   1800
gttttatatc ccctaaaact accttttgt tccccattcc ttaattgtat tgttttccca   1860
agtgtaatta tcatgcgttt tatatcttcc taataaggtg tggtctgttt gtctgaacaa   1920
agtgctagac tttctggagt gataatctgg tgacaaatat tctctctgta gctgtaagca   1980
agtcacttaa tctttctacc tctttttct atctgccaaa ttgagataat gatacttaac    2040
cagttagaag aggtagtgtg aatattaatt agtttatatt actctcattc tttgaacatg   2100
aactatgcct atgtagtgtc tttatttgct cagctggctg agacactgaa gaagtcactg   2160
aacaaaacct acacacgtac cttcatgtga ttcactgcct tcctctctct accagtctat   2220
ttccactgaa caaaacctac acacatacct tcatgtggtt cagtgccttc ctctctctac   2280
cagtctattt ccactgaaca aaacctacgc acataccttc atgtggctca gtgccttcct   2340
ctctctacca gtctatttcc attctttcag ctgtgtctga catgtttgtg ctctgttcca   2400
ttttaacaac tgctcttact tttccagtct gtacagaatg ctatttcact tgagcaagat   2460
gatgtaatgg aaagggtgtt ggcattggtg tctggagacc tggatttgag tcttggtgct   2520
atcaatcacc gtctgtgttt gagcaaggca tttggctgct gtaagcttat tgcttcatct   2580
gtaagcggtg gtttgtaatt cctgatcttc ccacctcaca gtgatgttgt ggggatccag   2640
tgagatagaa tacatgtaag tgtggttttg taatttaaaa agtgctatac taagggaaag   2700
aattgaggaa ttaactgcat acgttttggt gttgcttttc aaatgtttga aaacaaaaaa   2760
aatgttaaga aatgggtttc ttgccttaac cagtctctca agtgatgaga cagtgaagta   2820
aaattgagtg cactaaacaa ataagattct gaggaagtct tatcttctgc agtgagtatg   2880
gcccgatgct ttctgtggct aaacagatgt aatgggaaga aataaaagcc tacgtgttgg   2940
taaatccaac agcaagggag attttttgaat cataataact cataaggtgc tatctgttca   3000
gtgatgccct cagagctctt gctgttagct ggcagctgac gctgctagga tagttagttt   3060
ggaaatggta cttcataata aactacacaa ggaaagtcag ccactgtgtc ttatgaggaa   3120
ttggacctaa taaattttag tgtgccttcc aaacctgaga atatatgctt ttggaagtta   3180
aaatttaaat ggcttttgcc acatacatag atcttcatga tgtgtgagtg taattccatg   3240
tggatatcag ttaccaaaca ttacaaaaaa attttatggc ccaaaatgac caacgaaatt   3300
gttacaatag aatttatcca attttgatct ttttatattc ttctaccaca cctggaaaca   3360
gaccaataga catttggggg ttttataata ggaatttgta taaagcatta ctctttttca   3420
ataaattgtt ttttaatttta aaaaaaggat ta                                3452
```

<210> SEQ ID NO 12
<211> LENGTH: 211
<212> TYPE: PRT
<213> ORGANISM: Homo sapiens

<400> SEQUENCE: 12

```
Met Ala Asn Ala Gly Leu Gln Leu Leu Gly Phe Ile Leu Ala Phe Leu
1               5                   10                  15
Gly Trp Ile Gly Ala Ile Val Ser Thr Ala Leu Pro Gln Trp Arg Ile
            20                  25                  30
Tyr Ser Tyr Ala Gly Asp Asn Ile Val Thr Ala Gln Ala Met Tyr Glu
        35                  40                  45
Gly Leu Trp Met Ser Cys Val Ser Gln Ser Thr Gly Gln Ile Gln Cys
    50                  55                  60
Lys Val Phe Asp Ser Leu Leu Asn Leu Ser Ser Thr Leu Gln Ala Thr
65                  70                  75                  80
Arg Ala Leu Met Val Val Gly Ile Leu Leu Gly Val Ile Ala Ile Phe
                85                  90                  95
Val Ala Thr Val Gly Met Lys Cys Met Lys Cys Leu Glu Asp Asp Glu
            100                 105                 110
Val Gln Lys Met Arg Met Ala Val Ile Gly Gly Ala Ile Phe Leu Leu
        115                 120                 125
Ala Gly Leu Ala Ile Leu Val Ala Thr Ala Trp Tyr Gly Asn Arg Ile
    130                 135                 140
Val Gln Glu Phe Tyr Asp Pro Met Thr Pro Val Asn Ala Arg Tyr Glu
145                 150                 155                 160
Phe Gly Gln Ala Leu Phe Thr Gly Trp Ala Ala Ser Leu Cys Leu
                165                 170                 175
Leu Gly Gly Ala Leu Leu Cys Cys Ser Cys Pro Arg Lys Thr Thr Ser
            180                 185                 190
Tyr Pro Thr Pro Arg Pro Tyr Pro Lys Pro Ala Pro Ser Ser Gly Lys
195                 200                 205
Asp Tyr Val
210
```

<210> SEQ ID NO 13
<211> LENGTH: 1669
<212> TYPE: DNA
<213> ORGANISM: Homo sapiens

<400> SEQUENCE: 13

```
ggcaacccca cgcggctgga gaagccggcg ctcgcagccc ggcccgggcc gctgccggaa      60
gtgacgcgag ttcacctgcc gagcgggggc tgggaggagg ggcggagggt gcagaggtgc     120
cgccgccgcc gcgagccagt cgggagcgcg cgaggcgcgg ggagcctggg accaggagcg     180
agagccgcct acctgcagcc gccgcccacg gcacggcagc caccatggcg ctcctgctgt     240
gcttcgtgct cctgtgcgga gtagtggatt tcgccagaag tttgagtatc actactcctg     300
aagagatgat tgaaaaagcc aaggggaaa ctgcctatct gccatgcaaa tttacgctta     360
gtcccgaaga ccagggaccg ctggacatcg agtggctgat atcaccagct gataatcaga     420
aggtggatca agtgattatt ttatattctg agacaaaat ttatgatgac tactatccag     480
atctgaaagg ccgagtacat tttacgagta atgatctcaa atctggtgat gcatcaataa     540
atgtaacgaa tttacaactg tcagatattg cacatatca gtgcaaagtg aaaaaagctc     600
ctggtgttgc aaataagaag attcatctgg tagttcttgt taagccttca ggtgcgagat     660
gttacgttga tggatctgaa gaattggaa gtgactttaa gataaaatgt gaaccaaaag     720
aaggttcact tccattacag tatgagtggc aaaaattgtc tgactcacag aaaatgccca     780
cttcatggtt agcagaaatg acttcatctg ttatatctgt aaaaaatgcc tcttctgagt     840
```

-continued

```
actctgggac atacagctgt acagtcagaa acagagtggg ctctgatcag tgcctgttgc    900
gtctaaacgt tgtccctcct tcaaataaag ctggactaat tgcaggagcc attataggaa    960
ctttgcttgc tctagcgctc attggtctta tcatcttttg ctgtcgtaaa aagcgcagag   1020
aagaaaaata tgaaaaggaa gttcatcacg atatcaggga agatgtgcca cctccaaaga   1080
gccgtacgtc cactgccaga agctacatcg gcagtaatca ttcatccctg ggtccatgt    1140
ctccttccaa catggaagga tattccaaga ctcagtataa ccaagtacca agtgaagact   1200
ttgaacgcac tcctcagagt ccgactctcc cacctgctaa gttcaagtac ccttacaaga   1260
ctgatggaat tacagttgta taaatatgga ctactgaaga atctgaagta ttgtattatt   1320
tgactttatt ttaggcctct agtaaagact taaatgtttt ttaaaaaaag cacaaggcac   1380
agagattaga gcagctgtaa gaacacatct actttatgca atggcattag acatgtaagt   1440
cagatgtcat gtcaaaatta gtacgagcca aattctttgt taaaaaaccc tatgtatagt   1500
gacactgata gttaaaagat gttttattat attttcaata actaccacta acaaattttt   1560
aacttttcat atgcatattc tgatatgtgg tcttttagga aagtatggt taatagttga    1620
tttttcaaag gaatttttaa aattcttacg ttctgtttaa tgttttttgc              1669
```

<210> SEQ ID NO 14
<211> LENGTH: 352
<212> TYPE: PRT
<213> ORGANISM: Homo sapiens

<400> SEQUENCE: 14

```
Met Ala Leu Leu Leu Cys Phe Val Leu Leu Cys Gly Val Val Asp Phe
1               5                   10                  15

Ala Arg Ser Leu Ser Ile Thr Thr Pro Glu Glu Met Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ala Asp Asn
    50                  55                  60

Gln Lys Val Asp Gln Val Ile Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Val Leu Val Lys Pro Ser Gly Ala
    130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
            180                 185                 190

Thr Ser Ser Val Ile Ser Val Lys Asn Ala Ser Ser Glu Tyr Ser Gly
        195                 200                 205

Thr Tyr Ser Cys Thr Val Arg Asn Arg Val Gly Ser Asp Gln Cys Leu
    210                 215                 220
```

```
Leu Arg Leu Asn Val Val Pro Pro Ser Asn Lys Ala Gly Leu Ile Ala
225                 230                 235                 240

Gly Ala Ile Ile Gly Thr Leu Leu Ala Leu Ala Leu Ile Gly Leu Ile
                245                 250                 255

Ile Phe Cys Cys Arg Lys Lys Arg Glu Glu Lys Tyr Glu Lys Glu
            260                 265                 270

Val His His Asp Ile Arg Glu Asp Val Pro Pro Lys Ser Arg Thr
        275                 280                 285

Ser Thr Ala Arg Ser Tyr Ile Gly Ser Asn His Ser Ser Leu Gly Ser
    290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Thr Pro Gln Ser Pro Thr Leu Pro
                325                 330                 335

Pro Ala Lys Phe Lys Tyr Pro Tyr Lys Thr Asp Gly Ile Thr Val Val
                340                 345                 350

<210> SEQ ID NO 15
<211> LENGTH: 3997
<212> TYPE: DNA
<213> ORGANISM: Homo sapiens

<400> SEQUENCE: 15
gtgccaaggc ggctgggggc ggcgagcggg gccgcgggcg cgcaccgact caagagccga      60
ctgtcagcct cggcgggccg gagttctccg gcgctgggac aggggcgctg ggacaggggc     120
gctgggggcg agccctggcg ggggccaggt ccgaggaccc tggcgcggc ggccccgcca     180 ggaggtccgg ccgcgagcgt gacctcacgg ggaggggcca gcgcggcggc ctgggcgctg     240
agccgagcgc cgggagagca gcgcagaagc cgagccgcga ggagcgcact ccgtggcccc     300
gatggagcgg tacaaagccc tggaacagct gctgacagag ttggatgact cctcaagat     360 tcttgaccag gagaacctga gcagcacagc actggtgaag aagagctgcc tggcggagct     420
cctccggctt tacaccaaaa gcagcagctc tgatgaggag tacatttata tgaacaaagt     480
gaccatcaac aagcaacaga atgcagagtc tcaaggcaaa gcgcctgagg agcagggcct     540
gctacccaat ggggagccca gccagcactc ctcggcccct cagaagagcc ttccagacct     600
cccgccaccc aagatgattc agaacggaa acagcttgcc atcccaaaga cggagtctcc     660
agagggctac tatgaagagg ctgagccata tgacacatcc ctcaatgagg acggagaggc     720
tgtgagcagc tcctacgagt cctacgatga agggacggc agcaagggca agtcggcccc     780
ttaccagtgg ccctcgccgg aggccggcat cgagctgatg cgtgacgccc gcatctgcgc     840
cttcctgtgg cgcaagaagt ggctgggaca gtgggccaag cagctctgtg tcatcaagga     900
caacaggctt ctgtgctaca atcctccaa ggaccacagc cctcagctgg acgtgaacct     960
actgggcagc agcgtcattc acaaggagaa gcaagtgcgg aagaaggagc acaagctgaa    1020
gatcacaccg atgaatgccg atgtgattgt gctgggcctg cagagcaagg accaggctga    1080
gcagtggctc agggtcatcc aggaagtgag cggcctgcct tccgaaggag catctgaagg    1140
aaaccagtac accccggatg cccagcgctt taactgccag aaaccagata tagctgagaa    1200
gtacctgtcg gcttcagagt atgggagctc cgtggatggc caccctgagg tcccagaaac    1260
caaagacgtc aagaagaaat gttctgctgg cctcaaactg agcaacctaa tgaatctggg    1320
caggaagaaa tccacctcac tggagcctgt ggagaggtcc ctcgagacat ccagttacct    1380
gaacgtgctg gtgaacagcc agtggaagtc tcgctggtgc tctgtcaggg acaatcacct    1440
```

-continued

```
gcacttctac caggaccgga accggagcaa ggtggcccag caacccctca gcctggtggg    1500
ctgcgaggtg gtcccagacc ccagccccga ccacctctac tccttccgca tcctccacaa    1560
gggcgaggag ctggccaagc ttgaggccaa gtcttccgag gaaatgggcc actggctggg    1620
tctcctgctc tctgagtcag gctccaagac agacccagaa gagttcacct acgactatgt    1680
ggatgccgat agggtctcct gtattgtgag tgcggccaaa aactctctct tactgatgca    1740
gagaaagttc tcagagccca acacttacat cgatggcctg cctagccagg accgccagga    1800
ggagctgtat gacgacgtgg acctgtcaga gctcacagct gcggtggagc ctaccgagga    1860
agccacccct gttgcagatg acccaaatga gagagaatct gaccgagtgt acctggacct    1920
cacacctgtc aagtcctttc tgcatggccc cagcagtgca caggcccagg cctcctcccc    1980
gacgttgtcc tgcctggaca atgcaactga ggccctcccg gcagactcag cccaggtcc    2040 caccccagat gagccctgca taaagtgtcc agagaacctg gagaacagc agctggagag    2100 tttggagcca gaggatcctt ccctgagaat caccaccgtc aaaatccaga cggaacagca    2160
gagaatctcc ttcccaccga gctgcccgga tgccgtggtg gccaccccac ctggtgccag    2220
cccacctgtg aaggacaggt tgcgcgtgac cagtgcagag atcaagcttg caagaatcg    2280 gacagaagct gaggtgaagc ggtacacaga ggagaaggag aggcttgaaa agaagaagga    2340
agaaatccgg gggcacctgg ctcagctccg gaaagagaaa cgggagctaa aggaaaccct    2400
actgaaatgc acagacaagg aagtcctggc gagcctggag cagaagctga aggaaattga    2460
cgaggagtgc cggggcgagg agagcaggcg cgtggacctg agctcagca tcatggaggt    2520 gaaggacaac ctgaagaagg ctgaggcagg gcctgtgacg ttaggcacca ccgtggacac    2580 caccccacctg gagaatgtga gccccgccc aaagctgtc acacctgcct ctgccccaga    2640 ctgtaccca gtcaactctg caaccacact caagaacagg cctctctcgg tcgtggtcac    2700
aggcaaaggc actgtactcc agaaagccaa ggaatgggag aagaaaggag caagttagaa    2760
aacaagcttc atctaaagac tctcatgtca atgtggacct tggtgacaat cctgctttgt    2820
taaagcaaaa actatgcgaa agggtgagtc tgtttagaag aaaaagcaaa gactgaggta    2880
ctgtgaatgg agagcttcag ctaagaggag gctctgtccc ttttcagagc caaaggaaat    2940
aatacaacaa aaaggaggct tctttggaga cctaagtcta ttggatgtaa acaagacgtt    3000
gtatttaggg atgttctgtg tttctttctt ttttgaagtt gtcatcaatt gcttactaa    3060 gatttttaaa tagtgaaaac ctcctgtttta gactttggtg gaagatgaat caaggaagca    3120
gggccctgtc ttatgggtca cgtgtctttg gtgagtgaga agacctaaac tcctggccat    3180
catctcttat ccaatactta gcagttgggg attaaaccat ccttgccttc agttctctcc    3240
aatattacca ggcccaactc agtcttcagt gattttaaac agcattgaca tcatctgtaa    3300
aaccatcatc tgtaaaacca tctatgacat gagttttgag aaacaataat ggggaaaata    3360
tttgggacca agctgaagca ctaatcccac taagttaaag acttctttcc agtccaaggc    3420
aggcctgaat caactgtctt taaataaaat tttaagtgat gctgtattat atataggaaa    3480
aaatgcttaa aatcctgtca tttagaacag tgaaagtat cttttgagat taaagtgact    3540
ctttactgta ggaaaatat tactctgtgt ttacagattc attgctgtgg tcaggccatt    3600
tttaagggaa gagttatta atataaatag tctctgattt taagttctgt ttaatgttca    3660
ttctccttcc aagaacaaag tggtgatttt tggttagggt gatcgccctc ttaaaattgg    3720
cagtgctgtt ccttgtgctg cccctgtctt ttcctctgat ggcattttt tttttttttt    3780 tttaacacag gttgaaacat ttcatctatt atctctgcct catttctgga gggttgtgta    3840
```

-continued

```
tcagttctct aacacttgtt cctgagaact aaatgtcttt ttattctta tttcctctct    3900 cataaacatt tggtgacctt ttaccaagtg gtgagttagt taggtttttt aaaataaaat   3960
gttcattgta tttgaaaaaa aaaaaaaaaa aaaaaaa                            3997
```

<210> SEQ ID NO 16
<211> LENGTH: 818
<212> TYPE: PRT
<213> ORGANISM: Homo sapiens

<400> SEQUENCE: 16

```
Met Glu Arg Tyr Lys Ala Leu Glu Gln Leu Leu Thr Glu Leu Asp Asp
1               5                   10                  15

Phe Leu Lys Ile Leu Asp Gln Glu Asn Leu Ser Ser Thr Ala Leu Val
                20                  25                  30

Lys Lys Ser Cys Leu Ala Glu Leu Leu Arg Leu Tyr Thr Lys Ser Ser
            35                  40                  45

Ser Ser Asp Glu Glu Tyr Ile Tyr Met Asn Lys Val Thr Ile Asn Lys
    50                  55                  60

Gln Gln Asn Ala Glu Ser Gln Gly Lys Ala Pro Glu Gln Gly Leu
65                  70                  75                  80

Leu Pro Asn Gly Glu Pro Ser Gln His Ser Ala Pro Gln Lys Ser
                85                  90                  95

Leu Pro Asp Leu Pro Pro Lys Met Ile Pro Glu Arg Lys Gln Leu
            100                 105                 110

Ala Ile Pro Lys Thr Glu Ser Pro Glu Gly Tyr Tyr Glu Glu Ala Glu
        115                 120                 125

Pro Tyr Asp Thr Ser Leu Asn Glu Asp Gly Glu Ala Val Ser Ser Ser
    130                 135                 140

Tyr Glu Ser Tyr Asp Glu Asp Gly Ser Lys Gly Lys Ser Ala Pro
145                 150                 155                 160

Tyr Gln Trp Pro Ser Pro Glu Ala Gly Ile Glu Leu Met Arg Asp Ala
                165                 170                 175

Arg Ile Cys Ala Phe Leu Trp Arg Lys Lys Trp Leu Gly Gln Trp Ala
            180                 185                 190

Lys Gln Leu Cys Val Ile Lys Asp Asn Arg Leu Leu Cys Tyr Lys Ser
        195                 200                 205

Ser Lys Asp His Ser Pro Gln Leu Asp Val Asn Leu Leu Gly Ser Ser
    210                 215                 220

Val Ile His Lys Glu Lys Gln Val Arg Lys Lys Glu His Lys Leu Lys
225                 230                 235                 240

Ile Thr Pro Met Asn Ala Asp Val Ile Val Leu Gly Leu Gln Ser Lys
                245                 250                 255

Asp Gln Ala Glu Gln Trp Leu Arg Val Ile Gln Glu Val Ser Gly Leu
            260                 265                 270

Pro Ser Glu Gly Ala Ser Glu Gly Asn Gln Tyr Thr Pro Asp Ala Gln
        275                 280                 285

Arg Phe Asn Cys Gln Lys Pro Asp Ile Ala Glu Lys Tyr Leu Ser Ala
    290                 295                 300

Ser Glu Tyr Gly Ser Ser Val Asp Gly His Pro Glu Val Pro Glu Thr
305                 310                 315                 320

Lys Asp Val Lys Lys Lys Cys Ser Ala Gly Leu Lys Leu Ser Asn Leu
                325                 330                 335

Met Asn Leu Gly Arg Lys Lys Ser Thr Ser Leu Glu Pro Val Glu Arg
            340                 345                 350
```

-continued

```
Ser Leu Glu Thr Ser Ser Tyr Leu Asn Val Leu Val Asn Ser Gln Trp
            355                 360                 365
Lys Ser Arg Trp Cys Ser Val Arg Asp Asn His Leu His Phe Tyr Gln
    370                 375                 380
Asp Arg Asn Arg Ser Lys Val Ala Gln Gln Pro Leu Ser Leu Val Gly
385                 390                 395                 400
Cys Glu Val Val Pro Asp Pro Ser Pro Asp His Leu Tyr Ser Phe Arg
                405                 410                 415
Ile Leu His Lys Gly Glu Glu Leu Ala Lys Leu Glu Ala Lys Ser Ser
                420                 425                 430
Glu Glu Met Gly His Trp Leu Gly Leu Leu Leu Ser Glu Ser Gly Ser
            435                 440                 445
Lys Thr Asp Pro Glu Glu Phe Thr Tyr Asp Tyr Val Asp Ala Asp Arg
    450                 455                 460
Val Ser Cys Ile Val Ser Ala Ala Lys Asn Ser Leu Leu Leu Met Gln
465                 470                 475                 480
Arg Lys Phe Ser Glu Pro Asn Thr Tyr Ile Asp Gly Leu Pro Ser Gln
                485                 490                 495
Asp Arg Gln Glu Glu Leu Tyr Asp Asp Val Asp Leu Ser Glu Leu Thr
            500                 505                 510
Ala Ala Val Glu Pro Thr Glu Glu Ala Thr Pro Val Ala Asp Asp Pro
    515                 520                 525
Asn Glu Arg Glu Ser Asp Arg Val Tyr Leu Asp Leu Thr Pro Val Lys
530                 535                 540
Ser Phe Leu His Gly Pro Ser Ser Ala Gln Ala Gln Ala Ser Ser Pro
545                 550                 555                 560
Thr Leu Ser Cys Leu Asp Asn Ala Thr Glu Ala Leu Pro Ala Asp Ser
                565                 570                 575
Gly Pro Gly Pro Thr Pro Asp Glu Pro Cys Ile Lys Cys Pro Glu Asn
            580                 585                 590
Leu Gly Glu Gln Gln Leu Glu Ser Leu Glu Pro Glu Asp Pro Ser Leu
    595                 600                 605
Arg Ile Thr Thr Val Lys Ile Gln Thr Glu Gln Arg Ile Ser Phe
610                 615                 620
Pro Pro Ser Cys Pro Asp Ala Val Val Ala Thr Pro Pro Gly Ala Ser
625                 630                 635                 640
Pro Pro Val Lys Asp Arg Leu Arg Val Thr Ser Ala Glu Ile Lys Leu
                645                 650                 655
Gly Lys Asn Arg Thr Glu Ala Glu Val Lys Arg Tyr Thr Glu Glu Lys
            660                 665                 670
Glu Arg Leu Glu Lys Lys Glu Glu Ile Arg Gly His Leu Ala Gln
    675                 680                 685
Leu Arg Lys Glu Lys Arg Glu Leu Lys Glu Thr Leu Leu Lys Cys Thr
    690                 695                 700
Asp Lys Glu Val Leu Ala Ser Leu Glu Gln Lys Leu Lys Glu Ile Asp
705                 710                 715                 720
Glu Glu Cys Arg Gly Glu Glu Ser Arg Arg Val Asp Leu Glu Leu Ser
                725                 730                 735
Ile Met Glu Val Lys Asp Asn Leu Lys Lys Ala Glu Ala Gly Pro Val
            740                 745                 750
Thr Leu Gly Thr Thr Val Asp Thr Thr His Leu Glu Asn Val Ser Pro
    755                 760                 765
```

Arg Pro Lys Ala Val Thr Pro Ala Ser Ala Pro Asp Cys Thr Pro Val
    770                 775                 780

Asn Ser Ala Thr Thr Leu Lys Asn Arg Pro Leu Ser Val Val Val Thr
785                 790                 795                 800

Gly Lys Gly Thr Val Leu Gln Lys Ala Lys Glu Trp Glu Lys Lys Gly
                805                 810                 815

Ala Ser

<210> SEQ ID NO 17
<211> LENGTH: 1606
<212> TYPE: DNA
<213> ORGANISM: Homo sapiens

<400> SEQUENCE: 17

| | | | | | |
|---|---|---|---|---|---|
| aaatgtgacc | ggccgcggct | ccggcagtca | acgcctgcct | cctctcgagc | gtcctcagcg | 60 |
| cagccgccgc | ccgcggagcc | agcacgaacg | agcccagcac | cggccggatg | gagcgtccgc | 120 |
| aacccgacag | catgccccag | gatttgtcag | aggccctgaa | ggaggccacc | aaggaggtgc | 180 |
| acacccaggc | agagaatgct | gagttcatga | ggaactttca | gaagggccag | gtgacccgag | 240 |
| acggcttcaa | gctggtgatg | gcctccctgt | accacatcta | tgtggccctg | gaggaggaga | 300 |
| ttgagcgcaa | caaggagagc | ccagtcttcg | cccctgtcta | cttcccagaa | gagctgcacc | 360 |
| gcaaggctgc | cctggagcag | gacctggcct | tctggtacgg | gccccgctgg | caggaggtca | 420 |
| tcccctacac | accagccatg | cagcgctatg | tgaagcggct | ccacgaggtg | ggcgcacag | 480 |
| agcccgagct | gctggtggcc | cacgcctaca | cccgctacct | gggtgacctg | tctgggggcc | 540 |
| aggtgctcaa | aaagattgcc | cagaaagccc | tggacctgcc | cagctctggc | gagggcctgg | 600 |
| ccttcttcac | cttccccaac | attgccagtg | ccaccaagtt | caagcagctc | taccgctccc | 660 |
| gcatgaactc | cctggagatg | actcccgcag | tcaggcagag | ggtgatagaa | gaggccaaga | 720 |
| ctgcgttcct | gctcaacatc | cagctctttg | aggagttgca | ggagctgctg | acccatgaca | 780 |
| ccaaggacca | gagcccctca | cgggcaccag | ggcttcgcca | gcgggccagc | aacaaagtgc | 840 |
| aagattctgc | ccccgtggag | actcccagag | ggaagccccc | actcaacacc | cgctcccagg | 900 |
| ctccgcttct | ccgatgggtc | cttacactca | gctttctggt | ggcgacagtt | gctgtagggc | 960 |
| tttatgccat | gtgaatgcag | gcatgctggc | tcccagggcc | atgaactttg | tccggtggaa | 1020 |
| ggccttcttt | ctagagaggg | aattctcttg | gctggcttcc | ttaccgtggg | cactgaaggc | 1080 |
| tttcagggcc | tccagccctc | tcactgtgtc | cctctctctg | gaaaggagga | aggagcctat | 1140 |
| ggcatcttcc | ccaacgaaaa | gcacatccag | gcaatggcct | aaacttcaga | gggggcgaag | 1200 |
| ggatcagccc | tgcccttcag | catcctcagt | tcctgcagca | gagcctggaa | gacaccctaa | 1260 |
| tgtggcagct | gtctcaaacc | tccaaaagcc | ctgagtttca | agtatccttg | ttgacacggc | 1320 |
| catgaccact | ttccccgtgg | gccatggcaa | tttttacaca | aacctgaaaa | gatgttgtgt | 1380 |
| cttgtgtttt | tgtcttatt | tgttggagc | cactctgttc | ctggctcagc | ctcaaatgca | 1440 |
| gtattttgt | tgtgttctgt | tgtttttata | gcagggttgg | ggtggttttt | gagccatgcg | 1500 |
| tgggtgggga | gggaggtgtt | taacggcact | gtggccttgg | tctaacttttt | gtgtgaaata | 1560 |
| ataaacaaca | ttgtctgata | gtagcttgaa | aaaaaaaaa | aaaaaa | | 1606 |

<210> SEQ ID NO 18
<211> LENGTH: 288
<212> TYPE: PRT
<213> ORGANISM: Homo sapiens

<400> SEQUENCE: 18

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
    50                  55                  60

Ile Glu Arg Asn Lys Glu Ser Pro Val Phe Ala Pro Val Tyr Phe Pro
65              70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
        115                 120                 125

Leu Val Ala His Ala Tyr Thr Arg Tyr Leu Gly Asp Leu Ser Gly Gly
    130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
        195                 200                 205

Leu Asn Ile Gln Leu Phe Glu Glu Leu Gln Glu Leu Leu Thr His Asp
    210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Arg Ser Gln Ala Pro Leu Leu Arg Trp Val Leu
            260                 265                 270

Thr Leu Ser Phe Leu Val Ala Thr Val Ala Val Gly Leu Tyr Ala Met
        275                 280                 285

<210> SEQ ID NO 19
<211> LENGTH: 2207
<212> TYPE: DNA
<213> ORGANISM: Homo sapiens

<400> SEQUENCE: 19
cacttcctcc ccagacaggg gtagtgcgag gccgggcaca gccttcctgt gtggttttac       60
cgcccagaga gcgtcatgga cctggggaaa ccaatgaaaa gcgtgctggt ggtggctctc      120
cttgtcattt tccaggtatg cctgtgtcaa gatgaggtca cggacgatta catcggagac      180
aacaccacag tggactacac tttgttcgag tctttgtgct ccaagaagga cgtgcggaac      240
tttaaagcct ggttcctccc tatcatgtac tccatcattt gtttcgtggg cctactgggc      300
aatgggctgg tcgtgttgac ctatatctat ttcaagaggc tcaagaccat gaccgatacc      360
tacctgctca acctggcggt ggcagacatc ctcttcctcc tgaccccttc cttctgggcc      420
tacagcgcgg ccaagtcctg ggtcttcggt gtccactttt gcaagctcat ctttgccatc      480

| | | |
|---|---|---|
| tacaagatga gcttcttcag tggcatgctc ctacttcttt gcatcagcat tgaccgctac | 540 | |
| gtggccatcg tccaggctgt ctcagctcac cgccaccgtg cccgcgtcct tctcatcagc | 600 | |
| aagctgtcct gtgtgggcat ctggatacta gccacagtgc tctccatccc agagctcctg | 660 | |
| tacagtgacc tccagaggag cagcagtgag caagcgatgc gatgctctct catcacagag | 720 | |
| catgtggagg cctttatcac catccaggtg gcccagatgg tgatcggctt tctggtcccc | 780 | |
| ctgctggcca tgagcttctg ttaccttgtc atcatccgca ccctgctcca ggcacgcaac | 840 | |
| tttgagcgca acaaggccat caaggtgatc atcgctgtgg tcgtggtctt catagtcttc | 900 | |
| cagctgccct acaatggggt ggtcctggcc cagacggtgg ccaacttcaa catcaccagt | 960 | |
| agcacctgtg agctcagtaa gcaactcaac atcgcctacg acgtcaccta cagcctggcc | 1020 | |
| tgcgtccgct gctgcgtcaa ccctttcttg tacgccttca tcggcgtcaa gttccgcaac | 1080 | |
| gatctcttca agctcttcaa ggacctgggc tgcctcagcc aggagcagct ccggcagtgg | 1140 | |
| tcttcctgtc ggcacatccg gcgctcctcc atgagtgtgg aggccgagac caccaccacc | 1200 | |
| ttctccccat aggcgactct tctgcctgga ctagagggac ctctcccagg gtccctgggg | 1260 | |
| tggggatagg gagcagatgc aatgactcag gacatccccc cgccaaaagc tgctcaggga | 1320 | |
| aaagcagctc tcccctcaga gtgcaagccc ctgctccaga agatagcttc accccaatcc | 1380 | |
| cagctacctc aaccaatgcc aaaaaaagac agggctgata agctaacacc agacagacaa | 1440 | |
| cactgggaaa cagaggctat tgtcccctaa accaaaaact gaaagtgaaa gtccagaaac | 1500 | |
| tgttcccacc tgctggagtg aaggggccaa ggagggtgag tgcaaggggc gtgggagtgg | 1560 | |
| cctgaagagt cctctgaatg aaccttctgg cctcccacag actcaaatgc tcagaccagc | 1620 | |
| tcttccgaaa accaggcctt atctccaaga ccagagatag tggggagact tcttggcttg | 1680 | |
| gtgaggaaaa gcggacatca gctggtcaaa caaactctct gaacccctcc ctccatcgtt | 1740 | |
| ttcttcactg tcctccaagc cagcgggaat ggcagctgcc acgccgccct aaaagcacac | 1800 | |
| tcatccccctc acttgccgcg tcgccctccc aggctctcaa caggggagag tgtggtgttt | 1860 | |
| cctgcaggcc aggccagctg cctccgcgtg atcaaagcca cactctgggc tccagagtgg | 1920 | |
| ggatgacatg cactcagctc ttggctccac tgggatggga ggagaggaca agggaaatgt | 1980 | |
| caggggcggg gagggtgaca gtggccgccc aaggcccacg agcttgttct tgttctttg | 2040 | |
| tcacagggac tgaaaacctc tcctcatgtt ctgctttcga ttcgttaaga gagcaacatt | 2100 | |
| ttacccacac acagataaag ttttcccttg aggaaacaac agctttaaaa gaaaagaaa | 2160 | |
| aaaaagtct ttggtaaatg gcaaaaaaaa aaaaaaaaaa aaaaaa | 2207 | |

<210> SEQ ID NO 20
<211> LENGTH: 378
<212> TYPE: PRT
<213> ORGANISM: Homo sapiens

<400> SEQUENCE: 20

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

-continued

```
Tyr Ser Ile Ile Cys Phe Val Gly Leu Leu Gly Asn Gly Leu Val Val
 65              70                  75                  80

Leu Thr Tyr Ile Tyr Phe Lys Arg Leu Lys Thr Met Thr Asp Thr Tyr
                 85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
            115                 120                 125

Cys Lys Leu Ile Phe Ala Ile Tyr Lys Met Ser Phe Phe Ser Gly Met
            130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
                180                 185                 190

Glu Leu Leu Tyr Ser Asp Leu Gln Arg Ser Ser Ser Glu Gln Ala Met
            195                 200                 205

Arg Cys Ser Leu Ile Thr Glu His Val Glu Ala Phe Ile Thr Ile Gln
            210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
            275                 280                 285

Ala Asn Phe Asn Ile Thr Ser Ser Thr Cys Glu Leu Ser Lys Gln Leu
            290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
            370                 375
```